United States Patent
Vild et al.

(10) Patent No.: US 12,380,965 B2
(45) Date of Patent: *Aug. 5, 2025

(54) PREDICTION OF INFECTION IN PLANT PRODUCTS

(71) Applicant: Apeel Technology, Inc., Goleta, CA (US)

(72) Inventors: Cody Vild, Santa Barbara, CA (US); Savannah Braden, Goleta, CA (US); Matthew Kahlscheuer, Goleta, CA (US); Louis Perez, Santa Barbara, CA (US)

(73) Assignee: Apeel Technology, Inc., Goleta, CA (US)

( * ) Notice: Subject to any disclaimer, the term of this patent is extended or adjusted under 35 U.S.C. 154(b) by 796 days.

This patent is subject to a terminal disclaimer.

(21) Appl. No.: 17/499,068

(22) Filed: Oct. 12, 2021

(65) Prior Publication Data

US 2022/0028496 A1    Jan. 27, 2022

Related U.S. Application Data

(63) Continuation of application No. 17/090,834, filed on Nov. 5, 2020, now Pat. No. 11,170,872.

(60) Provisional application No. 62/930,999, filed on Nov. 5, 2019.

(51) Int. Cl.
| | |
|---|---|
| G16B 40/00 | (2019.01) |
| A01G 22/00 | (2018.01) |
| A01N 1/00 | (2006.01) |
| A01N 3/00 | (2006.01) |
| C12Q 1/6895 | (2018.01) |
| G06N 5/04 | (2023.01) |
| G06N 20/00 | (2019.01) |
| G06Q 10/0832 | (2023.01) |

(52) U.S. Cl.
CPC ............ *G16B 40/00* (2019.02); *A01G 22/00* (2018.02); *A01N 1/00* (2013.01); *A01N 3/00* (2013.01); *C12Q 1/6895* (2013.01); *G06N 5/04* (2013.01); *G06N 20/00* (2019.01); *G06Q 10/0832* (2013.01); *C12Q 2600/13* (2013.01); *C12Q 2600/158* (2013.01)

(58) Field of Classification Search
CPC ............ C12Q 2600/158; C12Q 1/6895; C12Q 2600/13; G06N 20/00; G16B 20/00; G16B 40/00; G16B 25/10; G16B 40/20; G16B 30/00; G16B 30/10; G16B 20/40; G16B 50/00; G16B 50/30; G06Q 50/02; G06F 18/214; G06F 18/213

See application file for complete search history.

(56) References Cited

U.S. PATENT DOCUMENTS

| | | |
|---|---|---|
| 5,214,066 A | 5/1993 | Szabo |
| 5,445,953 A | 8/1995 | Dorner et al. |
| 5,962,765 A | 10/1999 | St.Leger et al. |
| 6,011,019 A | 1/2000 | Thomas et al. |
| 6,251,955 B1 | 6/2001 | Bulawa |
| 6,486,133 B1 | 11/2002 | Herlyn et al. |
| 7,138,273 B2 | 11/2006 | Rommens et al. |
| 7,851,448 B2 | 12/2010 | Skubatch |
| 8,518,408 B2 | 8/2013 | Baumert et al. |
| 9,181,310 B2 | 11/2015 | Gabriel et al. |
| 9,447,429 B2 | 9/2016 | Carrington et al. |
| 9,940,434 B2 | 4/2018 | Kingsmore et al. |
| 10,233,462 B2 | 3/2019 | Bradley et al. |
| 11,170,872 B2 * | 11/2021 | Vild ...................... G16B 40/00 |
| 2002/0155445 A1 | 10/2002 | Jarvik |
| 2003/0115627 A1 | 6/2003 | Laroche et al. |
| 2004/0048810 A1 | 3/2004 | Shaw et al. |
| 2004/0078847 A1 | 4/2004 | Paldi |
| 2004/0091935 A1 | 5/2004 | Doxsey |
| 2004/0133936 A1 | 7/2004 | Rossiter et al. |
| 2004/0153249 A1 | 8/2004 | Zhang et al. |

(Continued)

FOREIGN PATENT DOCUMENTS

| | | |
|---|---|---|
| CN | 107742290 | 2/2018 |
| CN | 108323184 | 7/2018 |

(Continued)

OTHER PUBLICATIONS

Andrews, "FastQC: A Quality Control Tool for High Throughput Sequence Data," 2010, retrieved on Jan. 14, 2022, retrieved from URL <https://www.bioinformatics.babraham.ac.uk/projects/fastqc/>, 6 pages.

(Continued)

*Primary Examiner* — Mary K Zeman
(74) *Attorney, Agent, or Firm* — Fish & Richardson P.C.

(57) ABSTRACT

A method for predicting a likelihood of infection in a set of similarly sourced plant products is disclosed. A subset of plant products is selected from the set of plant products. For each plant product in the subset, a level of expression of one or more infection biomarkers, and optionally a level of expression of one more housekeeping biomarkers, are determined. A set of biomarker expression statistics for the subset of plant products is determined based on the determined levels of expression of the one or more infection biomarkers and optionally the levels of expression of the one or more housekeeping biomarkers for each plant product in the subset. A likelihood of infection in the set of plant products is then predicted based at least in part on the determined set of biomarker expression statistics for the subset of plant products.

19 Claims, 22 Drawing Sheets

Specification includes a Sequence Listing.

(56) References Cited

U.S. PATENT DOCUMENTS

| | | | |
|---|---|---|---|
| 2005/0144664 | A1 | 6/2005 | Smith et al. |
| 2006/0040335 | A1 | 2/2006 | Butt et al. |
| 2006/0206946 | A1 | 9/2006 | Hamza |
| 2008/0083042 | A1 | 4/2008 | Butruille et al. |
| 2010/0077500 | A1 | 3/2010 | Umaharan et al. |
| 2011/0061128 | A1 | 3/2011 | Roberts et al. |
| 2013/0036519 | A1 | 2/2013 | Chiapelli et al. |
| 2014/0036054 | A1 | 2/2014 | Zouridakis |
| 2014/0127672 | A1 | 5/2014 | Davis et al. |
| 2014/0236613 | A1 | 8/2014 | McMillan et al. |
| 2014/0255922 | A1 | 9/2014 | Wu et al. |
| 2015/0371006 | A1 | 12/2015 | McMillan et al. |
| 2015/0373937 | A1 | 12/2015 | Reeves et al. |
| 2017/0045528 | A1 | 2/2017 | Blumberg et al. |
| 2017/0260586 | A1* | 9/2017 | Rudell, Jr. ............. G16B 20/20 |
| 2017/0273285 | A1 | 9/2017 | Murphy et al. |
| 2017/0303544 | A1 | 10/2017 | Santiago Olmedo et al. |
| 2018/0038877 | A1 | 2/2018 | Schaefer |
| 2018/0122511 | A1 | 5/2018 | Apte et al. |
| 2018/0312867 | A1 | 11/2018 | Boukharov et al. |
| 2019/0119336 | A1 | 4/2019 | Fitches et al. |
| 2021/0029866 | A1* | 2/2021 | Placella ................. G06Q 10/04 |
| 2021/0151127 | A1 | 5/2021 | Vild et al. |
| 2021/0270839 | A1 | 9/2021 | Southern |
| 2022/0028496 | A1* | 1/2022 | Vild ........................ G06N 5/04 |
| 2022/0132748 | A1* | 5/2022 | Vild ....................... G16B 25/10 47/1.7 |

FOREIGN PATENT DOCUMENTS

| | | |
|---|---|---|
| CN | 110188635 | 8/2019 |
| JP | 2007-089525 A | 3/2009 |
| WO | 1997005553 | 2/1997 |
| WO | 1997009417 | 3/1997 |
| WO | 1998043476 | 10/1998 |
| WO | 2000071671 | 11/2000 |
| WO | 2001049104 | 7/2001 |
| WO | 2003062455 | 7/2003 |
| WO | 2004092208 | 10/2004 |
| WO | 2004104193 | 12/2004 |
| WO | 2005058931 | 6/2005 |
| WO | 2005083096 | 9/2005 |
| WO | 2006135904 | 12/2006 |
| WO | 2007117482 | 10/2007 |
| WO | 2008106551 | 9/2008 |
| WO | 2010129999 | 11/2010 |
| WO | 2011116131 | 9/2011 |
| WO | 2013192316 | 12/2013 |
| WO | 2015066341 | 5/2015 |
| WO | 2015092548 | 6/2015 |
| WO | 2015105523 | 7/2015 |
| WO | 2015191789 | 12/2015 |
| WO | 2016051398 | 4/2016 |
| WO | 2016191293 | 12/2016 |
| WO | 2017062618 | 4/2017 |
| WO | 2018101223 | 6/2018 |
| WO | 2018220385 | 12/2018 |
| WO | 2019090017 | 5/2019 |

OTHER PUBLICATIONS

Antico et al., "Insights into the role of jasmonic acid-mediated defenses against necrotrophic and biotrophic fungal pathogens," Front. Biol., Jan. 2012, 7:48-56.
Blighe et al., "PCAtools: Everything Principal Component Analysis," Oct. 26, 2021, retrieved on Jan. 14, 2022, retrieved from URL <https://bioconductor.org/packages/release/bioc/vignettes/PCAtools/inst/doc/PCAtools.html>, 44 bages.
Djami-Tchatchou et al., "Expression of defence-related genes in avocado fruit (cv. Fuerte) infected with Colletotrichum gloeosporioides," South Afr. J. Bot., May 2013, 86:92-100.
Dobin et al., "STAR: ultrafast universal RNA-seq aligner," Bioinformatics, Jan. 2013, 29(1):15-21.

Galsurker et al., "Fruit Stem-End Rot," Horticulturae, Nov. 2018, 4(4):16 pages.
Hartill et al., "Stem-End Rots: The Infection Portal," New Zealand Avocado Growers Association Annual Research Report, 2002, 1-8.
He et al., "Epigenetic Environmental Memories in Plants: Establishment, Maintenance, and Reprogramming," Trends Genet., Nov. 2018, 34(11):856-866, 11 pages.
Howe et al., "Ensembl 2021," Nucleic Acids Res., Jan. 2021, 49(D1):D884-D891.
Kolde, "pheatmap," Jan. 2019, retrieved from URL <https://cran.r-project.org/web/packages/pheatmap/pheatmap.pdf>, 8 pages.
Li et al., "The Sequence Alignment/Map format and SAMtools," Bioinformatics, Aug. 2009, 25(16):2078-2079.
Liao et al., "featureCounts: an efficient general purpose program for assigning sequence reads to genomic features," Bioinformatics, Apr. 2014, 30(7):923-930.
Love et al., "Moderated estimation of fold change and dispersion for RNA-seq data with DESeq2," Genome Biol., Dec. 2014, 15(550):21 pages.
Miller et al., "Plant immunity: unravelling the complexity of plant responses to biotic stresses," Ann. Bot., Mar. 2017, 119(5):681-687.
Hcdc.noaa.gov [online], "Climate Data Online (CDO)," retrieved on Jan. 14, 2022, retrieved from URL <https://www.hcdc.noaa.gov/cdo-web/>, 2 pages.
Pantano et al., "DEGreport: Report of DEG analysis," 2021, retrieved on Jan. 14, 2022, retrieved from URL <https://bioconductor.org/packages/release/bioc/html/DEGreport.html>, 4 pages.
Pruitt et al., "Plant immunity unified," Nature Plants, Mar. 2021, 7:382-383.
Raudvere et al., "g:Profiler: a web server for functional enrichment analysis and conversions of gene lists (2019 update)," Nucleic Acids Res., Jul. 2019, 47(W1):W191-W198.
Rendón-Anaya et al., "The avocado genome informs deep angiosperm phylogeny, highlights introgressive hybridization, and reveals pathogen-influenced gene space adaptation," Proc. Natl. Acad. Sci., Aug. 2019, 116(34):17081-17089.
Van den Berg et al., "Advances in Understanding Defense Mechanisms in Persea americana Against Phytophthora cinnamomi," Front. Plant Sci., Mar. 2021, 12(636339):1-17.
Xie et al., "Regulation of Lignin Biosynthesis and Its Role in Growth-Defense Tradeoffs," Front. Plant Sci., Sep. 2018, 9(1427):1-9.
Xoca-Orozco et al., "Transcriptomic Analysis of Avocado Hass (Persea americana Mill) in the Interaction System Fruit-Chitosan-Colletotrichum," Front. Plant Sci., Jun. 2017, 8(956):1-13.
International Search Report and Written Opinion in International Appln. No. PCT/US2021/058212, mailed Feb. 22, 2022, 16 pages.
Tiwari et al., "Volatile organic compounds (VOCs): Biomarkers for quality management of horticultural commodities during storage through e-sensing," Trends in Food Science and Technology, Dec. 2020, 106:417-433.
Wenneker et al., "Latent postharvest pathogens of pome fruit and their management: from single measures to a systems intervention approach," European Journal of Plant Pathology, Jan. 2020, 156(3):663-681, 19 pages.
Abdullah et al., "Real-Time PCR for Diagnosing and Quantifying Co-infection by Two Globally Distributed Fungal Pathogens of Wheat," Front. Plant Sci., Aug. 2018, 9(1086): 1-10.
Ascencio-Ibáñez et al., "Global Analysis of Arabidopsis Gene Expression Uncovers a Complex Array of Changes Impacting Pathogen Response and Cell Cycle during Geminivirus Infection," Plant Physiology, Jul. 2008, 148(1):436-454, 23 pages.
Barbedo, "Factors influencing the use of deep learning for plant disease recognition," Biosystems Engineering, Aug. 2018, 172:84-91.
Chandna et al., "Evaluation of Candidate Reference Genes for Gene Expression Normalization in Brassica juncea Using Real Time Quantitative RT-PCR," PLoS ONE, May 2012, 7(5):e36918, 1-10.
Charkowski et al., "Genomics of Plant-Associated Bacteria: The Soft Rot Enterobacteriaceae," Genomics of Plant-Associated Bacteria, Gross et al. (eds), 2014, 37-58.

(56) References Cited

OTHER PUBLICATIONS

Everett et al., "Predicting Avocado Fruit Rots By Quantifying Inoculum Potential In The Orchard Before Harvest," Proceedings V World Avocado Congress, 2003, 601-606.
Fang et al., "Current and Prospective Methods for Plant Disease Detection," Biosensors, Aug. 2015, 5(3):537-561.
Gokulnath et al., "A survey on plant disease prediction using machine learning and deep learning techniques," Inteligencia Artificial, Jan. 2017, 22(63):0-19.
Guarnaccia et al., "Characterisation and pathogenicity of fungal species associated with branch cankers and stem-end rot of avocado in Italy," European Journal of Plant Pathology, Dec. 2016, 1-14.
Hussain et al., "Molecular diagnosis of killer pathogen of potato: phytopthora infestans and its management," Current Trends in Plant Disease Diagnostics and Management Practices, Fungal Biology, Kumar et al.(eds.), 2016, 28 pages.
Jayalakshmi et al., "Statistical Normalization and Back Propagation for Classification," International Journal of Computer Theory and Engineering, Feb. 2011, 3(1):1793-8201, 5 pages.
Jones et al., "Global Dimensions of Plant Virus Diseases: Current Status and Future Perspectives," Ann Rev Virol., Jul. 2019, 6:387-409 and supplemental information, 26 pages.
Khan, "Important Physiological Disorders and Their management in Fruit Crops," Jan. 2017, retrieved from URL <https://www.researchgate.net/publication/312590837_Important_Physiological_Disorders_and_Their_management_in_Fruit_Crops>, 20 pages.
Kolombet et al., "Diagnostics of phytopathogen infection in agricultural plants as a necessary condition for optimizing current fungicide application technologies," Journal of Agricultural Technology, Mar. 1997, 99-110.
Martinelli et al., "Advanced methods of plant disease detection. A Review," Agron Sustain Dev, Jan. 2015, 35:1-25.
Martinelli et al., "Transcriptome Profiling of Citrus Fruit Response to Huanglongbing Disease," PLoS ONE, May 2012, 7(5):e38039, 1-16.
Michailides et al., "Chapter 6: Epidemiological Assessments and Postharvest Disease Incidence," Postharvest pathology, Plant pathology in the 21st century (contributions to the 9th international congress), 2009, vol. 2, Prusky et al (eds.), 69-88.
Pandey et al., "Molecular Tools and Techniques for Detection and Diagnosis of Plant Pathogens," Recent Advances in the Diagnosis and Management of Plant Diseases, Awasthi (ed.), 2015, 253-271.
PCT International Search Report and Written Opinion in International Appln. No. PCT/US2020/059215, mailed Feb. 18, 2021, 16 pages.
Rotter et al., "Statistical modeling of long-term grapevine response to Candidatus Phytoplasnna solani infection in the field," Eur J Pathol., Mar. 2018, 150:653-668.
Rumpf et al., "Early detection and classification of plant diseases with support vector machines based on hyperspectral reflectance," Computers and electronics in agriculture, Oct. 2010, 74(1):91-99.
Sagaram et al., "Bacterial Diversity Analysis of Huanglongbing Pathogen-Infected Citrus, Using PhyloChip Arrays and 16S rRNA Gene Clone Library Sequencing ," Applied and Environmental Microbiology, Mar. 2009, 75(6):1566-1574, 10 pages.
Sharma et al., "Machine Learning Applications for Precision Agriculture: A Comprehensive Review," IEEEAccess, Jan. 2021, 9:4843-4873.
Sikdar et al. "Development of PCR Assays for Diagnosis and Detection of the Pathogens Phacidiopycnis washingtonensis and Sphaeropsis pyriputrescens in Apple Fruit," Plant Disease, Feb. 2014, 98(2):241-246.
Stegle et al., "A robust Bayesian two-sample test for detecting intervals of differential gene expression in nnicroarray time series," J Comp Biol, Apr. 2010, 17(3):355-367.
Steinfaith et al., "Discovering plant metabolic bionnarkers for phenotype prediction using an untargeted approach," Plant Biotechnology Journal, Oct. 2010, 8(8):900-911.
Thomas et al., "Benefits of hyperspectral imaging for plant disease detection and plant protection: a technical perspective," J Plant Disease Prot., Feb. 2018, 125: 5-20.
Thomas et al., "Diagnostic Tools for Plant Biosecurity," Practical Tools for Plant and Food Biosecurity, Plant Pathology in the 21st Century, Gullino et al. (eds), 2017, 8:209-226, 19 pages.
Wang et al., "MetaBoot: a machine learning framework of taxonomical bionnarker discovery for different microbial communities based on nnetagenonnic data," PeerJ, 2015, 3:e993, 1-27.
Saleem et al., "Plant Disease Detection and Classification by Deep Learning," Plants, Oct. 2019, 8(11):468, 22 pages.

\* cited by examiner

Latent infection data processing pipeline for categorical predictor model development

1000B

Starting input: copy number values for actin, PAL, ACO and ACS from individual fruit taken from a known lot

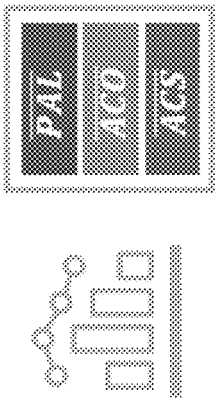

1. Individual sample target gene copy number (PAL, ACO, ACS) normalization to actin housekeeping gene copy number

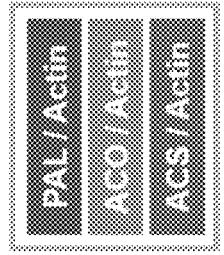

2. Application of mathematical normalization function across all individual gene copy number ratios

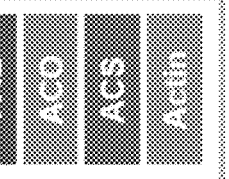

3. Grouping of data into sets by lot to generate dataframe of lot-specific descriptive features, $X_j$, and categorical outcome, $y$

*Feature generation by set*

Categorical assignment of stem end rot incidence > or < 5%

4. Data split into training and test sets as 80/20 random selection maintaining categorical state distribution for the whole in each data split $$\binom{\bigcirc}{n} \times 0.20 = TEST\ (X_i) \binom{\bigcirc}{n_i}$$

$$\binom{\bigcirc}{n} \times 0.80 = TRAIN\ (X_j) \binom{\bigcirc}{n_j}$$

5. Model training and hyperparameter optimization using k-fold cross-validation with only the train data set $$\binom{\bigcirc}{n_j} \Rightarrow f : X_j \rightarrow y_j$$

Result: model, $f$, that takes $X_j$ features and predicts an outcome, $y_j$

FIG. 10B

Predictor model assessment

1000C

The hyperparameter-optimized model, $f$, is then used to generate predicted outcomes, $y_i$, for the test data set, $X_i$ $$\{(o)\}_{n_i} \quad f : X_i \rightarrow y_i$$

These predictions are then compared to known outcomes, $y$, to determine the accuracy, precision and recall of each model $$y_i \parallel y$$

PREDICTION OF INFECTION IN PLANT PRODUCTS

CROSS-REFERENCE TO RELATED APPLICATIONS

This application is a continuation of U.S. application Ser. No. 17/090,834, filed on Nov. 5, 2020, which claims the benefit of U.S. Provisional Patent Application No. 62/930,999 filed on Nov. 5, 2019, which is incorporated herein by reference in its entirety.

BACKGROUND

Many plant products, for example, fruits, sustain high rates of infection. Pre-harvest infection of plant products occurs when a plant product becomes infected by a pathogen during growth. For instance, it has been estimated that approximately 20-40% of avocado trees in avocado orchards, and thus the avocados that they produce, are infected with anthracnose. Unripe, pre-harvest plant products are often asymptomatic of such infection. However, after a plant product has been harvested, ripens, and undergoes senescence, the plant product becomes symptomatic of the infection. Symptoms of infection can include stem-end rot, mold, vascular/internal browning, and other features resulting in a detrimental loss in quality of the plant product.[5]

Plant product infections are highly transmittable by plant products exhibiting infection symptoms. Furthermore, in post-harvest processing, different handling methods and storage conditions leave plant products vulnerable to attack at the plant product surface. Infection and its associated symptoms greatly affect the quality of plant products provided to consumers. As a result, plant products inflicted with infection are often thrown out, making biotic attack of plant products a significant contributor to high rates of post-harvest plant product waste. While many different technologies, including washes and pesticides, have been developed to mitigate plant product losses from infection, it remains difficult for providers to prevent losses stemming from pre-harvest infection of plant products.

As a result of these problems caused by plant product infection, there is a need to identify infected plant products before the infected plant products are symptomatic and capable of transmitting infection to other plant products. Early detection of infected plant products enables treatment and segregation of infected plant products from uninfected plant products, thereby reducing the spread of infection, reducing plant product waste, and improving customer acceptance. By reducing plant product waste and improving customer acceptance, providers can guarantee a higher quality of plant products, thereby enabling the providers to differentiate themselves from other providers in the marketplace.

Current methods for identifying infection in unripe, asymptomatic plant products involve direct detection of infection by quantifying biomarkers (e.g., DNA, RNA, etc.) of the pathogen that causes the infection.[1-4] However, as infection-causing pathogens are generally present in trace quantities within a plant product, direct detection of infection in plant products via quantification of pathogen biomarkers can be difficult and unreliable.

SUMMARY

In one aspect, the present disclosure provides a method of predicting a likelihood of infection in a set of n similarly sourced plant products, wherein n is an integer greater than 10. The method includes selecting a subset of m plant products from the set of plant products, wherein m is an integer greater than 1 and less than n/2. Then, for each plant product of the subset of selected plant products, a level of expression of one or more infection biomarkers is determined. For the subset of selected plant products, a set of biomarker expression statistics is determined based on the determined levels of expression of the one or more infection biomarkers for each plant product of the subset. Based at least in part on the set of biomarker expression statistics determined for the subset of plant products, a likelihood of infection in the set of plant products is predicted. Finally, the predicted likelihood of infection in the set of plant products is returned.

In another aspect, the present disclosure provides another method of predicting a likelihood of infection in a set of n similarly sourced plant products, wherein n is an integer greater than 10. The method includes selecting a subset of m plant products from the set of plant products, wherein m is an integer greater than 2 and less than n/2. The m plant products of the subset are then divided into p subgroups, wherein p is an integer greater than 1 and less than m, and wherein each of the p subgroups contains at least 1 of the plant products of the subset. Next, for each of the p subgroups, plant matter from each of the plant products of the subgroup is combined to form a group of pooled plant matter, wherein the p groups of pooled plant matter form a collection of pooled plant matter groups. Next, for the collection of pooled plant matter groups, a set of biomarker expression statistics is determined based on the determined levels of expression of the one or more infection biomarkers for each pooled plant matter group of the collection of plant matter groups. Based at least in part on the set of biomarker expression statistics determined for the collection of pooled plant matter groups, a likelihood of infection in the set of plant products is predicted. Finally, the predicted likelihood of infection in the set of plant products is returned.

Any of the methods described herein can include one or more of the following steps or features, either alone or in combination with one another. The method can further include determining a level of expression of one or more housekeeping biomarkers for each plant product of the subset or for each of the pooled plant matter groups, wherein the set of biomarker expression statistics for the subset of plant products or for the collection of pooled plant matter groups is determined based at least on the level of expression of the one or more infection biomarkers and the level of expression of the one or more housekeeping biomarkers for each plant product of the subset or for each of the pooled plant matter groups. The one or more infection biomarkers can be selected from Table 1. The one or more housekeeping biomarkers can be selected from Table 2. Each biomarker can be a small molecule, and the level of expression of each biomarker can include or be a quantified amount of the corresponding small molecule.

The likelihood of infection in the set of plant products can be predicted by a machine-learned infection prediction model. The machine-learned infection prediction model comprises a plurality of parameters and a function. The function that in part comprises the machine-learned infection prediction model represents a relationship between a set of biomarker expression statistics for the subset of plant products or for the collection of pooled plant matter groups received as an input to the machine-learned infection prediction model, and a predicted likelihood of infection in the set of plant products generated as an output of the machine-learned infection prediction model.

Prior to use of the machine-learned infection prediction model for prediction of the likelihood of infection in the set of plant products, the parameters of the machine-learned infection prediction model are learned during one or more training phases. Specifically, during training, the parameters of the infection prediction model are identified based at least in part on a training data set that includes a plurality of training samples. Each training sample in the training data set is associated with a retrospective set of similarly sourced plant products, and includes a set of biomarker expression statistics for a subset of plant products or for a collection of pooled plant matter groups from the retrospective set of similarly sourced plant products. As described above, the set of biomarker expression statistics is based on levels of expression of the one or more infection biomarkers and optionally on the levels of expression of one or more housekeeping biomarkers for each plant product of the subset of plant products or each pooled plant matter group of the collection of pooled plant matter groups from the retrospective set of plant products. Additionally, each training sample in the training data set further comprises an actual, known rate of infection in the retrospective set of plant products. Training of the infection prediction model using a training data set is discussed in further detail below.

Following training and, in some implementations, validation of the machine-learned infection prediction model, the infection prediction model can be used as mentioned above to predict the likelihood of infection in the set of plant products. To predict the likelihood of infection in the set of plant products, the set of biomarker expression statistics determined for the subset of plant products or for the collection of pooled plant matter groups is input into the machine-learned infection prediction model. Then, a predicted likelihood of infection in the set of plant products is output by the machine-learned infection prediction model based at least in part on the set of biomarker expression statistics for the subset of plant products or for the collection of pooled plant matter groups and the plurality of parameters identified during training at least based on the training data set.

In implementations in which the likelihood of infection in the set of similarly sourced plant products is predicted by the machine-learned infection prediction system, the function of the machine-learned infection prediction system can include one or more of a binary logistic regression model, logistic model tree, logistic model regressor, random forest classifier, logistic model regressor, L2 regularization, partial least squares classification, Naïve Bayes classifier, multivariate spines, one or more neural networks, and k-nearest neighbor classification. In implementations in which the function of the machine-learned infection prediction model comprises one of a k-nearest neighbor classification and a random forest classifier, the machine-learned infection prediction model is able to predict a likelihood of infection in a set of plant products to be greater than a threshold of at least 5% (for example, at least 10%, 15%, 20%, 25%, 30%, 35%, 40%, 45%, 50%, 55%, 60%, 65%, 70%, 75%, 80%, 85%, 90%, or 95%) with one of at least 90% accuracy, at least 80% recall, and at least 80% precision.

Determining the set of biomarker expression statistics for the subset of plant products can include, for each plant product of subset of plant products or each pooled plant matter group of the collection of pooled plant matter groups, determining a normalized level of expression of the one or more infection biomarkers and determining a feature-scaled level of expression of the one or more infection biomarkers. The normalized level of expression of the one or more infection biomarkers for a plant product or for a pooled plant matter group can be based on the levels of expression of the one or more infection biomarkers and optionally also on the levels of expression of the one or more housekeeping biomarkers. For example, in some implementations, determining the normalized level of expression of the one or more infection biomarkers for a plant product or for a pooled plant matter group can comprise determining a ratio of the level of expression of the one or more infection biomarkers to the level of expression of the one or more housekeeping biomarkers. The feature-scaled level of expression of the one or more infection biomarkers for a plant product or for a pooled plant matter group is in turn based on the normalized level of expression of the one or more infection biomarkers for the plant product or for the pooled plant matter group. In some implementations, determining the feature-scaled level of expression of the one or more infection biomarkers for a plant product or for a pooled plant matter group can comprise performing at least one of a min-max normalization$^6$ and a log transformation of the normalized level of expression of the one or more infection biomarkers for the plant product or the pooled plant matter group.

The set of biomarkers expression statistics for the subset of plant products or for the collection of pooled plant matter groups can be based on the feature-scaled level of expression of the one or more infection biomarkers for each plant product in the subset or for each pooled plant matter group in the collection of pooled plant matter groups. For example, in some implementations, the set of biomarker expression statistics for the subset of plant products or for the collection of pooled plant matter groups is determined by determining at least one of a mean, median, minimum, maximum, standard deviation, $5^{th}$ percentile, $10^{th}$ percentile, 15th percentile, 20th percentile, 25th percentile, $50^{th}$ percentile, 75th percentile, $80^{th}$ percentile, 90th percentile, $95^{th}$ percentile and $99^{th}$ percentile of the feature-scaled levels of expression of the one or more infection biomarkers for the plant products of the subset of plant products or for the pooled plant matter groups of the collection of pooled plant matter groups, and a ratio of the feature-scaled level of expression of at least one of the one or more infection biomarkers to the feature-scaled level of expression of at least one other of the one or more infection biomarkers for each plant product in the subset of plant products or for each pooled plant matter group and/or a product of the feature-scaled level of expression of at least one of the one or more infection biomarkers and the feature-scaled level of expression of at least one other of the one or more infection biomarkers for each plant product in the subset of plant products or each pooled plant matter group in the collection of pooled plant matter groups.

In certain implementations, the infection comprises a fungal infection. In such implementations, the fungal infection can be caused by one or more pathogens selected from the group consisting of the genus *Colletotrichum* (i.e. *C. gloeosporioides*, *C. acutatum*), *Dothiorella* (i.e. *D. iberica*, *D. gregaria*, *D. aromatica*), *Neofusicoccum* (i.e. *N. luteum*, *N. parvum*, *N. australe*), *Diaporthe* (i.e. *D. neotheicola*, *D. cinnamomi*), *Lasiodiplodia* (i.e. *L. pseudotheobromae*, *L. theobromae*), *Diplodia* (i.e. *D. mutila*, *D. pseuodoseriata*, *D. seriata*), and the family *Botryosphaeria*, (i.e. *B. dothidea*). The infection can, for example, manifest as stem-end rot, mold, and/or vascular/internal browning, among others.

The set of similarly sourced plant products in which the likelihood of infection is predicted can be harvested or un-harvested plant products. Furthermore, the set of similarly sourced plant products in which the likelihood of infection is predicted can be ripe or unripe plant products. In some cases, the plant products present no visible symptoms of infection. The plant products can, for example, include avocados, pomegranates, persimmons, apples, pears, grapes, citrus fruits, papaya, cherries, melons, guava, mangoes, or stone fruits, among others.

To determine a level of expression of a biomarker in a plant product, material can be extracted from one or more of the exocarp, endocarp and mesocarp of the plant product, and biomarker analysis can be performed on the extracted material to determine the level of expression of the biomarker. Furthermore, determination of a level of expression of a biomarker can, for example, be determined by performing one or more analyses selected from the group consisting of qPCR, PCR, RT-PCR, ribonucleic acid (RNA) sequencing (RNA-seq), Tag-seq, assay for transposase-accessible chromatin using sequencing (ATAC-seq), CyTOF/SCoP, E-MS/Abseq, miRNA-seq, CITE-seq, mass spectroscopy (MS), gas chromatography in tandem to mass spectroscopy (GC-MS), comprehensive two dimensional gas chromatography (GCxGC), solid phase microextraction (SPME) in tandem to GCxGC (SPME-GCxGC), matrix assisted laser desorption/ionization (MALDI), and MALDI-TOF.

The biomarker can, for example, be a gene. In implementations in which the biomarker is a gene, a level of expression of the biomarker can correspond to a level of expression of an RNA sequence associated with the gene. In such implementations, the level of expression of the RNA sequence associated with the gene can further comprise a copy number of the RNA sequence associated with the gene.

In any of the methods disclosed herein, predicting the likelihood of infection in the set of plant products can require less than 6 hours (e.g., less than 5 hours, less than 4 hours, less than 3 hours, less than 2 hours, or less than 1 hour). Following the prediction of the likelihood of infection in the set of plant products, the predicted likelihood of infection can be returned by automatically presenting the predicted likelihood of infection to a viewing user. Furthermore, the set of similarly sourced plant products can undergo processing based on the likelihood of infection predicted for the set of similarly sourced plant products. Specifically, one or more plant products of the set of similarly sourced plant products that are at risk for infection can be identified based on the predicted likelihood of infection.

In any of the methods disclosed herein, an anti-microbial treatment can be provided to or prescribed for the set of similarly sourced plant products based on the predicted likelihood of infection. The set of similarly sourced plant products can be selectively harvested based on the predicted likelihood of infection. In any of the methods disclosed herein, a quality assurance can be determined for the set of similarly sourced plant products based on the predicted likelihood of infection. Furthermore, at least one of a consumer and a geographic destination can be identified for the set of similarly sourced plant products based on the predicted likelihood of infection. Additionally, ethylene treatment can be withheld or prescribed for the set of similarly sourced plant products based on the predicted likelihood of infection. Ethylene treatment can include, for example, the application of exogenous gaseous ethylene, the use of ethylene absorbers or the application of chemical ethylene blockers (i.e. 1-MCP). In some cases, one or more storage conditions for the set of similarly sourced plant products can be identified based on the predicted likelihood of the infection. The storage conditions can, for example, include at least one of a storage temperature and a storage humidity. Additionally, a post-harvest treatment can be provided or a dosage of post-harvest treatment can be prescribed to the set of similarly sourced plant products based on the predicted likelihood of infection. Furthermore, instructions instructing a user to perform any one of the above plant-processing methods based on the predicted likelihood of infection can be provided to the user based on the predicted likelihood of infection.

In another aspect, the present disclosure provides a non-transitory computer-readable storage medium that stores computer program instructions that, when executed by a computer processor, cause the computer processor to predict a likelihood of infection in the set of similarly sourced plant products by performing any combination of the above method steps.

One or more embodiments described herein can include a method for identifying a latent infection in a plant product. The method can include obtaining, by a processor, data describing a level of expression of one or more infection biomarkers of a plant product, the infection biomarkers indicating a likelihood of infection in the plant product, where the data identifies one or more variants that can describe differences between a read sequence of the plant product and a reference genome of a healthy plant product, encoding, by the processor, the obtained data into a data structure for input to a machine learning model, and providing, by the processor, encoded data structure as input to the machine learning model. The machine learning model can be previously trained, using data that correlates other encoded data structures and determined one or more infection biomarkers of one or more other plant products, to predict likelihoods of infection in the one or more other plant products. The machine learning model can be trained using a process that includes inputting, from a training data set, (i) a first set of training samples of infection biomarkers of the one or more other plant products and (ii) known rates of infection for the first set of training samples into the machine learning model, determining the predicted likelihoods of infection in the one or more other plant products based on inputting (i) and (ii) into the machine learning model, determining a difference between the predicted likelihoods of infection and the known rates of infection, generating, based on the determined difference, a set of parameters for validating the machine learning model, validating, using the set of parameters, the machine learning model so that the determined difference between the predicted likelihoods of infection and the known rates of infection are within a predetermined threshold range, where validating the machine learning model can include inputting a second set of training samples from the training data set into the machine learning model, and outputting the validated machine learning model for runtime use. The method can also include obtaining, by the processor and from the machine learning model, the generated output data indicating a likelihood that the plant product has a latent infection, determining, by the processor and based on the generated output data, that the plant product has a latent infection, and performing, by the processor, one or more operations to mitigate the latent infection in the plant product.

In some implementations, the embodiments described herein can optionally include one or more of the following features. For example, the machine learning model can include one or more of a binary logistic regression model, logistic model tree, random forest classifier, L2 regularization, partial least squares, Naiive Bayes classifier, multivariate adaptive regression spines, convolutional neural networks (CNNs), and k-nearest neighbor classification. The plant product may not include any visible signs of an infection.

As another example, the method can also include selecting, by the processor, a subset of m plant products from the set of plant products, wherein m is an integer greater than 1 and less than n/2, and for each plant product of the subset, determining, by the processor, a level of expression of one or more infection biomarkers. Obtaining, by the processor, data describing a level of expression of one or more biomarkers in a plant product can include obtaining, for each plant product of the subset, data describing the determined level of expression of the one or more infection biomarkers. Encoding, by the processor, the obtained data into a data structure for input to a machine learning model can include encoding the obtained data describing the determined level of expression of the one or more infection biomarkers into one or more data structures for input to the machine learning model.

As another example, the set of parameters can be generated using at least one of gradient-based numerical optimization, batch gradient analysis, and stochastic gradient analysis. In some implementations, the method can also include providing, by the processor, encoded data structure as input to multiple machine learning models. The multiple machine learning models can be previously trained, using data that can correlate other encoded data structures and determined one or more infection biomarkers of one or more other plant products, to predict likelihoods of infection in the one or more other plant products. In some implementations, each of the multiple machine learning models can be previously trained to predict likelihood of a particular type of infection in the one or more other plant products.

As yet another example, the method can also include training, by the processor, the machine learning model with the output data indicating the likelihood that the plant product has a latent infection that was generated by the machine learning model during runtime. In some implementations, the method can include performing, by the processor, one or more operations to mitigate the latent infection in the plant product that can include identifying, based on the generated output data, a set of similarly sourced plant products that is at risk of developing the latent infection. In some implementations, performing, by the processor, one or more operations to mitigate the latent infection in the plant product can include determining a quantity of anti-microbial treatment to apply to the plant product.

One or more embodiments described herein can also include a system for identifying a latent infection in a plant product, the system having at least one processor and a memory device that can store instructions that can be operable, when executed by the at least one processor one or more computers, to cause the at least one processor to perform operations that include the methods described herein. In some implementations, the system can include one or more of the abovementioned features.

One or more embodiments described herein can also include a non-transitory computer-readable medium storing instructions stored thereon that, when executed by at least one processor of a computing device, can cause the at least one processor of the computing device to perform operations that include the methods described herein. In some implementations, the non-transitory computer-readable medium can include one or more of the abovementioned features.

In another aspect, the present disclosure can include a method for identifying a latent infection in a plant product. In some implementations, the method can include operations of obtaining, by one or more computers, data describing a level of expression of one or more infection biomarkers in a plant product, encoding, by the one or more computers, the obtained data into a data structure for input to a machine learning model, providing, by the one or more computers, encoded data structure as in input to the machine learning model that has been trained to generate output data indicating a likelihood that the plant product has a latent infection based on processing the encoded data structure, obtaining, by the one or more computers, the generated output data indicating a likelihood that the plant product has a latent infection, determining, by the one or more computers and based on the generated output data, that the plant product has a latent infection, and performing, by the one or more computers, one or more operations to mitigate the latent infection in the plant product.

Other aspects include corresponding systems, apparatus, and computer programs to perform the actions of methods as disclosed herein as defined by instructions encoded on computer readable storage devices.

These and other aspects may optionally include one or more of the following features. In some implementations, performing, by the one or more computers, the one or more operations to mitigate the latent infection in the plant product can include determining, by the one or more computers and based on the output data, that an anti-microbial treatment is to be prescribed for one or more other similarly sourced plant products.

In some implementations, performing, by the one or more computers, the one or more operations to mitigate the latent infection in the plant product can include administering, by the one or more computers and based on the output data, an anti-microbial treatment to one or more other similarly sourced plant products.

In some implementations, performing, by the one or more computers, the one or more operations to mitigate the latent infection in the plant product can include determining, by the one or more computers and based on the output data, that a vehicle that is transporting one or more other similarly sourced plant products is to be re-routed to a different destination.

In some implementations, performing, by the one or more computers, the one or more operations to mitigate the latent infection in the plant product can include generating, by the one or more computers and based on the output data, an alert message that, when processed by a user device, causes the user device to output an alert that notifies a user of the user device that the vehicle is to be re-routed to a different destination, and transmitting, by the one or more computers, the generated alert to the user device.

In some implementations, performing, by the one or more computers, the one or more operations to mitigate the latent infection in the plant product can include generating, based on the output data and based on the output data, an alert message that, when processed by a user device, cause the user device to output an alert that notifies a user of the user device that one or more other similarly sourced plant products, and transmitting, by the one or more computers, the alert message to the user device.

In some implementations, the data describing a level of expression of one or more infection biomarkers in a plant product can include a list of one or more variants, wherein the one or more variants describe differences between a read sequence of the plant product and a reference genome of a healthy plant product.

In some implementations, the machine learning model can include one or more of a binary logistic regression model, logistic model tree, random forest classifier, L2 regularization, partial least squares.

In some implementations, the plant product does not include any visible signs of an infection.

In some implementations, the method can include selecting, by the one or more computers, a subset of m plant products from the set of plant products, wherein m is an integer greater than 1 and less than n/2, and for each plant product of the subset, determining, by the one or more computers a level of expression of one or more infection biomarkers. In such implementations, obtaining, by one or more computers, data describing a level of expression of one or more biomarkers in a plant product can include obtaining, by the one or more computers and for each plant product of the subset, data describing the determined level of expression of the one or more infection biomarkers. Likewise, in such implementations, encoding, by the one or more computers, the obtained data into a data structure for input to a machine learning model can include encoding, by the one or more computers, the obtained data describing the determined level of expression of the one or more infection biomarkers into one or more data structures for input to the machine learning model.

BRIEF DESCRIPTION OF THE DRAWINGS

These and other features, aspects, and advantages of the present invention will become better understood with regard to the following description, and accompanying drawings, where:

FIG. 10B is a block diagram of an exemplar data pipeline for training, validating, and testing an infection prediction system configured to predict whether a set of similarly sourced plant products has a likelihood of infection of greater than or less than 5%.

DETAILED DESCRIPTION

Figure 1:
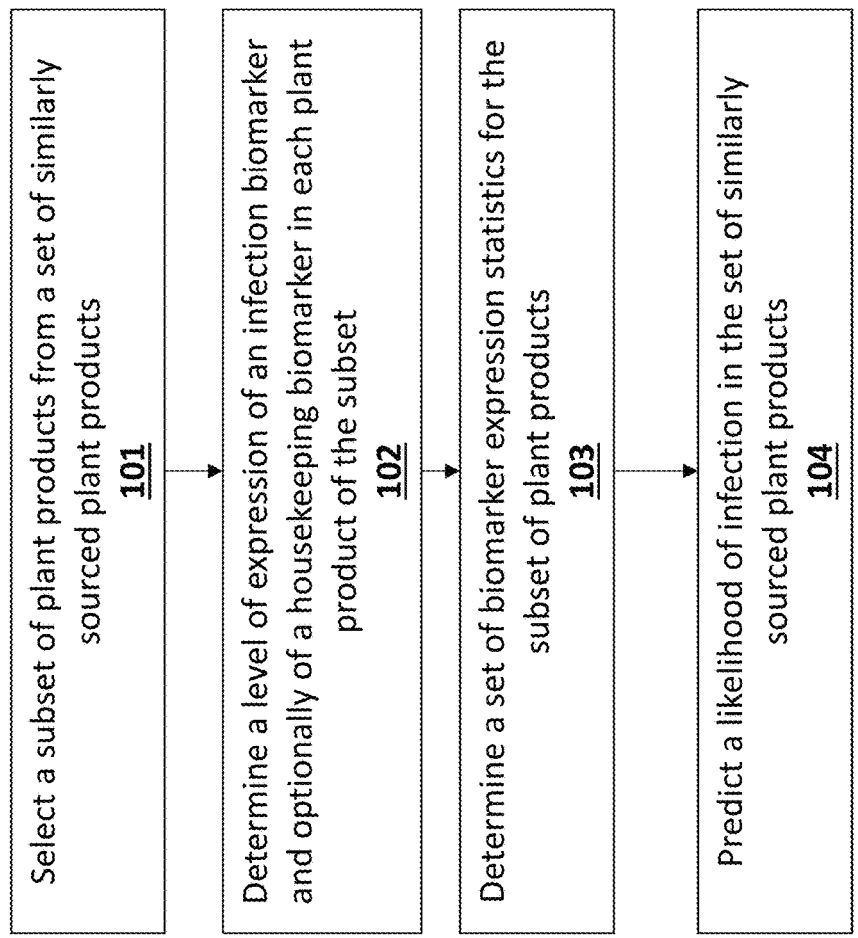
FIG. 1 is a flow chart of a method for predicting a likelihood of infection in a set of similarly sourced plant products.

The present disclosure is directed to a systems, methods, and computer programs for detecting latent infections in plants. In one aspect, the present disclosure is directed to a trained machine learning model that can generate output data that is indicative of a likelihood that a plant product has a latent infection based on the machine learning model's processing of input data representing features of the plant product. In some implementations, the features of the plant product can include data representing a level of expression of one or more biomarkers detected within the plant product sample. If the present disclosure determines, based on the generated output data, that the plant product has a latent infection, the present disclosure can cause performance of one or more operations designed to mitigate the detected latent infection.

The present disclosure provides multiple technical advantages. For example, in some implementations, the present disclosure can reduce the amount of the plant product that needs to be destroyed to detect latent infection in a similarly sourced set of plant products by only sampling a subset of the similarity sourced set of plant products. In these, or other implementations, the present disclosure also provides the benefit of saving plant products by detecting the latent infection and initiating one or more remedial measures to mitigate, and even eliminate, the latent infection before it manifests, thus allowing for the plant product to be sold. This provides a significant economic benefit to users of the present disclosure. These and other advantages are readily apparent from the disclosure herein.

I. Definitions

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

Any terms not directly defined herein shall be understood to have the meanings commonly associated with them as understood within the art of the present disclosure. Certain terms are discussed herein to provide additional guidance to the practitioner in describing the compositions, devices, methods and the like of aspects of the present disclosure, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the present disclosure herein.

As referred to herein, the term "plant product" refers to any product produced by a plant. Plant products include, for example, fruits, vegetables, seeds, flowers, tubers, bulbs, and any other product of a plant. For example, in some implementations, a plant product may comprise an avocado, pomegranate, persimmon, apple, pear, grape, citrus fruit, papaya, cherry, melon, guava, mango, or stone fruit.

As mentioned above, this disclosure discusses prediction of infection in a set of similarly sourced plant products. A set of similarly sourced plant products includes multiple (i.e., more than one) plant products. As briefly mentioned above, the term "similarly sourced" with regard to plant products refers to multiple plant products that have been located in the same geographic area. The bounds of the geographic area may vary. For example, as discussed above, a set of similarly sourced plant products may include plant products grown in the same orchard. In another example, a set of similarly sourced plant products can comprise a set of plant products that were transported on the same truck. In yet another example, a set of similarly sourced plant products may include plant products sold in the same grocery store. In another example, a set of similarly sourced plant products can comprise a set of plant products that belong to the same commercial lot. The basis for this geographic definition of similarly sourced plant products is to group plant products together that are capable of infliction with the same infection, either pre-harvest or post-harvest of the plant products.

As referred to herein, the term "subset" with regard to the sampling of plant products from the similarly sourced set of n plant products, wherein n is an integer greater than 10, refers to a representative sample of m plant products wherein m is an integer greater than 1 and less than n/2. This subset is randomly selected from the set of plant products such that measured biomarkers statistics of the subset are generalizable to the set.

As used herein, the term "plant matter" refers to any portion of a plant, including, for example, fruits (in the botanical sense, including fruit peels and juice sacs), vegetables, leaves, stems, barks, seeds, flowers, peels, nuts, kernels, flesh, or roots. Plant matter includes pre-harvest plants or portions thereof as well as post-harvest plants or portions thereof, including, e.g., harvested fruits and vegetables, harvested roots and berries, and picked flowers.

As referred to herein, the term "infection" with regard to a plant product refers to any pathogenic infection present in the plant product. In some implementations, a plant product infection can be a latent infection such that the infected plant product presents no visible symptoms of infection. In alternative implementations, a plant product infection can manifest with visible symptoms, including those discussed below.

Plant product infections can be caused by any pathogen and can include, for example, bacterial infections, viral infections, fungal infections, and oomycete infections or any combination thereof. In implementations in which a plant product infection comprises a fungal infection, the fungal infection can, for example, be caused by a pathogen selected from the group consisting of the genus *Colletotrichum* (i.e. *C. gloeosporioides, C. acutatum*), *Dothiorella* (i.e. *D. iberica, D. gregaria, D. aromatica*), *Neofusicoccum* (i.e. *N. luteum, N. parvum, N. australe*), *Diaporthe* (i.e. *D. neotheicola, D. cinnamomi*), *Lasiodiplodia* (i.e. *L. pseudotheobromae, L. theobromae*), *Diplodia* (i.e. *D. mutila, D. pseuodoseriata, D. seriata*), and family *Botryosphaeria*, (i.e. *B. dothidea*) and any other fungal pathogen.

Plant product infections can manifest in any capacity. For example, in some implementations, a plant product infection can manifest as stem-end rot, mold, and/or vascular/internal browning. As a specific example, in some implementations, infection can manifest in avocados, apples, pears, and/or stone fruits as vascular/internal browning. As another example, in some implementations, infection can manifest in avocadoes and/or mangoes as stem rot.

As discussed above, a plant product infection can be a latent infection, such that the infected plant product presents no visible symptoms of infection for an extended period. At the end of this latent period, the plant product infection may manifest as one of stem-end rot, mold, and/or vascular/internal browning. As a specific example, in some implementations, latent infections of fungi from the genus *Colletotrichum* can manifest in avocadoes and/or mangoes as stem rot.

As referred to herein, the term "likelihood of infection" with regard to one or more plant products refers to a prediction of a likelihood of infection in the one or more plant products. In contrast, as referred to herein, the term "rate of infection" with regard to one or more plant products refers to the actual, known incidence of infection in the one or more plant products. As discussed in further detail below, rates of infection in plant products can be used in part to train an infection prediction model to predict likelihoods of infection in other plant products.

For any implementations described herein, the likelihood of infection of plant products can be predicted for a set of similarly-sourced plant products at any stage in the lifecycle of the plant products. For example, a likelihood of infection can be predicted for a set of harvested or unharvested plant products. As another example, a likelihood of infection can be predicted for a set of ripe or unripe plant products. Prediction of infection for unripe plant products can be particularly useful because oftentimes infection is latent in unripe plant products, and cannot be visually detected until after the plant products ripen. Therefore, prediction of infection in unripe plant products can expose infection before it is visually detectable.

As referred to herein, the term "biomarker" with regard to a plant product refers to any molecule present in the plant product. For example, a biomarker may comprise a nucleic acid, including DNA, modified (e.g., methylated) DNA, cDNA, and RNA, including coding (e.g., mRNAs, tRNAs) and non-coding RNA (e.g., sncRNAs, miRNAs, piRNAs, lncRNAs), a protein, including a post-transcriptionally modified protein (e.g., phosphorylated, glycosylated, myristilated, etc. proteins), a nucleotide (e.g., adenosine triphosphate (ATP), adenosine diphosphate (ADP), and adenosine monophosphate (AMP)), including cyclic nucleotides such as cyclic adenosine monophosphate (cAMP) and cyclic guanosine monophosphate (cGMP), a biologic, an ADC, a small molecule, such as oxidized and reduced forms of nicotinamide adenine dinucleotide (NADP/NADPH), a volatile compound, and any combination thereof.

As referred to herein, the term "level of expression" with regard to a biomarker refers to a measure of any substance that serves as a proxy for expression of the biomarker. The measure can be quantitative, qualitative, absolute, and/or relative. For example, in an implementation in which a biomarker comprises a gene, a level of expression of the biomarker can comprise a quantification of RNA transcripts associated with the gene. Determination of levels of biomarker expression is discussed in further detail below.

As used herein, the term "infection biomarker" refers to any biomarker suitable for predicting a likelihood of infection in plant products, including biomarkers that have been determined to be differentially expressed in infected plant products compared to uninfected plant products. In other words, infection biomarkers suitable for predicting a likelihood of infection in plant products include biomarkers that have been determined to be correlated with infection in plant products. Infection biomarkers can, for example, include biomarkers that are differentially expressed by a threshold percentage in infected plant products compared to uninfected plant products. For instance, infection biomarkers can include biomarkers that have been determined to be differentially expressed in infected plant products compared to uninfected plant products by at least 0.1 fold change (for example, at least 0.2, 0.3, 0.4, 0.5, 0.6, 0.7, 0.8, 0.9, 1, 2, 3, 4, 5, 10, or 20 fold change). Table 1 contains a list of exemplary infection biomarkers.

As used herein, a "housekeeping biomarker" refers to a biomarker suitable in a plant product that has been determined to not be correlated with infection in plant products. In other words, housekeeping biomarker expression is uniform (e.g., exhibits less than 0.5, 0.4, 0.3, 0.2, or 0.1 fold change) across both infected and uninfected plant products. Table 2 contains a list of exemplary housekeeping biomarkers.

As used herein, the term "ethylene treatment" with regard to plant products refers to the application or use of any product which alters or aims to alter the ethylene composition, consumption or detection in post-harvest plant products. In some implementations, an ethylene treatment includes the application of exogenous, gaseous ethylene to plant products post-harvest to alter or control the ripening rate. In other implementations, an ethylene treatment includes the use or application of an ethylene inhibitor, blocker or absorber (e.g., 1-methylcycloprene, herein "1-MCP") to plant products post-harvest to control the ripening rate or prolong the shelf-life of the plant products.

II. Method Overview

FIG. 1 is a flow chart of an exemplary method 100 for predicting a likelihood of infection in a set of similarly sourced plant products. In some implementations, the set of similarly sourced plant products more than a threshold number of plant products. For example, in some implementations, the threshold number of plant products may be greater than 10 plant products. However, the present disclosure is not limited such a threshold number and the set of similarly sourced plant products can include more or less than 10 plant products. Although certain steps are shown to occur in a specific order, steps of the method can in some cases be performed in different orders than that described in conjunction with FIG. 1. Furthermore, in some cases certain steps may be omitted and/or substituted by other steps, and/or additional steps may be added.

To predict a likelihood of infection in a set of similarly sourced plant products, as shown in FIG. 1, a subset of plant products is selected 101 from the set of similarly sourced plant products. The subset typically includes at least 2 plant products and less than half of the total number of products in the set of similarly sourced plant products. Selection 101 of a subset of plant products from a set of similarly sourced plant products is discussed in further detail below with regard to FIG. 2A.

A level of expression of at least one infection biomarker and optionally at least one housekeeping biomarker is determined 102 for each plant product of the selected subset of plant products. Identification of infection biomarkers and housekeeping biomarkers suitable for predicting a likelihood of infection in plant products is discussed in further detail below. However, briefly, infection biomarkers suitable for predicting a likelihood of infection in plant products include biomarkers that have been determined to be differentially expressed in infected plant products compared to uninfected plant products. In other words, infection biomarkers suitable for predicting a likelihood of infection in plant products include biomarkers that have been determined to be correlated with infection in plant products. In a preferred implementation, infection biomarkers include biomarkers that are differentially expressed by a threshold percentage in infected plant products compared to uninfected plant products. For instance, infection biomarkers can include biomarkers that have been determined to be differentially expressed in infected plant products compared to uninfected plant products by at least 0.1 fold change (for example, at least 0.2, 0.3, 0.4, 0.5, 0.6, 0.7, 0.8, 0.9, 1, 2, 3, 4, 5, 10, or 20 fold change).

Housekeeping biomarkers suitable for predicting a likelihood of infection in plant products include biomarkers that have been determined to not be correlated with infection in plant products. In other words, housekeeping biomarker expression is uniform (e.g., exhibit less than 0.5, 0.4, 0.3, 0.2, or 0.1 fold change) across both infected and uninfected plant products. As discussed in detail below, housekeeping biomarker expression can be used to normalize infection biomarker expression between infected and uninfected plant products.

In some implementations, levels of biomarker expression in a plant product can be determined by testing the plant product using an array and/or kit configured to detect the levels of biomarker expression in the plant product. In some further implementations, determining levels of biomarker expression in a plant product can also include preparing the plant product for biomarker analysis. For example, determining levels of biomarker expression in a plant product can include extracting material from the plant products for biomarker analysis. Preparation of plant products for biomarker analysis is discussed in detail below.

Next, a set of biomarker expression statistics for the subset of plant products is determined 103 based on the determined levels of expression of at least one infection biomarker and optionally of at least one housekeeping biomarker for each plant product in the subset. As discussed in detail below with regard to FIG. 2C, in some implementations, the set of biomarker expression statistics for the subset of plant products is determined based on a feature-scaled expression level of the at least one infection biomarker for each plant product in the subset of plant products, which is in turn determined based on a normalized level of expression of the at least one infection biomarker for each plant product in the subset of plant products. Furthermore, as discussed in detail below with regard to FIG. 2D, the set of biomarker expression statistics for the subset of plant products can include at least one of a mean, median, minimum, maximum, standard deviation, $5^{th}$ percentile, $10^{th}$ percentile, $15^{th}$ percentile, $20^{th}$ percentile, $25^{th}$ percentile, $50^{th}$ percentile, $75^{th}$ percentile, $80^{th}$ percentile, $90^{th}$ percentile, $95^{th}$ percentile and $99^{th}$ percentile of the feature-scaled levels of expression of the at least one infection biomarker, a ratio of the feature-scaled level of expression of at least one of the at least one infection biomarker to the feature-scaled level of expression of at least one other of at least one infection biomarker for each plant product of the subset of plant products, and a product of the feature-scaled level of expression of at least one of the at least one infection biomarker and the feature-scaled level of expression of at least one other of at least one infection biomarker for each plant product of the subset of plant products.

Finally, a likelihood of infection in the set of similarly sourced plant products is predicted 104 based at least in part on the determined set of biomarker expression statistics for the subset of plant products. In some implementations, as discussed in detail below with regard to FIGS. 3-5D, the likelihood of infection in the set of similarly sourced plant products can be predicted based at least in part on the determined set of biomarker expression statistics for the subset of plant products using a machine-learned infection prediction system. In certain implementations, prediction of the likelihood of infection in the set of similarly sourced plant products can be completed in less than 6 hours.

The predicted likelihood of infection in the set of similarly sourced plant products can then be returned, and in some implementations, leveraged to deliberately process the set of similarly sourced plant products. For example, a predicted likelihood of latent infection in a set of similarly sourced plant products can be used to determine when and where to sell the set of plant products. Additional implementations of plant product processing based on infection prediction are discussed in detail below.

III. Selection of Plant Products for Biomarker Analysis

Figure 2A:
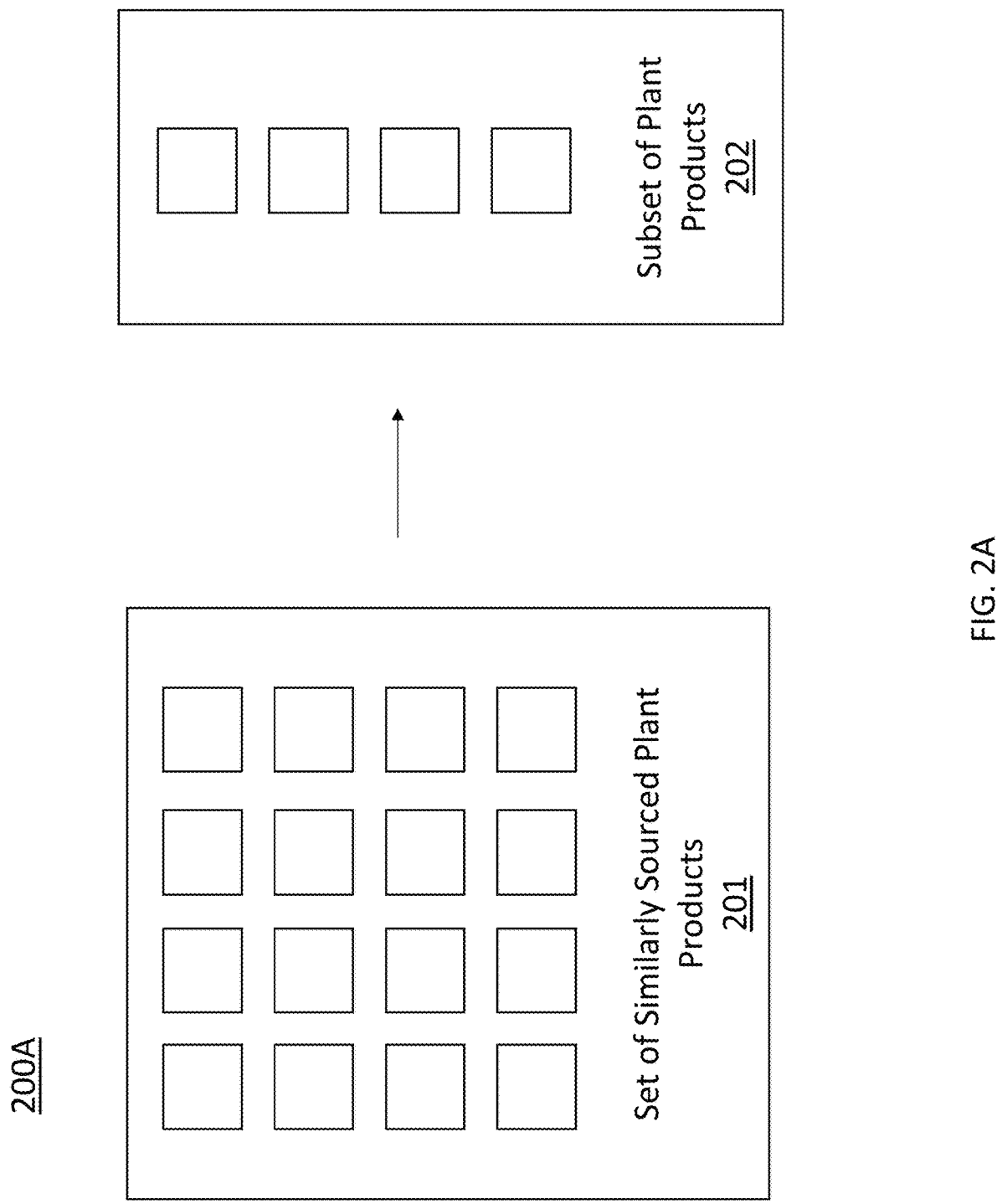
FIG. 2A is a block diagram of a system environment in which a subset of plant products is selected from a set of plant products for use in prediction of a likelihood of infection in the set of plant products.

Turning to FIG. 2A, FIG. 2A is a block diagram 200A of an exemplary system environment in which a subset of plant products 202 is selected from a set of plant products 201 for use in prediction of a likelihood of infection in the set of plant products 201.

In some implementations, a set of similarly sourced plant products comprises a total of n plant products, where n is an integer greater than 10. For example, as shown in FIG. 2A, the set of plant products 201 for which a likelihood of infection is to be predicted comprises 16 individual plant products, each individual plant product represented by a square. However, in alternative implementations, a set of similarly sourced plant products can comprise any quantity of individual plant products.

In further implementations, a subset of plant products selected from the set of similarly sourced plant products can comprise m plant products, where m is an integer greater than 1 and less than n/2. In some implementations, a subset of plant products selected from the set of similarly sourced plant products can be randomly selected. For example, as shown in FIG. 2A, the subset of plant products 202 is randomly selected from the set of similarly sourced plant products 201 and comprises 4 individual plant products. However, in alternative implementations, a subset of plant products selected from a set of similarly sourced plant products can comprise any quantity of individual plant products.

By analyzing a representative subset of m plant products 202 from a set of similarly sourced n plant products 201 (where m is greater than 1 and less than n/2) to predict a likelihood of infection in the entire set of n plant products, less time and resources are required to predict infection in the set of n plant products. For example, by analyzing a subset of m plant products, fewer plant products are scarified to make this prediction, thereby enabling higher product quality, but still at higher product yield.

IV. Preparation of Plant Products for Biomarker Analysis

As alluded to above, after a subset of plant products is selected from the set of similarly sourced plant products, expression of infection biomarkers and optionally housekeeping biomarkers in each individual plant product of the subset of plant products is determined to predict a likelihood of infection in the set of plant products. However, as also alluded to above, in some cases, prior to determining levels of biomarker expression in each plant product in the subset, each plant product of the subset is prepared for biomarker analysis.

Preparation of a plant product for biomarker analysis can depend upon the specific biomarker to be measured. Depending on the specific biomarker to be measured, biomarker expression in a plant product can be determined according to many different methods. For instance, biomarker expression can be measured by polymerase chain reaction (PCR), quantitative polymerase chain reaction (qPCR), reverse transcription polymerase chain reaction (RT-PCR), reverse transcription quantitative polymerase chain reaction (RT-qPCR), ribonucleic acid (RNA) sequencing (RNA-seq), Tag-seq, assay for transposase-accessible chromatin using sequencing (ATAC-seq), CyTOF/SCoP, E-MS/Abseq, miRNA-seq, CITE-seq, mass spectroscopy (MS), gas chromatography in tandem to mass spectroscopy (GC-MS), comprehensive two dimensional gas chromatography (GCxGC), solid phase microextraction (SPME) in tandem to GCxGC (SPME-GCxGC), matrix assisted laser desorption/ionization (MALDI), MALDI-TOF, and any combinations thereof. The method of measurement can be selected based on the biomarker to be measured. For instance, PCR and qPCR measure DNA expression. RT-PCR, RT-qPCR, RNA-seq, Tag-seq, and miRNA-seq measure RNA expression. Specifically, RT-PCR, RT-qPCR, and RNA-seq measure expression of RNA transcripts, Tag-seq allows detection of rare mRNA species, and miRNA-seq measures expression of micro-RNAs. CyTOF/SCoP and E-MS/Abseq measure protein expression. CITE-seq simultaneously measures both nucleic acid expression and protein expression. And ATAC-seq measures chromatin conformation.

A plant product can be prepared for biomarker analysis according to the biomarker being measured, and according to the method of biomarker measurement. More specifically, material (e.g., plant matter) can be extracted from a plant product for biomarker measurement based on the target biomarker and the target biomarker measurement method. For example, in the case in which a biomarker comprises a gene and RT-qPCR is used to quantify RNA expression of the gene in a plant product, RNA can be extracted from the plant product using one or more RNA extraction methods prior to sequencing using RT-qPCR.

Furthermore, depending upon the type of plant product undergoing biomarker analysis, the plant matter material can be extracted from a particular portion of the plant product for biomarker measurement. For example, in some implementations, the material can be extracted from one or more of the exocarp, mesocarp and endocarp of the plant product for biomarker measurement.

V. Biomarker Analysis of Plant Products

Figure 2B:
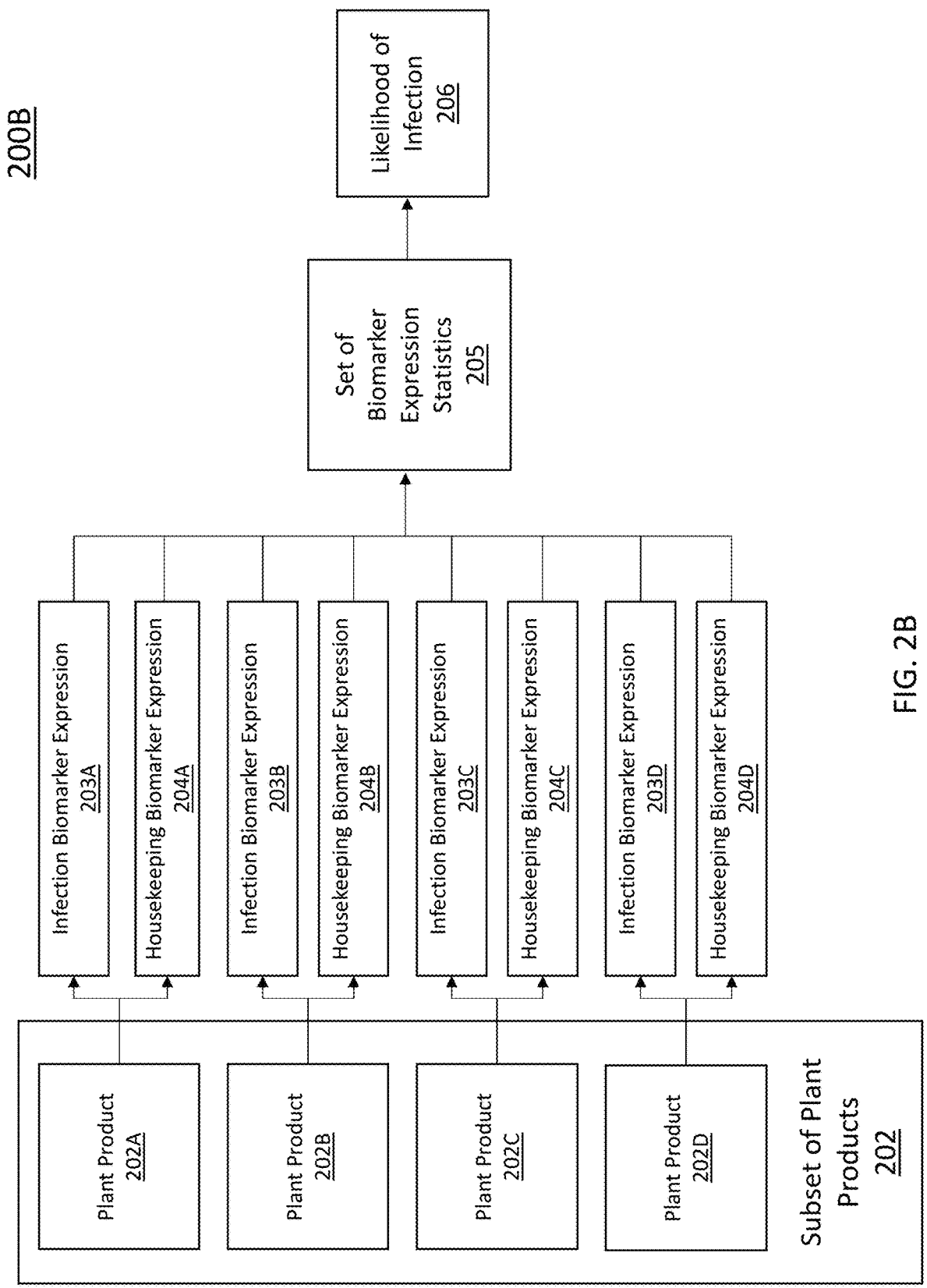
FIG. 2B is a block diagram of a system environment in which a likelihood of infection is predicted for a set of similarly sourced plant products.

Turning next to FIG. 2B, FIG. 2B is a block diagram of a system environment 200B in which a likelihood of infection 206 is predicted for a set of similarly sourced plant products. FIG. 2B is an extension of FIG. 2A. Specifically, the subset of plant products 202 depicted in FIG. 2B is the subset of plant products 202 selected from the set of similarly sourced plant products 201 in FIG. 2A. Thus, FIG. 2B is a block diagram of a system environment 200B in which a likelihood of infection 206 is predicted for the set of similarly sourced plant products 201 of FIG. 2A.

As shown in FIG. 2B, for clarity, each individual plant product of the subset of plant products 202 is labeled as one of plant product 202A, plant product 202B, plant product 202C, and plant product 202D. Furthermore, a level of expression of at least one infection biomarker and optionally a level of expression of at least one housekeeping biomarker are determined for each plant product in the subset of plant products 202. Specifically, infection biomarker expression 203A and optional housekeeping biomarker expression 204A are determined for the plant product 202A, infection biomarker expression 203B and optional housekeeping biomarker expression 204B are determined for the plant product 202B, infection biomarker expression 203C and optional housekeeping biomarker expression 204C are determined for the plant product 202C, and infection biomarker expression 203D and optional housekeeping biomarker expression 204D are determined for the plant product 202D.

As briefly discussed above, expression of a biomarker can be determined by measuring any substance that serves as a proxy for expression of the biomarker, according to any measurement method. For example, when the biomarker comprises a gene, a copy number of RNA transcripts of the gene can be a proxy for expression of the gene, and RT-qPCR can be used to quantify the copy number of the RNA transcripts of the gene. In some further implementations, biomarker expression can be determined using an array and/or kit configured to detect the biomarker expression. Thus, levels of expression of at least one infection biomarker and optionally at least one housekeeping biomarker for each plant product 202A-D of the subset of plant products 202 are determined by measuring any substance that serves as a proxy for expression of the biomarker, using any suitable measurement method. Identification of the at least one infection biomarker and optionally the at least one housekeeping biomarker for which expression levels are measured in each plant product are discussed in detail below.

Turning briefly back to the example in FIG. 2B, following determination of infection biomarker expression 203A-D and optionally of housekeeping biomarker expression 204A-D for plant products 202A-D, a set of biomarker expression statistics 205 for the subset of plant products 202 is determined based on the infection biomarker expression 203A-D and optionally the housekeeping biomarker expression 204A-D for each plant product 202A-D in the subset of plant products 202. As mentioned above, determination of the set of biomarker expression statistics 205 for the subset of plant products 202 is discussed in detail below with regard to FIGS. 2C-2D.

Finally, as shown in FIG. 2B, a likelihood of infection 206 is predicted for the set of similarly sourced plant products 201 of FIG. 2A, based at least in part on the set of biomarker expression statistics 205 determined for the subset of plant products 202. As mentioned above, prediction of the likelihood of infection 206 is discussed in further detail below with regard to FIGS. 3-5D.

Biomarker expression data (e.g., levels of biomarker expression) for a subset of a set of plant products, a set of biomarker expression statistics for the subset of the set of plant products, and a likelihood of infection of the set of plant products can each be determined at any combination of location(s). As one example, biomarker expression data (e.g., levels of biomarker expression) for a subset of a set of plant products, a set of biomarker expression statistics for the subset of the set of plant products, and a likelihood of infection of the set of plant products can all be determined at the location of the plant products. In another example, biomarker expression data (e.g., levels of biomarker expression) for a subset of a set of plant products can be determined at the location of the plant products, and then transmitted to another location (e.g., to a remote computing system) to determine a set of biomarker expression statistics for the subset of the set of plant products and a likelihood of infection of the set of plant products. In alternative implementations, prediction of infection likelihood in a set of plant products can be determined at any alternative combination of locations.

V.A. Infection Biomarkers

As discussed throughout this disclosure, levels of expression of infection biomarkers and housekeeping biomarkers in each plant product of a subset of plant products selected from a set of similarly sourced plant products are used to predict a likelihood of infection in the set of plant products. As also briefly discussed above with regard to FIG. 1, infection biomarkers include biomarkers that have been determined to be differentially expressed in infected plant products compared to uninfected plant products. And in an even further, preferred implementation, infection biomarkers include biomarkers that are differentially expressed by a threshold percentage in infected plant products compared to uninfected plant products. For instance, in a preferred implementation, infection biomarkers include biomarkers that have been determined to be differentially expressed in infected plant products compared to uninfected plant products by at least 0.1 fold.

As shown below, Table 1 depicts an exemplary set of biomarkers that satisfy this criterion of differential expression. Specifically, Table 1 depicts a set of genes for which expression in infected plant products differs compared to expression in uninfected plant products. Furthermore, in some implementations, the genes listed in Table 1 also satisfy the preferred criterion of differential expression between infected and uninfected plant products by a threshold percentage of at least 0.1 fold. Table 1 also indicates a pathway/response and a shorthand for each gene. The pathway/response of a gene indicates a metabolic pathway to which the gene contributes, or a downstream effect of expression of the gene. The shorthand of a gene indicates an acronym of the gene name. The infection biomarkers listed in Table 1 can be used either alone or together with housekeeping biomarkers discussed below to predict a likelihood of infection in a set of similarly sourced plant products.

TABLE 1

Exemplary Infection Biomarkers

| Gene | Pathway/Response | Shorthand |
|---|---|---|
| Catalase | ROS Mediation | Catalase |
| Chitinase | Pathogen Response | CHI |
| Plant U-box 29 | Pathogen Response | PUB29 |
| Syntaxin 121 | Pathogen Response | SYP121 |
| Chalcone Synthase | Phenylpropanoid Pathway | CHS |
| Lipoxygenase | Fatty Acid Synthesis | LOX |
| Pathogen Response Protein 6 | Pathogen Response Pathway | PR6 |
| Pathogen Response Protein 5 | Pathogen Response Pathway | PR5 |
| Glutathione-S-Transferase | Phenylpropanoid Pathway | GST |
| Flavanone-3-Hydroxylase | Phenylpropanoid Pathway | F3H |
| Phenylalanine Ammonia Lyase | Phenylpropanoid Pathway | PAL |
| Ferulic Acid 5-hydroxylase 1 | Phenylpropanoid Pathway | FAH1 |
| Ethylene Response Factor | Ethylene Synthesis/Response | ERF |
| Polygalacturonase | Pectin depolymerization | Polygal |
| WRKY Transcription Factor 75 | Stress Response Nuclear Transcription Factor | WRKY75 |
| Catechol-O-methyltransferase | Phenylpropanoid Pathway | COMT |
| Basic Pathogenesis-related 1-2 | Pathogen Response Pathway | PRbl-2 |
| Acetyl CoA Synthetase 1 | Ethylene Synthesis/Response | ACS1 |
| 1-aminocyclopropane-1-carboxylate oxidase | Ethylene Synthesis/Response | ACO1 |
| Acyl-coenzyme A oxidase | Ethylene Synthesis | ACO5 |
| Linoleate 9S-lipoxygenase 5 | Jasmonic Acid Synthesis | LOX5 |
| Alpha-farnesene | Jasmonic Acid Related | HF17844 |
| FA hyperoxide lyase | Jasmonic Acid Related | HPL |
| Ethylene response sensor 1 | Ethylene Signaling | ERS1 |
| Ethylene responsive transcription factor | Ethylene Signaling | TINY |
| Ethylene-responsive transcription factor 1 | Ethylene Signaling | TINY1 |
| Adipocyte Protein 2 | Ethylene Signaling | AP2 |
| AC Synthase | Ethylene Biosynthesis | HF30687 |
| AC Oxidase | Ethylene Biosynthesis | HF12321 |
| Pathogenesis-related protein | Pathogen Immune Response | PR10 |
| Receptor Like Protein Kinase 7 Chitin Elicitor | Pathogen Immune Response | HF10360 |
| Malate Dehydrogenase | Metabolism | HF09278 |
| Pryruvate Decarboxylase | Metabolism | HF15474 |
| Fumarate lyase | Metabolism | HF02735 |
| Phenylalanine Ammonia Lyase | Phenylpropanoid Pathway | PAL |
| Cinnamate-4-hydroxylase | Phenylpropanoid Pathway | C4H |
| Expansin A8 | Cell Wall Modification | EXPA8 |
| Nine-Cis-Epoxycarotenoid dioxygenase 9 | ABA Synthesis | NCED3 |
| WRKY transcription factor 31 | Stress Transcription Factor | WRKY31 |

To account for variation in biomarker expression between plant products, as discussed in further detail below in Example 1, a normalized level of expression of an infection biomarker can be determined based on the levels of expression of the infection biomarker and a housekeeping biomarker or of the infection biomarker and another infection biomarker. By normalizing the infection biomarker expression to the expression of a housekeeping biomarker or to the expression of another infection biomarker, variations in baseline infection biomarker expression between plant products can be controlled for.

In some implementations, a level of expression of certain subsets of the infection biomarkers in Table 1 may be detected for particular plant products. For example, if a plant or a subset of plants to be evaluated for latent infections includes an avocado, detection of a level of expression of a first particular subset of the infection biomarkers in Table 1 may be indicative of the presence or absence of a latent infection. In some implementations, the first particular subset of infection biomarkers can include one or more of PAL, GST, COMT, WRKY75, F3H, PR6, PR5, LOX, Prbl-2, or Catalase genes. By way of another example, if a plant or a subset of plants to be evaluated for latent infections includes an application, detection of a level of expression of a second particular subset of infection biomarkers in Table 1 may be indicative of the presence or absence of a latent infection. In some implementations, the second subset of infection biomarkers in Table 1 can include one or more of alpha-farnesene, FA hyperoxide lyase, ethylene response sensor 1, ethylene responsive transcription factor 1, TINY, AC Synthase, AC Oxidase, PR10, Recepter like protein kinase 7 chitin elicitor, Malate dhydrogenase, Pryuvate decarboxylase, Fumarate lyase, PAL, or C4H. In other implementations, the second subset of infection biomarkers in Table 1 can include one or more of Plant U-box 29, chitanse, syntaxin 121, ferulic acid 5-hydroxylase 1, cinnamate-4-hydroxylase, phenylalanine ammonia lyase, expansin A8, nine-cis-epoxycarotenoid dioxygenase 9, WRKY31, LOX5, ACS1, ACO5, or AP2.

The list of infection biomarkers in Table 1 and the aforementioned subsets of biomarkers are not exhaustive. Specifically, additional biomarkers that satisfy the criterion of differential expression in infected plant products compared to uninfected plant products can be included in Table 1.

In some implementations, the set of genes in the infected plant products that are different from the expression of genes in an uninfected plant can be identified by performing variant calling analysis on read sequences generated by a nucleic acid sequencer. For example, a nucleic acid sequence can be used to sequence a sample obtained from a set of plant products. Read sequences generated by the nucleic acid sequencer, based on the obtained sample, can be aligned to a reference sequence of a healthy plant. Variants, or differences, between the aligned read sequences and the reference sequence can then be obtained and serve as an expression of a set of genes of an infected plant that different from an expression of a set of genes in an uninfected plant.

V.B. Housekeeping Biomarkers

Turning next to the housekeeping biomarkers that are used to predict a likelihood of infection in the plant products, as briefly discussed above with regard to FIG. 1, housekeeping biomarkers include biomarkers that have been determined to not be correlated with infection in plant products. In other words, changes in housekeeping biomarker expression are less than 0.5, 0.4, 0.3, 0.2, or 0.1 fold in infected and uninfected plant products. Therefore, housekeeping biomarker expression can be used to normalize infection biomarker expression between infected and uninfected plant products. Specifically, housekeeping biomarker expression can be used to control for variations in baseline metabolic activity between plant products.

Many plant product housekeeping biomarkers are known to those skilled in the art. Table 2 below depicts a set of genes that are known to be housekeeping biomarkers in plant products, and that can be used to normalize infection biomarker expression between infected and uninfected plant products. Table 2 also indicates a pathway/response and a shorthand for each gene. The pathway/response of a gene indicates a metabolic pathway to which the gene contributes, or a downstream effect of expression of the gene. The shorthand of a gene indicates an acronym of the gene name.

TABLE 2

Exemplary Housekeeping Biomarkers

| Gene | Pathway/Response | Shorthand |
| --- | --- | --- |
| Actin | Cytoskeleton | ACTIN |
| α-tubulin | Cytoskeleton | TUA |
| Ubiquitin | Protein degradation | UBQ |
| Glyceraldehde-3-phosphate dehydrogense | Respiration | GAPDH |
| 18S ribosomal RNA and elongation factors | Protein synthesis | EF |
| 26S ribosomal RNA and elongation factors | Protein synthesis | EF |

In addition to the known housekeeping biomarkers listed in Table 2, any other housekeeping biomarkers can be used in the prediction of infection in plant products as discussed throughout this disclosure. Methods of identifying additional housekeeping biomarkers are also known to those skill in the art. For example, the following publication discusses known methods for identifying housekeeping genes in plant products: Chandna R, Augustine R, Bisht NC (2012) Evaluation of Candidate Reference Genes for Gene Expression Normalization in *Brassica juncea* Using Real Time Quantitative RT-PCR. PLOS ONE 7 (5): e36918. doi.org/10.1371/journal.pone.0036918 https://doi.org/10.1371/journal.pone.0036918. This publication, along with similar publications, can be used to identify additional housekeeping biomarkers aside from those listed in Table 2 for use in predicting infection in plant products.

The housekeeping biomarkers listed in Table 2, as well as additional housekeeping biomarkers identified according to known methods, can be used together with the infection biomarkers discussed above to predict a likelihood of infection in a set of similarly sourced plant products.

VI. Statistical Analysis of Biomarker Expression

Following determination of levels of expression of at least one infection biomarker and optionally at least one housekeeping biomarker in each plant product of a subset of plant products selected from a set of similarly sourced plant products, a statistical analysis of these levels of biomarker expression is performed. Specifically, as briefly discussed above with regard to FIG. 2B, a set of biomarker expression statistics 205 for the subset of plant products 202 is determined based on the infection biomarker expression 203A-D and optionally housekeeping biomarker expression 204A-D for each plant product 202A-D in the subset of plant products 202. This set of biomarker expression statistics 205 is used to predict the likelihood of infection 206 in the set of similarly sourced plant products, as discussed in detail below with regard to FIGS. 3-5D.

Alternatively, in some implementations, an absolute quantification of one or more biomarkers is determined employing the use of, for example, an authentic concentration standard, an internal standard or prepared standard curve of known concentrations. In these cases, a housekeeping biomarker expression may not need to be determined.

VI.A. Set of Biomarker Expression Statistics

Figure 2C:
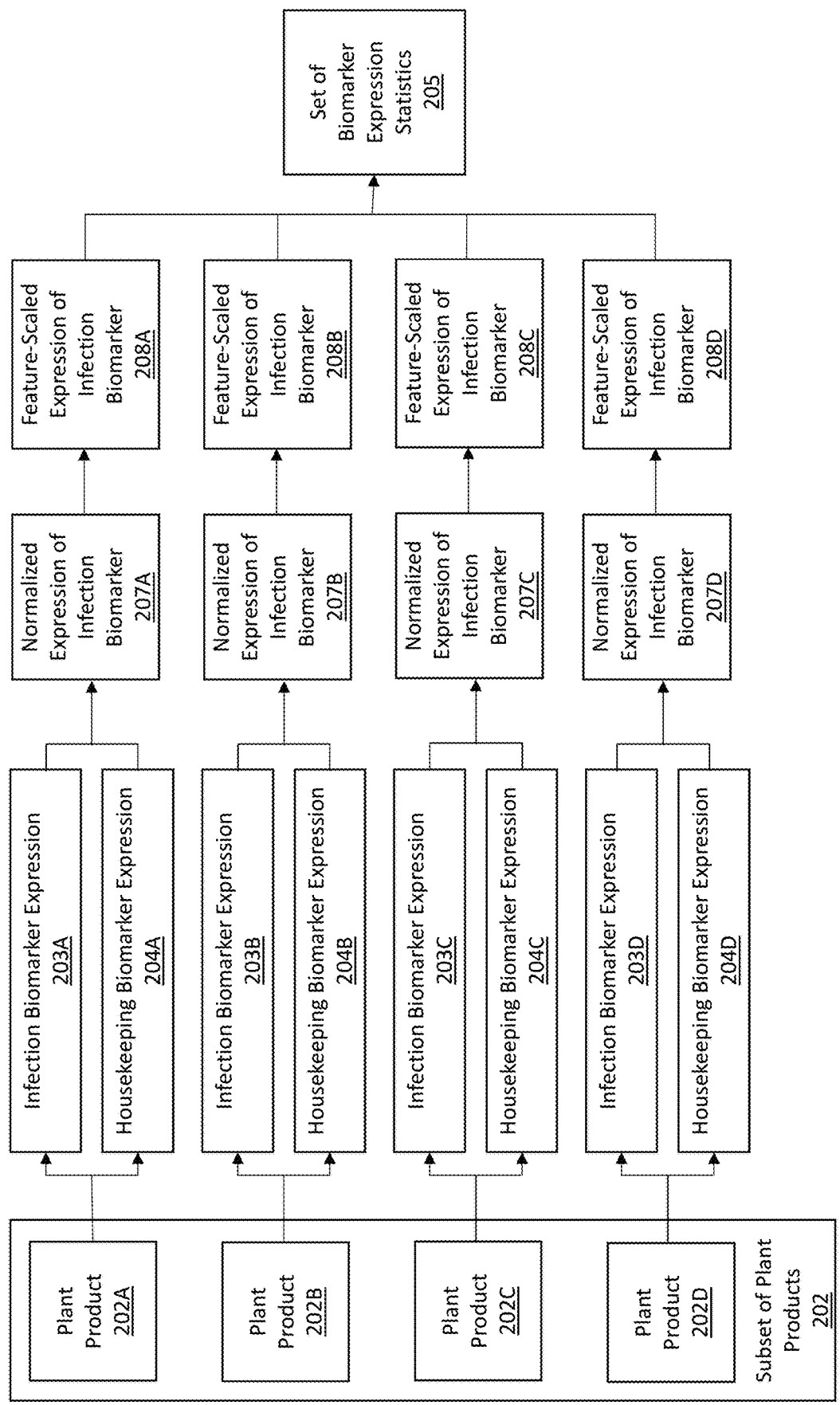
FIG. 2C is a block diagram of a system environment in which a set of biomarker expression statistics is determined for a subset of plant products.

FIG. 2C is a block diagram of an exemplary system environment 200C in which a set of biomarker expression statistics is determined for a subset of plant products. FIG. 2C is an extension of applications of FIGS. 2A-B in which expression of one or more housekeeping biomarkers is measured for each plant product of the subset of plant products. Specifically, the subset of plant products 202 and the associated infection biomarker expression 203A-D and housekeeping biomarker expression 204A-D determined for each plant product 202A-D of the subset of plant products 202 depicted in FIG. 2C is carried over from FIG. 2B. Thus, FIG. 2C is a block diagram of a system environment 200C in which the set of biomarker expression statistics 205 is determined for the subset of plant products 202 of FIGS. 2A-B.

As shown in FIG. 2C, in some implementations, the set of biomarker expression statistics 205 for the subset of plant products 202 is determined by determining a normalized level of expression of the at least one infection biomarker for each plant product 202A-D of the subset of plant products 202, and then determining a feature-scaled level of expression of the at least one infection biomarker for each plant product 202A-D of the subset of plant products 202. Specifically, in the exemplary implementation shown in FIG. 2C, a normalized level of expression 207A-D of the at least one infection biomarker is determined for each plant product 202A-D of the subset of plant products 202, based on the infection biomarker expression 203A-D and the housekeeping biomarker expression 204A-D determined for each plant product 202A-D. In particular, a normalized level of expression 207A of the at least one infection biomarker is determined for the plant product 202A, based on the infection biomarker expression 203A and the housekeeping biomarker expression 204A for the plant product 202A. Similarly, a normalized level of expression 207B of the at least one infection biomarker is determined for the plant product 202B, based on the infection biomarker expression 203B and the housekeeping biomarker expression 204B for the plant product 202B. A normalized level of expression 207C of the at least one infection biomarker is determined for the plant product 202C, based on the infection biomarker expression 203C and the housekeeping biomarker expression 204C for the plant product 202C. And finally, a normalized level of expression 207D of the at least one infection biomarker is determined for the plant product 202D, based on the infection biomarker expression 203D and the housekeeping biomarker expression 204D for the plant product 202D.

In certain implementations, a normalized level of expression of an infection biomarker for a plant product can be determined by determining a ratio of a level of expression of the infection biomarker in the plant product to a level of expression of a housekeeping biomarker in the plant product. For example, in an implementation in which the infection biomarker comprises the PAL gene shown in Table 1, and in which the housekeeping biomarker comprises the Actin gene shown in Table 2, a normalized level of expression of the PAL gene for a plant product can comprise a ratio of a level of expression of the PAL gene in the plant product to a level of expression of the Actin gene in the plant product. As briefly discussed above, by normalizing a level of expression of an infection biomarker to a housekeeping biomarker, variations in baseline metabolic activity between plant products can be controlled for.

After determination of the normalized level of expression 207A-D of the at least one infection biomarker for each plant product 202A-D of the subset of plant products 202, a feature-scaled level of expression 208A-D of the at least one infection biomarker for each plant product 202A-D of the subset of plant products 202 can be determined. Specifically, in the implementation shown in FIG. 2C, a feature-scaled level of expression 208A-D of the at least one infection biomarker is determined for each plant product 202A-D of the subset of plant products 202, based on the normalized level of expression 207A-D of the at least one infection biomarker for each plant product 202A-D. In particular, a feature-scaled level of expression 208A of the at least one infection biomarker is determined for the plant product 202A, based on the normalized level of expression 207A of the at least one infection biomarker for the plant product 202A. Similarly, a feature-scaled level of expression 208B of the at least one infection biomarker is determined for the plant product 202B, based on the normalized level of expression 207B of the at least one infection biomarker for the plant product 202B. A feature-scaled level of expression 208C of the at least one infection biomarker is determined for the plant product 202C, based on the normalized level of expression 207C of the at least one infection biomarker for the plant product 202C. And finally, a feature-scaled level of expression 208D of the at least one infection biomarker is determined for the plant product 202D, based on the normalized level of expression 207D of the at least one infection biomarker for the plant product 202D.

In general, a feature-scaled level of expression of an infection biomarker for a plant product can, for example, be determined by performing at least one of a min-max normalization[6] and a log transformation of a normalized level of expression of the infection biomarker for the plant product.

Finally, as shown in FIG. 2C, the set of biomarker expression statistics 205 is determined for the subset of plant products 202, based on the feature-scaled levels of expression 208A-D of the at least one infection biomarker for each plant product 202A-D. One implementation of this determination of the set of biomarker expression statistics 205, is shown and discussed in detail with regard to FIG. 2D.

Figure 2D:
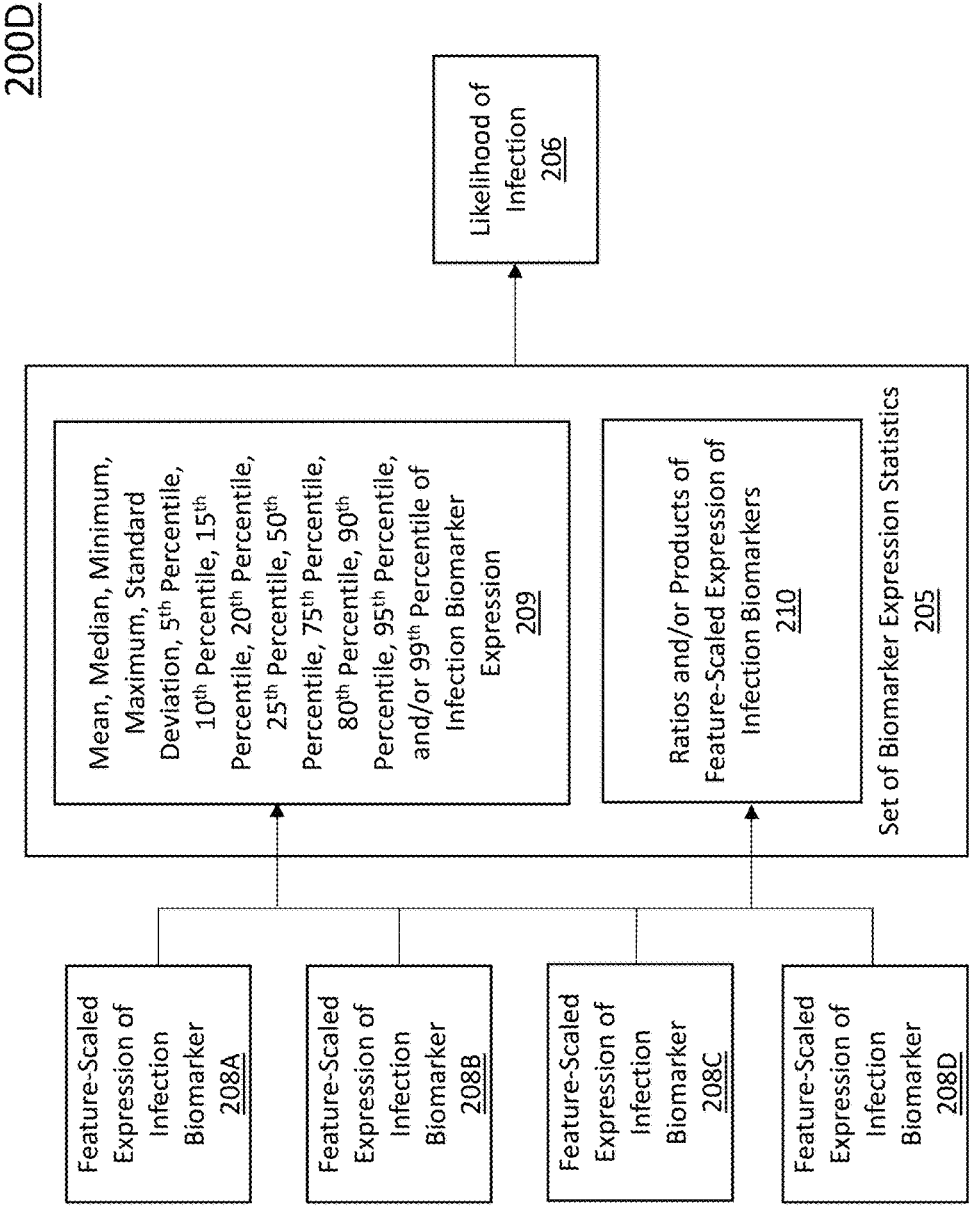
FIG. 2D is a block diagram of a system environment in which a set of biomarker expression statistics is determined for a subset of plant products.

FIG. 2D is a block diagram of an exemplary system environment 200D in which a set of biomarker expression statistics is determined for a subset of plant products. FIG. 2D is an extension of FIGS. 2A-C. Specifically, the levels of feature-scaled expression of the at least one infection biomarker 208A-D for the plant products 202A-D depicted in FIG. 2D are carried over from FIG. 2C. Thus, FIG. 2D is a block diagram of a system environment 200D in which the set of biomarker expression statistics 205 is determined for the subset of plant products 202 of FIGS. 2A-D.

As shown in FIG. 2D and as discussed above with regard to FIG. 2C, in some implementations, the set of biomarker expression statistics 205 is determined for the subset of plant products 202, based on the feature-scaled levels of expression 208A-D of the at least one infection biomarker for each plant product 202A-D. Furthermore, in the implementation depicted in FIG. 2D, the set of biomarker expression statistics 205 determined for the subset of plant products 202 comprises at least one of a mean, median, minimum, maximum, standard deviation, $5^{th}$ percentile, $10^{th}$ percentile, $15^{th}$ percentile, $20^{th}$ percentile, $25^{th}$ percentile, $50^{th}$ percentile, $75^{th}$ percentile, $80^{th}$ percentile, $90^{th}$ percentile, $95^{th}$ percentile and $99^{th}$ percentile (209 in FIG. 2D) of the feature-scaled levels of expression 208A-D of the at least one infection biomarker, a ratio 210 of the feature-scaled level of expression of at least one of the at least one infection biomarker to the feature-scaled level of expression of at least one other of the at least one infection biomarker for each plant product 202A-D of the subset of plant products 202, and a product 210 of the feature-scaled level of expression of at least one of the at least one infection biomarker and the feature-scaled level of expression of at least one other of the at least one infection biomarker for each plant product 202A-D of the subset of plant products 202.

For example, in an implementation of FIG. 2D in which the infection biomarkers comprise the PAL gene and the F3H gene shown in Table 1, the set of biomarker expression statistics 205 for the subset of plant products 202 can comprise a mean 209 of the feature-scaled levels of expression 208A-D for the PAL gene, a mean 209 of the feature-scaled levels of expression 208A-D for the F3H gene, and a ratio 210 of the feature-scaled level of expression 208A of the PAL gene to the feature-scaled level of expression 208A of the F3H gene for the plant product 202A, a ratio 210 of the feature-scaled level of expression 208B of the PAL gene to the feature-scaled level of expression 208B of the F3H gene for the plant product 202B, a ratio 210 of the feature-scaled level of expression 208C of the PAL gene to the feature-scaled level of expression 280C of the F3H gene for the plant product 202C, and a ratio 210 of the feature-scaled level of expression 208D of the PAL gene to the feature-scaled level of expression 208D of the F3H gene for the plant product 202D.

In alternative implementations, the set of biomarker expression statistics 205 for the subset of plant products 202 can comprise any statistics based on the infection biomarker expression 203A-D and the housekeeping biomarker expression 204A-D of the plant products 202A-D and/or based on the feature-scaled expression 208A-D of the at least one infection biomarker for the plant products 202A-D.

In further implementations, the set of biomarker expression statistics 205 for the subset of plant products 202 can include a combination of statistics based on the infection biomarker expression 203A-D and the housekeeping biomarker expression 204A-D of the plant products 202A-D and/or based on the feature-scaled expression 208A-D of the at least one infection biomarker for the plant products 202A-D and/or based on absolute expression values determined using for example, an internal standard or prepared standard curve of known concentrations.

Finally, as shown in FIG. 2D, the set of biomarker expression statistics 205 for the subset of plant products 202 is used to predict the likelihood of infection 206 for the set of similarly sourced plant products 201. This prediction of the likelihood of infection 206 is discussed in detail below with regard to FIGS. 3-5D.

VIII. Overview of an Additional Method

Figure 12:
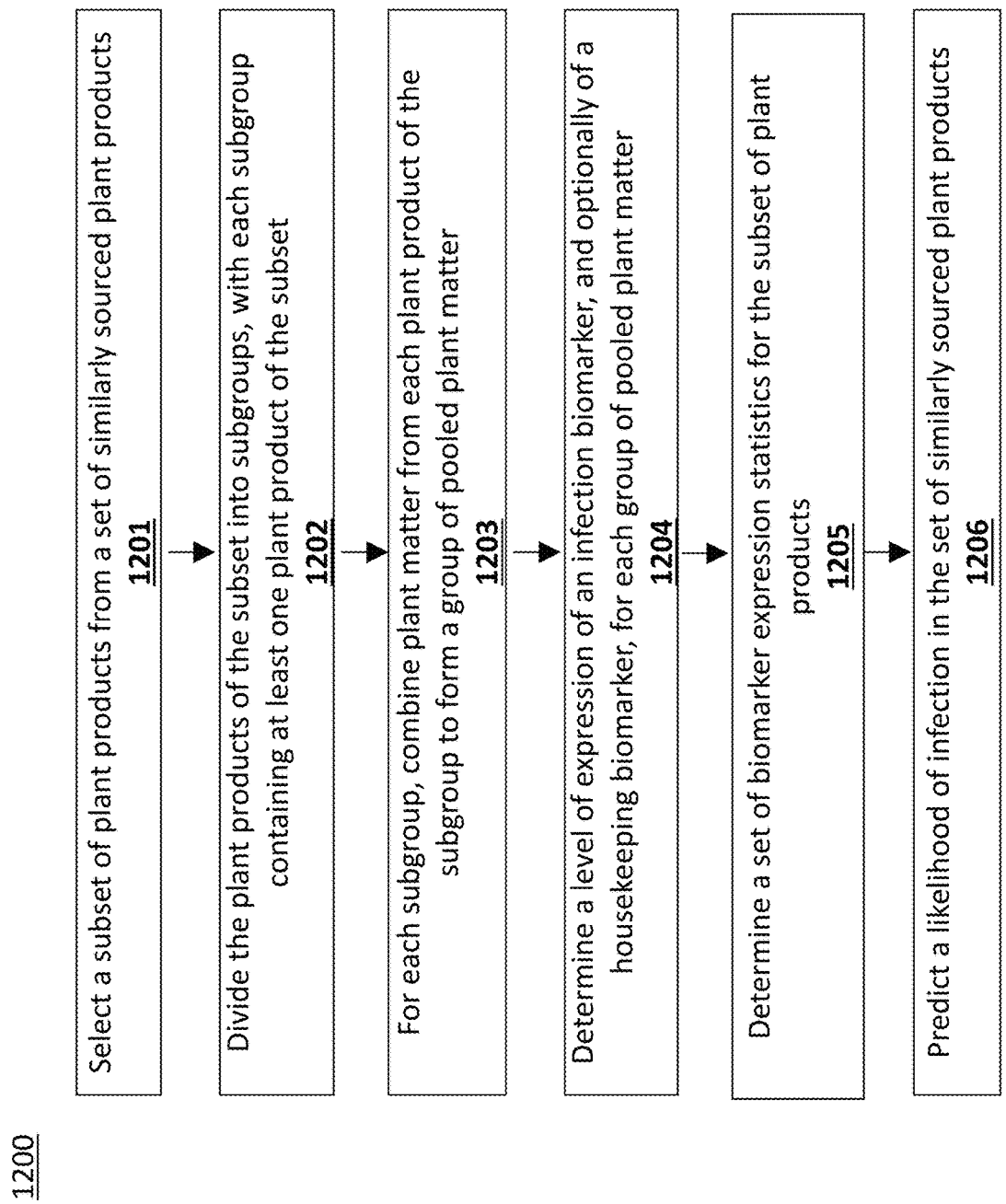
FIG. 12 is a flow chart of a method for predicting a likelihood of infection in a set of similarly sourced plant products.

Another method 1200 for predicting a likelihood of infection in a set of similarly sourced plant products is illustrated schematically in the flow chart of FIG. 12. The set of similarly sourced plant products typically includes a large enough number of plant products (e.g., greater than 10 plant products) to allow for the analytic methods described herein to be statistically valid. Although certain steps are shown to occur in a specific order, steps of the method can in some cases be performed in different orders than that described in conjunction with FIG. 12. Furthermore, in some cases certain steps may be omitted and/or substituted by other steps, and/or additional steps may be added.

To predict a likelihood of infection in a set of similarly sourced plant products, as shown in FIG. 12, a subset of plant products is selected 1201 from the set of similarly sourced plant products. The subset typically includes at least 3 plant products and less than half of the total number of products in the set of similarly sourced plant products. Selection 1201 of the subset of plant products from a set of similarly sourced plant products can follow the same process as that discussed above with reference to method 100 of FIG. 1. The plant products of the subset are then divided into subgroups, with each subgroup containing one or more of the plant products of the subset (step 1202). For each subgroup, plant matter from each plant product of the subgroup is then combined to form a group of pooled plant matter (step 1203). Combining plant matter from each of the plant products of the subgroup can, for example, include placing all of the plant products of the subgroup together in a blender and blending them to form the group of pooled plant matter.

A level of expression of at least one infection biomarker and optionally at least one housekeeping biomarker is then determined for each pooled plant matter group (step 1204). Preparation of the plant matter for biomarker analysis, as well as identification of infection biomarkers and housekeeping biomarkers suitable for predicting a likelihood of infection in plant products, can follow the same processes as those described above with reference to method 100 of FIG. 1.

Next, a set of biomarker expression statistics for the collection of pooled plant matter groups is determined based on the determined levels of expression of at least one infection biomarker and optionally of at least one housekeeping biomarker for each pooled plant matter group (step 1205). The same methods and metrics used to determine the set of biomarker expression statistics in method 100, which were described in detail above, can also be used with method 1200 of FIG. 12.

Finally, a likelihood of infection in the set of similarly sourced plant products is predicted based at least in part on the determined set of biomarker expression statistics for the collection of pooled plant matter groups (step 1206). Prediction of the likelihood of infection in the set of similarly sourced plant products can follow the same processes and metrics described above with reference to method 100 of FIG. 1. The predicted likelihood of infection in the set of similarly sourced plant products can then be returned, and in some implementations, leveraged to deliberately process the set of similarly sourced plant products. For example, a predicted likelihood of latent infection in a set of similarly sourced plant products can be used to determine when and where to sell the set of plant products.

Figure 13:
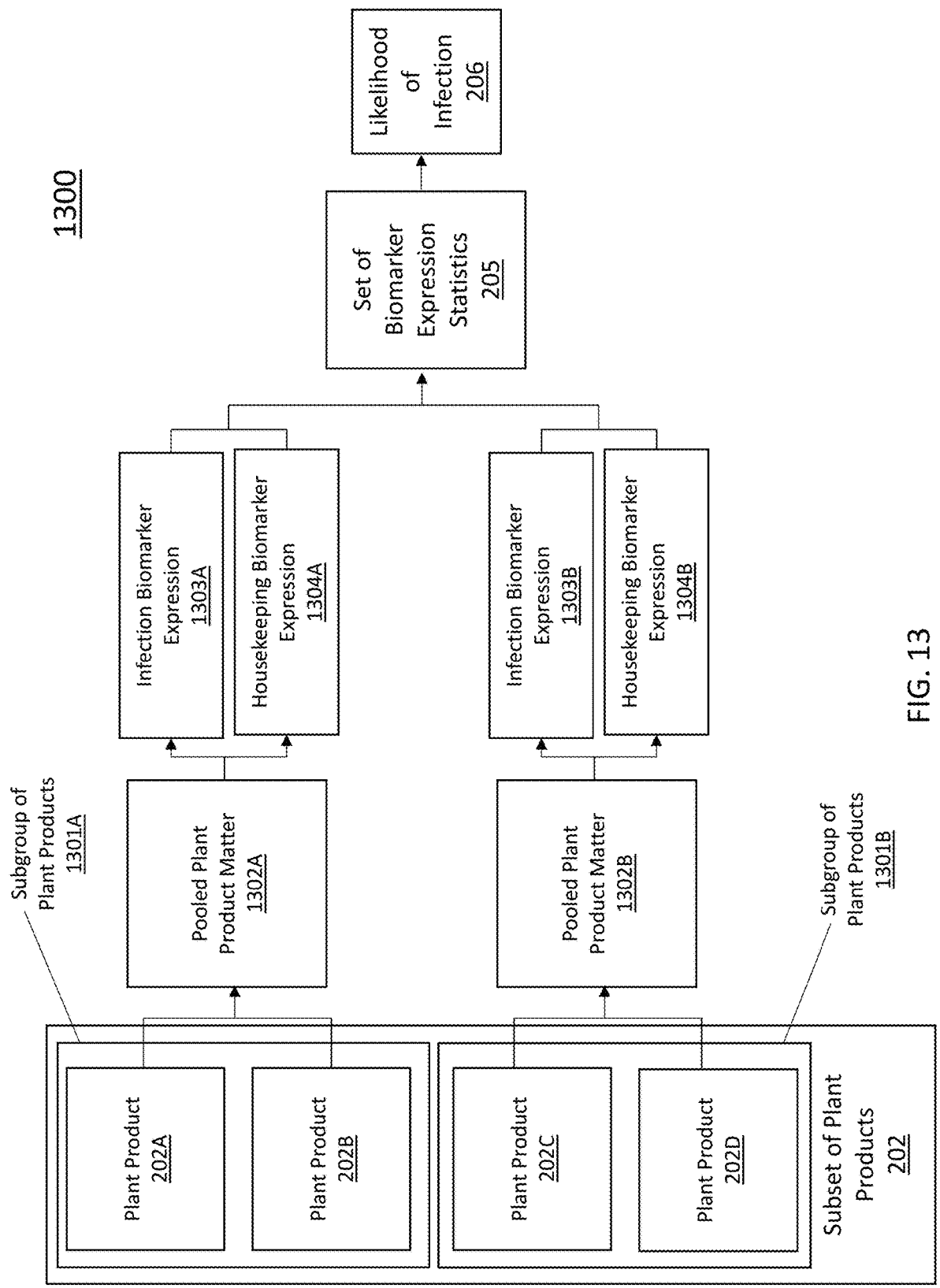
FIG. 13 is a block diagram of a system environment in which a likelihood of infection is predicted for a set of similarly sourced plant products.

FIG. 13 is a block diagram of a system environment 1300 in which a likelihood of infection 1306 is predicted for a set of similarly sourced plant products based on method 1200 of FIG. 12. Specifically, the subset of plant products 1302 depicted in FIG. 13 corresponds to the subset of plant products selected from the set of similarly sourced plant products in step 1201 of FIG. 12. As shown in FIG. 13, for clarity, each individual plant product of the subset of plant products 1302 is labeled as one of plant product 1302A, plant product 1302B, plant product 1302C, and plant product 1302D. Although the subset of plant products 1302 in FIG. 13 is shown to include four plant products, the subset could include 3, 4, or more than 4 plant products.

Still referring to FIG. 13, plant products 1302A and 1302B are then grouped into a first subgroup 1308A and plant products 1302C and 1302D are then grouped into a second subgroup 1308B, corresponding to step 1202 in FIG. 12. Although in FIG. 13 each of the subgroups contains the same number of plant products, in general the subgroups need not have the same number of plant products, but each subgroup should include at least 1 plant product of the subset 1302. For each of the subgroups (e.g., 1308A and 1308B), plant matter from each of the plant products in the subgroup is then combined to form groups of pooled plant matter 1310A and 1310B, respectively, corresponding to step 1203 in FIG. 12. For example, plant products 1302A and 1302B of subgroup 1308A can be placed in a blender and blended to form pooled plant matter group 1310A, and plant products 1302C and 1302D of subgroup 1308B can be placed in another blender and blended to form pooled plant matter group 1310B.

Next, a level of expression of at least one infection biomarker and optionally a level of expression of at least one housekeeping biomarker are determined for each of the pooled plant matter groups 1310A and 1310D, corresponding to step 1204 of FIG. 12. Specifically, infection biomarker expression 1303A and optional housekeeping biomarker expression 1304A are determined for pooled plant matter group 1310A, and infection biomarker expression 1303B and optional housekeeping biomarker expression 1304B are determined for pooled plant matter group 1310B. As discussed above, expression of a biomarker can be determined by measuring any substance that serves as a proxy for expression of the biomarker, according to any measurement method. For example, when the biomarker comprises a gene, a copy number of RNA transcripts of the gene can be a proxy for expression of the gene, and RT-qPCR can be used to quantify the copy number of the RNA transcripts of the gene. In some further implementations, biomarker expression can be determined using an array and/or kit configured to detect the biomarker expression. Thus, levels of expression of at least one infection biomarker and optionally at least one housekeeping biomarker for each of pooled plant matter groups 1310A and 1310B are determined by measuring any substance that serves as a proxy for expression of the biomarker, using any suitable measurement method.

Following determination of infection biomarker expression 1303A-B and optionally of housekeeping biomarker expression 1304A-B for pooled plant matter groups 1310A-B, a set of biomarker expression statistics 1305 for the collection of pooled plant matter groups is determined based on the infection biomarker expression 1303A-B and optionally the housekeeping biomarker expression 1304A-B, corresponding to step 1205 in FIG. 12. Finally, a likelihood of infection 1306 is predicted for the set of similarly sourced plant products from which the plant products of subset 1302 was selected, based at least in part on the set of biomarker expression statistics 1305 determined for the subset of plant products 1302, corresponding to step 1206 in FIG. 12.

IX. Infection Prediction System

Figure 3:
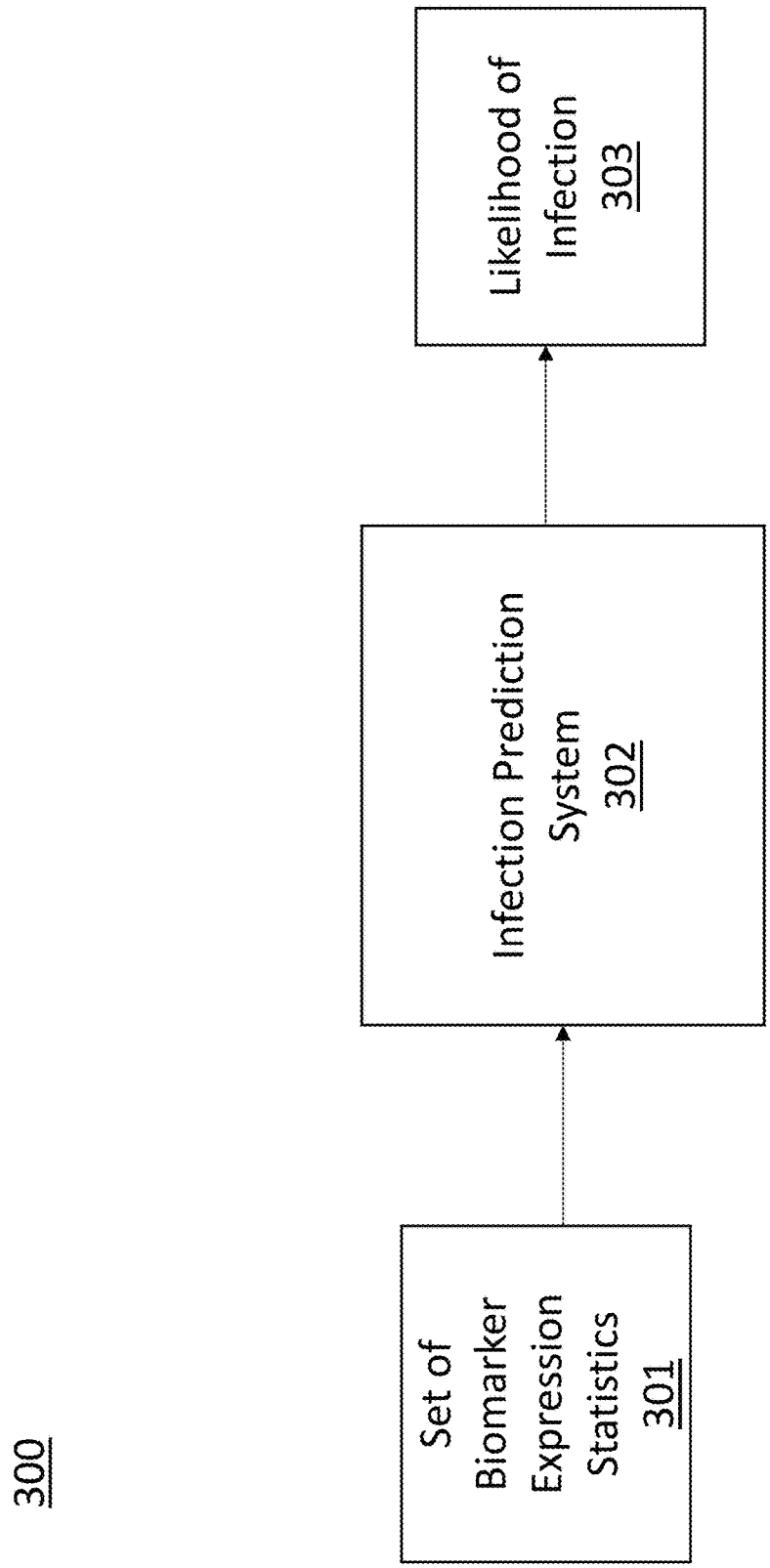
FIG. 3 is a block diagram of a system environment for an infection prediction system configured to predict a likelihood of infection in a set of similarly sourced plant products.

As mentioned above, a likelihood of infection in a set of similarly sourced plant products can be predicted based on a set of biomarker expression statistics for a subset of plant products selected from the set of similarly sourced plant products using a machine-learned infection prediction system. FIG. 3 is a block diagram of a system environment 300 for an infection prediction system 302 configured to predict a likelihood of infection 303 in a set of similarly sourced plant products. As discussed in further detail below with regard to FIG. 4, the infection prediction system 302 at least in part comprises a machine-learned infection prediction model. In alternative configurations, different and/or additional components may be included in the system environment 300.

As shown in FIG. 3, the infection prediction system 302 receives an input of a set of biomarker expression statistics 301 for a subset of plant products selected from a set of similarly sourced plant products. The set of biomarker expression statistics can be determined according to one of the implementations described above.

In some implementations, prior to inputting the set of biomarker expression statistics 301 into the infection prediction model that comprises the infection prediction system 302, the set of biomarker expression statistics 301 is encoded. Specifically, in some implementations, the set of biomarker expression statistics 301 is encoded prior to being input into the infection prediction system 302. In alternative implementations, the infection prediction system 302 contains an encoding module, and the set of biomarker expression statistics 301 is encoded by the encoding module following input into the infection prediction system 302, but prior to input into the infection prediction model of the infection prediction system 302. In some implementations, for example, the set of biomarker expression statistics 301 can be encoded into a data structure that includes an array of bits. For example, a set of biomarker expression statistics that includes a median feature-scaled level of expression of an RNA transcript of a gene of 200,000 copies of can be encoded in an array of bits as [110000110101000000]. Alternative methods of encoding the set of biomarker expression statistics 301 prior to input into the infection prediction model of the infection prediction system 302 may also be used.

This input of the set of biomarker expression statistics 301 is processed by the infection prediction system 302 to generate and output a likelihood of infection 303 in the set of similarly sourced plant products. The likelihood of infection 303 output by the infection prediction system 302 comprises a prediction of the likelihood of infection in the set of similarly sourced plant products. In some implementations, a likelihood of infection output by the infection prediction system 302 comprises a binary prediction of the likelihood of infection in the set of similarly sourced plant products. For example, a likelihood of infection output by the infection prediction system 302 can be '1,' representing a binary prediction that the set of similarly sourced plant products are infected, or '0,' representing a binary prediction that the set of similarly sourced plant products are uninfected.

In alternative implementations, a likelihood of infection output by the infection prediction system 302 comprises a prediction of a fraction of infected plant products of the set of similarly sourced plant products. For example, a likelihood of infection output by the infection prediction system 302 can be 0.27, representing a prediction that 27% of the plant products in the set of plant products are infected.

In some implementations, a likelihood of infection output by the infection prediction system 302 comprises a prediction of the likelihood (e.g., the percent likelihood) that a threshold fraction of the set of similarly sourced plant products is infected. For example, a likelihood of infection output by the infection prediction system 302 can be 0.25 (i.e., 25%) that at least ⅕ (i.e., 20%) of the plant products in the set of plant products are infected.

In further implementations, a likelihood of infection output by the infection prediction system 302 can comprise any other prediction of the likelihood of infection in the set of similarly sourced plant products.

IX.A. Infection Prediction System Architecture

Figure 4:
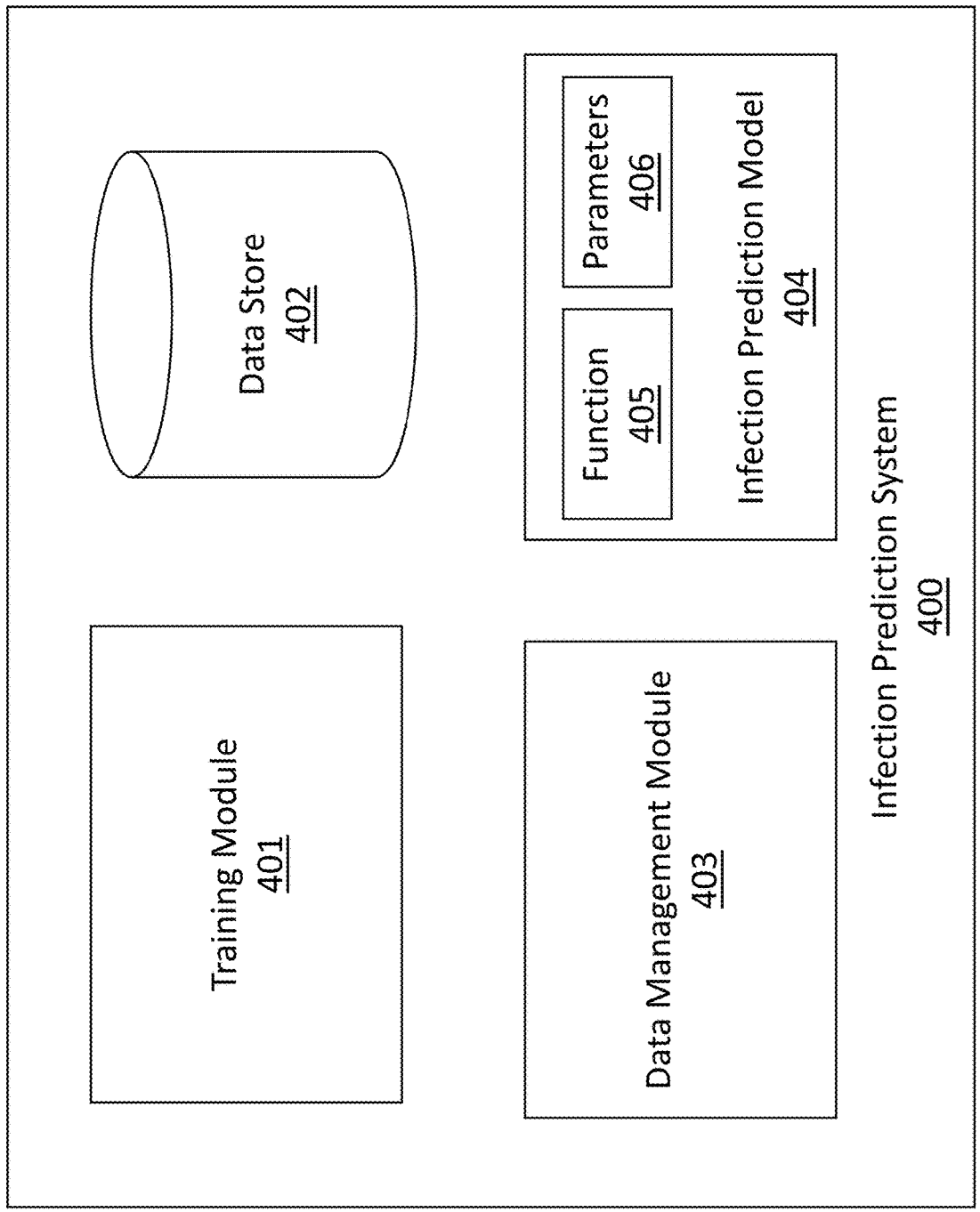
FIG. 4 is a block diagram of an architecture of an infection prediction system configured to predict a likelihood of infection in a set of similarly sourced plant products.

Turning next to FIG. 4, FIG. 4 is a block diagram of an architecture of an infection prediction system 400 configured to predict a likelihood of infection in a set of similarly sourced plant products. The infection prediction system 400 includes a training module 401, a data store 402, a data management module 403, and an infection prediction model 404. The infection prediction model 404 further comprises a function 405 and a set of parameters 406. In other implementations, the infection prediction system 400 may include additional, fewer, or different components for various applications. Similarly, the functions can be distributed among the modules in a different manner than is described here. Conventional components such as network interfaces, security functions, load balancers, failover servers, management and network operations consoles, and the like are not shown so as to not obscure the details of the system architecture.

IX.A.1. Training Module

The training module 401 constructs the infection prediction model 404 based on a training data set. In general, the infection prediction model 404 comprises a function 405 that captures the relationship between independent variables (e.g., sets of biomarker expression statistics) and dependent variables (e.g., rates of infection) in the training data set such that a loss function is minimized.

To construct the infection prediction model 404 using the training data set, each training sample i from the training data set is input into the infection prediction model 404. The infection prediction model 404 processes these inputs as if the model were being routinely used to generate a likelihood of infection in a set of similarly sourced plant products. However, unlike routine use of the infection prediction model 404, during training of the infection prediction model 404, known, retrospective rates of infection from the training data set are also input into the model. Specifically, retrospective rates of infection known to be accurate for the sets of similarly sourced plant products are also input into the model during training.

After each iteration of the infection prediction model 404 using a training sample i in the training data set, the model determines the difference between the predicted likelihood of infection in a set of similarly sourced plant products and the actual, retrospective rate of infection in the set of similarly sourced plant products. Then, the infection prediction model 404 seeks to minimize this difference. Specifically, the model seeks to minimize the difference between the predicted likelihood of infection in the set of similarly sourced plant products and the actual, retrospective rate of infection in the set of similarly sourced plant products.

To minimize this difference, the infection prediction model 404 minimizes a loss function for the infection prediction model 404. The loss function $l(u_{i \in S}, y_{i \in S}; \theta)$ represents discrepancies between values of dependent variables $u_{i \in S}$ for one or more training samples i in the training data S (e.g., known, retrospective rates of infection), and dependent variables $y_{i \in S}$ for the training samples i generated by model 404 (e.g., predicted likelihoods of infection). In simple terms, the loss function represents the difference between the predicted likelihoods of infection output by the model 404 and the known, retrospective rates of infection in the training data set. There are a plurality of loss functions known to those skilled in the art, and any one of these loss functions can be utilized in generating the infection prediction model 404.

By minimizing the loss function with respect to $\theta$, values for a set of parameters $\theta$ can be determined. In some implementations, the infection prediction model 404 can be a parametric model in which the set of parameters $\theta$ comprise the parameters 406 and mathematically modify the function 405 to specify the dependence between independent variables (e.g., sets of biomarker expression statistics) and dependent variables (e.g., rates of infection). In other words, the set of parameters θ determined by minimizing the loss function can comprise the set of parameters 406 and can be used to modify the function 405 of the infection prediction model 404 such that the accuracy of the infection prediction model 404 is optimized. Typically, the parameters of parametric-type models that minimize the loss function are determined through gradient-based numerical optimization algorithms, such as batch gradient algorithms, stochastic gradient algorithms, and the like. Alternatively, the infection prediction model 404 may be a non-parametric model in which the model structure is determined from the training data set and is not strictly based on a fixed set of parameters.

In implementations in which the infection prediction model 404 comprises a parametric-model, the model can generally be represented as:

$$y=f(x^k;\theta) \quad (1)$$

where y denotes the likelihood of infection in a set of similarly sourced plant products determined by the infection prediction model 404, $x^k$ denotes the set of biomarker expression statistics for a subset of the set of similarly sourced plant products, θ denotes the set of parameters 406 determined by minimizing the loss function with respect to θ, and $f(\bullet)$ is the function 405. In some implementations, the biomarker expression statistics $x^k$ are combined prior to being input into the function $f(\bullet)$. In alternative implementations, the biomarker expression statistics $x^k$ are not combined prior to being input into the function $f(\bullet)$.

The function 405 can be any function. For example, in some implementations, the function 405 can comprise one of a binary logistic regression model, logistic model tree, random forest classifier, L2 regularization, partial least squares classification, Naïve Bayes classifier, multivariate adaptive regression spines, one or more neural networks, and k-nearest neighbor classification.

In alternative implementations, the infection prediction model 404 comprises distinct functions 405 and distinct sets of parameters 406 for each biomarker expression statistic in the set of biomarker expression statistics $x^k$. For instance, as discussed above, a set of biomarker expression statistics $x^k$ can include more than one of a mean, median, minimum, maximum, standard deviation, $5^{th}$ percentile, $10^{th}$ percentile, $15^{th}$ percentile, $20^{th}$ percentile, $25^{th}$ percentile, $50^{th}$ percentile, $75^{th}$ percentile, $80^{th}$ percentile, $90^{th}$ percentile, $95^{th}$ percentile and $99^{th}$ percentile of feature-scaled levels or absolute levels of expression of at least one infection biomarker, a ratio of a feature-scaled level of expression of at least one infection biomarker to a feature-scaled level of expression of at least one other infection biomarker, and a product of a feature-scaled level of expression of at least one infection biomarker and a feature-scaled level of expression of at least one other infection biomarker. Additionally, a set of biomarker expression statistics $x^k$ can include statistics describing more than one infection biomarker. In such implementations, separate sets of parameters θ can be determined for each biomarker expression statistic and/or for each infection biomarker. For example, in an implementation in which a set of biomarker expression statistics $x^k$ includes independent variables of $x^1$, a $25^{th}$ percentile of the feature-scaled levels of expression an infection biomarker A, and $x^2$, a ratio of the feature-scaled level of expression of the infection biomarker A to a feature-scaled level of expression of an infection biomarker B, separate sets of parameters $\theta^1$ and $\theta^2$ can be determined for each independent variable $x^1$ and $x^2$, respectively. The values for the set of parameters $\theta^1$ are determined by minimizing the loss function with respect to $\theta^1$, and the values for the set of parameters $\theta^2$ are determined by minimizing the loss function with respect to $\theta^2$. The set of parameters $\theta^1$ are then used to modify a first function $f(x^1; \theta^1)$, and the set of parameters $\theta^2$ are used to modify a second function $f(x^2; \theta^2)$. Finally, these distinct functions modified by distinct sets of parameters can be combined to generate a likelihood of infection in the set of similarly sourced plant products. In such implementations, the infection prediction model 404 can be represented as:

$$y=f(x^1;\theta^1)+f(x^2;\theta^2) \quad (2)$$

where y denotes the likelihood of infection in the set of similarly sourced plant products determined by the infection prediction model 404, $x^1$ denotes a first independent variable (e.g., the $25^{th}$ percentile of the feature-scaled levels of expression the infection biomarker A), $x^2$ denotes a second independent variable (e.g., the ratio of the feature-scaled level of expression of the infection biomarker A to the feature-scaled level of expression of the infection biomarker B), $\theta^1$ denotes a first set of parameters 406 determined by minimizing the loss function with respect to $\theta^1$, $\theta^2$ denotes a second set of parameters 406 determined by minimizing the loss function with respect to $\theta^2$, and $f(\bullet)$ is a function 405. As discussed above with regard to Equation 1, the function $f(\bullet)$ can be any function. Furthermore, the $f(\bullet)$ functions denoted in Equation 2 are not required to be the same function.

When the infection prediction model 404 achieves a threshold level of prediction accuracy (e.g., when the loss function is sufficiently minimized), the model is ready for use. To determine when the infection prediction model 404 has achieved the threshold level of prediction accuracy sufficient for use, validation of the infection prediction model 404 can be performed. Validation of the infection prediction model 404 is discussed in further detail below with regard to FIG. 5C.

Once the infection prediction model 404 has been validated as having achieved the threshold level of prediction accuracy sufficient for use, in some implementations, this does not preclude the model from continued training. In fact, in a preferred implementation, despite validation, the infection prediction model 404 continues to be trained such that the set of parameters 406 of the model are continuously updated, such that the loss function is continues to decrease and the accuracy of the model continues to improve.

IX.A.2. Data Store

In some implementations, the data store 402 stores the training data set that is used to train the infection prediction model 404 as discussed above with regard to the training module 401. The training data set comprises a plurality of training samples. Each training sample i from the training data set is associated with a retrospective set of similarly sourced plant products. Specifically, each training sample i from the training data set is associated with a retrospective set of similarly sourced plant products in which an actual, known rate of infection is known. Each training sample i comprises a set of biomarker expression statistics for a subset of the retrospective set of similarly sourced plant products, and the actual, known rate of infection in the retrospective set of similarly sourced plant products. In certain implementations, the actual, known rate of infection in the retrospective set of similarly sourced plant products that is input into the infection prediction model 404 during training is encoded as discussed above with regard to encoding of the set of biomarker expression statistics input into the infection prediction model 404.

In some implementations discussed in detail below with regard to FIGS. 5A and 5C, one or more training samples from the training data set can be held out from training, and used to validate the infection prediction model 404.

IX.A.3. Data Management Module

The data management module 403 generates the training data set used to train the infection prediction model 404. As mentioned above, each training sample i from the training data set is associated with a retrospective set of similarly sourced plant products and an actual, known rate of infection in the retrospective set of similarly sourced plant products. Thus, the data used by the data management module 403 to generate the training data set can be sourced from a retrospective data source.

In implementations in which the training data set is stored by the data store 402, the data management module 403 stores the generated training data set in the data store 402. In implementations in which the infection prediction model 404 is also validated, the data management module 403 can also hold out training samples from the training data set to be used to validate the infection prediction model 404.

IX.A.4. Infection Prediction Model

The infection prediction model 404 is a machine-learned model configured to receive an input of a set of biomarker expressions statistics for a subset of plant products selected from a set of similarly sourced plant products, and to predict a likelihood of infection in the set of similarly sourced plant products. As discussed above, in general, the infection prediction model 404 comprises a function 405 modified by a set of parameters 406 to accurately capture the relationship between independent variables (e.g., sets of biomarker expression statistics) and dependent variables (e.g., rates of infection) in the training data set. As discussed above, in some implementations, function 405 comprises one of a binary logistic regression model, logistic model tree, random forest classifier, L2 regularization, partial least squares classification, Naïve Bayes classifier, multivariate adaptive regression spines, one or more neural networks, and k-nearest neighbor classification.

In some implementations, the infection prediction model 404 comprises a single model configured to predict likelihoods of infection in a set of similarly sourced plant products. However, in alternative implementations, the infection prediction model 404 can comprise multiple distinct models, each configured to perform a particular task. For example, in one implementation, the infection prediction model 404 can comprise a plurality of models, each configured to predict a likelihood of a particular type of infection.

X. Training, Validation, and Use of the Infection Prediction System

Figure 5A:
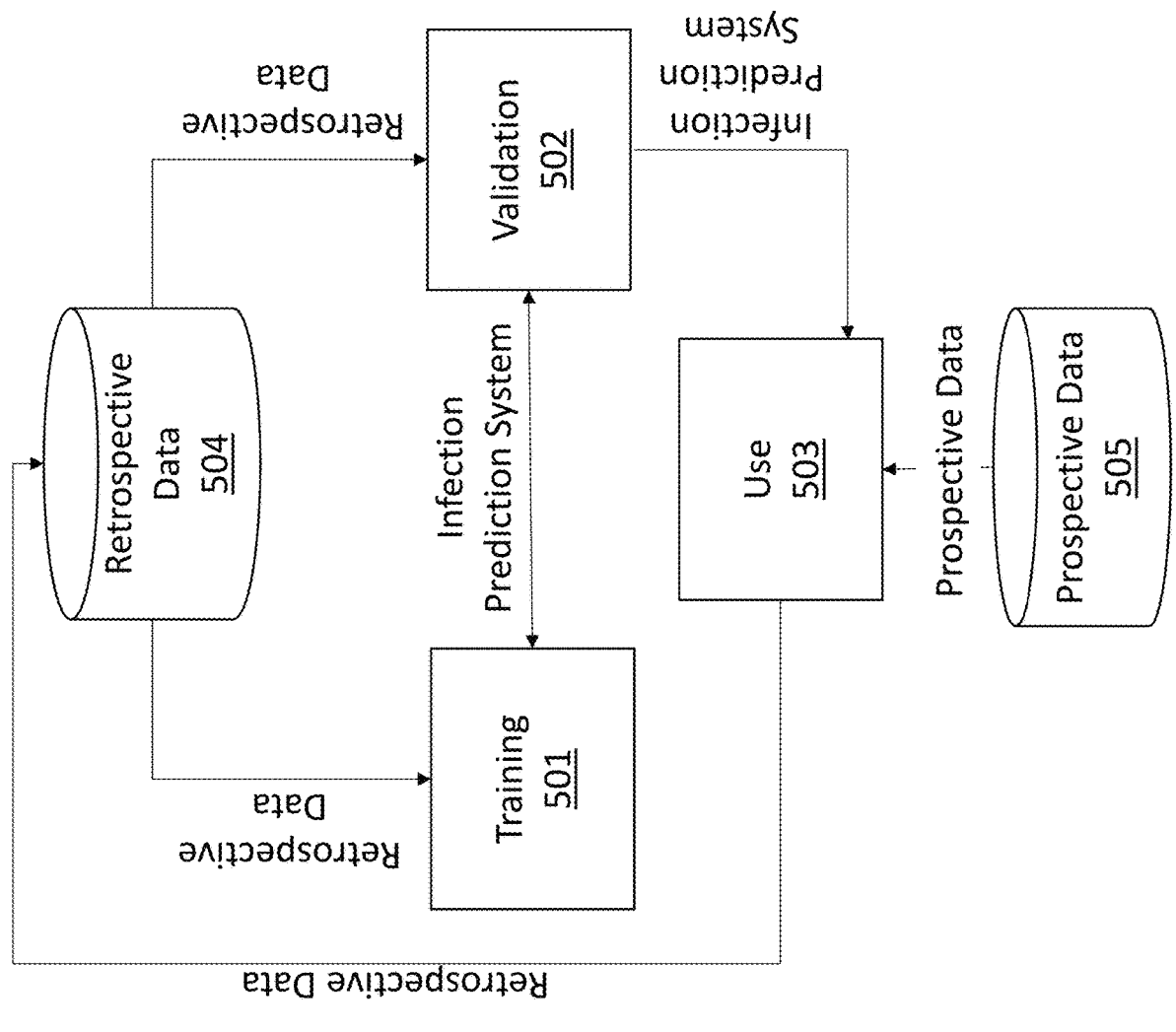
FIG. 5A is a block diagram of a system environment in which an infection prediction system is trained, validated, and used.

FIG. 5A is a block diagram of a system environment 500A in which an infection prediction system is trained, validated, and used. FIG. 5A includes a training phase 501, a validation phase 502, a use phase 503, a retrospective data store 504, and a prospective data store 505. Thus, FIG. 5A depicts how retrospective and prospective data are used to train, validate, and test an infection prediction system.

As discussed above with regard to FIG. 4, prior to use of an infection prediction system, the system is trained. As shown in FIG. 5A, training of the infection prediction system is accomplished using retrospective data received from the retrospective data source 504. The retrospective data source 504 contains a training data set comprising training data samples as discussed above with regard to the data store 402 of FIG. 4. In other words, the retrospective data source 504 contains data describing past rates of infection in sets of similarly sourced plant products. The data contained in the retrospective data source 504 can include private data, publicly-available data, commercially-available data, test data recycled after undergoing testing using the infection prediction model 404 at the use phase 503, and/or any other source of retrospective data.

Following or in conjunction with training, in some implementations, the infection prediction system can also undergo validation in the validation phase 502 to determine whether the system has achieved a threshold level of prediction accuracy and is ready for use. As briefly discussed above, in implementations in which the infection prediction system is validated, one or more training samples from the retrospective data source 504 can be held out from the training phase 501, and used to validate the infection prediction system.

Once the infection prediction system has been validated as having achieved the threshold level of prediction accuracy sufficient for use, the system is ready for the use phase 503. However, in some implementations, this does not preclude the system from continued training. In fact, in a preferred implementation, despite validation, the infection prediction system continues to be undergo training such that the system is continuously updated, and the accuracy of the system continues to improve.

Turning to the use phase 503, the infection prediction system is used to predict likelihoods of infection in sets of similarly sourced plant products associated with prospective data received from the prospective data source 505. The prospective data source 505 contains data describing independent variables (e.g., sets of biomarker expression statistics) for subsets of sets of similarly sourced plant products in which likelihoods of infection are to be predicted. The data contained in the prospective data source 505 can include publicly-available data, commercially-available data, data received from a private entity (e.g., a plant product producer), and/or any other source of prospective data.

Following use of the infection prediction system to predict likelihoods of infection in sets of similarly sourced plant products during the use phase 503, the independent variables (e.g., sets of biomarker expression statistics) received by the infection prediction system from the prospective data source 505 during the use phase 503, as well as an actual, retrospective rate of infection in the set of similarly sourced plant products, can be used as retrospective data to train or validate the system. In other words, prospective data 505 used by the infection prediction system during the use phase 503 can become retrospective data 504 used to train or validate the infection prediction system during the training phase 501 or the validation phase 502, respectively. In this way, the infection prediction system can be continuously trained and validated.

X.A. Training

Figure 5B:
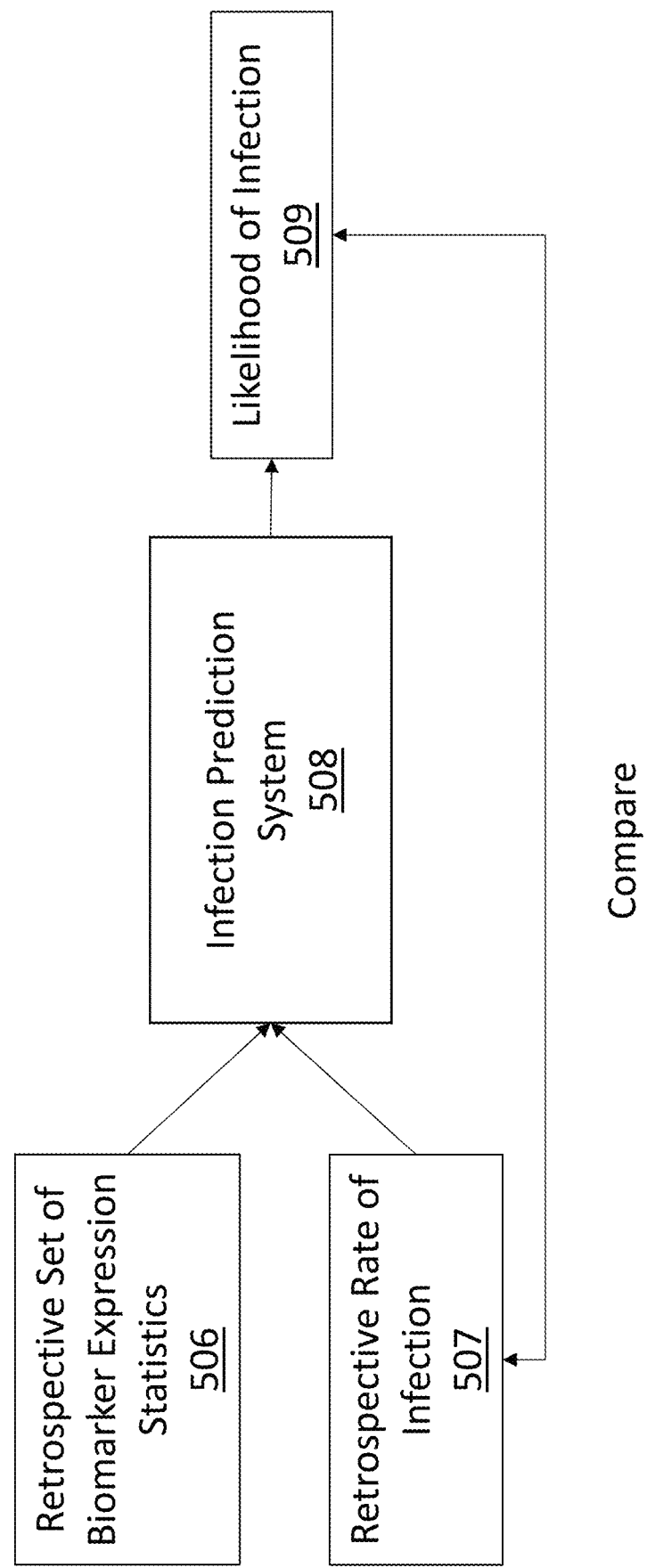
FIG. 5B is a block diagram of a system environment in which an infection prediction system is trained.
Figure 5C:
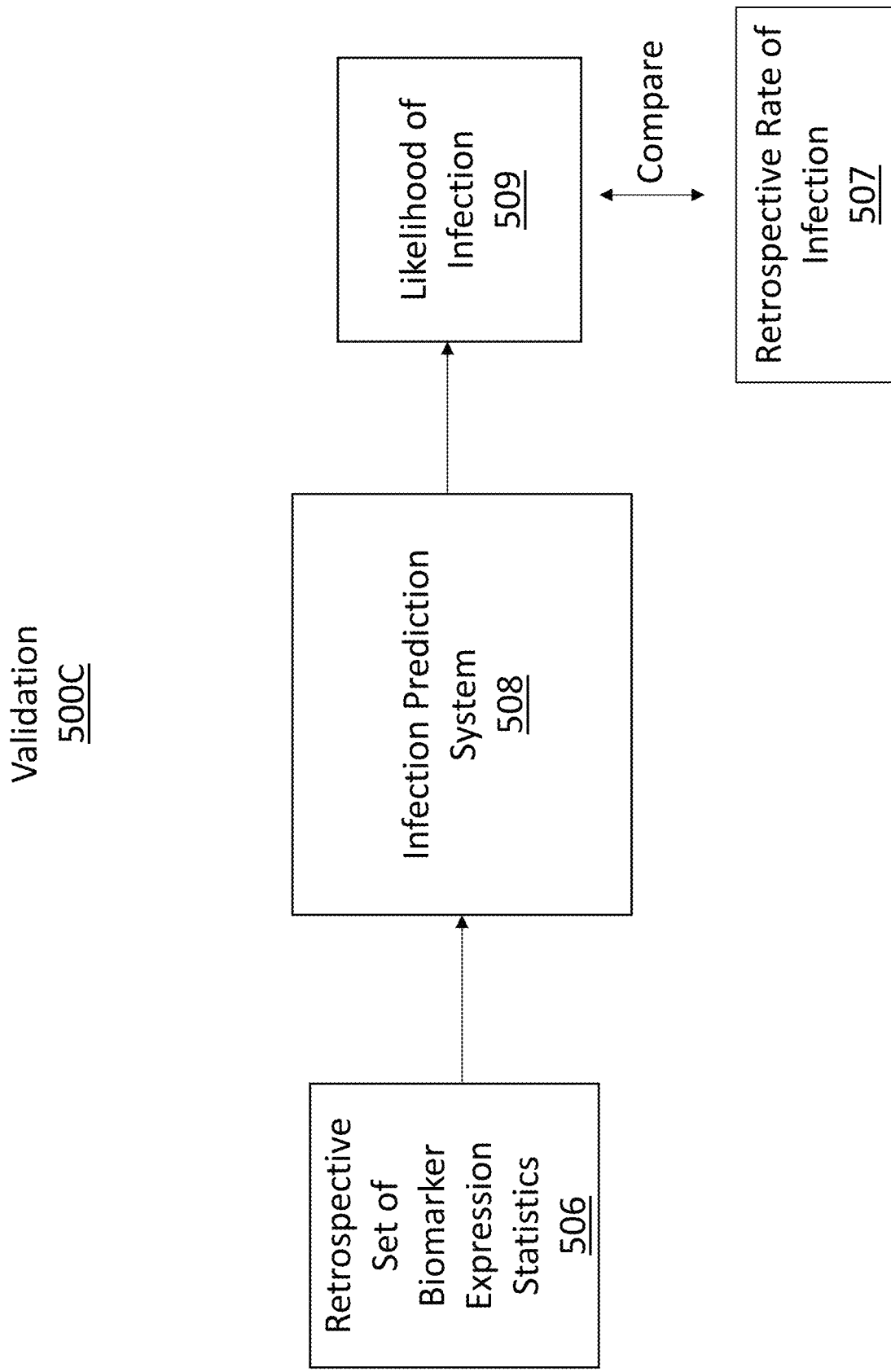
FIG. 5C is a block diagram of a system environment in which the infection prediction system is validated.

FIG. 5B is a block diagram of a system environment 500B in which an infection prediction system 508 is trained. As shown in FIG. 5B, to train the infection prediction system 508, a retrospective set of biomarker expression statistics 506 for a subset of a retrospective set of similarly sourced plant products, and an actual, retrospective rate of infection 507 in the retrospective set of similarly sourced plant products are input into the infection prediction system 508.

Following input of the retrospective set of biomarker expression statistics 506 and the actual, retrospective rate of infection 507 into the infection prediction system 508, the infection prediction system 508 determines and outputs a likelihood of infection 509 in the set of similarly sourced plant products, based on the retrospective set of biomarker expression statistics 506 and the actual, retrospective rate of infection 507. The likelihood of infection 509 in the set of similarly sourced plant products output by the infection prediction system 508 is not based on the actual, retrospective rate of infection 507 input into the infection prediction system 508. Rather, the likelihood of infection 509 determined and output by the infection prediction system 508 is compared to the actual, retrospective rate of infection 507.

This comparison of the likelihood of infection 509 determined and output by the infection prediction system 508 with the actual, retrospective rate of infection 507 enables the infection prediction system 508 to determine parameters that optimize the accuracy of the infection prediction system 508 as discussed in detail above with regard to FIG. 4. In other words, this comparison enables the infection prediction system 508 to be trained.

X.B. Validation

As discussed above, in some implementations, following or in conjunction with training, the infection prediction system 508 can also undergo validation to determine whether the system has achieved a threshold level of prediction accuracy and is ready for use. FIG. 5C is a block diagram of a system environment 500C in which the infection prediction system 508 is validated.

As briefly discussed above, during training of the infection prediction system 508, one or more training samples can be held out from training and used to validate the infection prediction system. Specifically, as shown in FIG. 5C, to validate the infection prediction system 508, a held out training sample comprising a retrospective set of biomarker expression statistics 506 for a subset of a retrospective set of similarly sourced plant products is input into the infection prediction system 508. However, unlike in training, an actual, retrospective rate of infection in the set of similarly sourced plant products is not input into the infection prediction system 508.

Following input of retrospective set of biomarker expression statistics 506 into the infection prediction system 508, the infection prediction system 508 determines and outputs a likelihood of infection 509 in the set of similarly sourced plant products based on the retrospective set of biomarker expression statistics 506. Then, the likelihood of infection 509 output by the infection prediction system 508 is compared to the actual, retrospective rate of infection in the set of similarly sourced plant products 507 that was not input into the infection prediction system 508.

The comparison of the likelihood of infection 509 determined and output by the infection prediction system 508 with the actual, retrospective rate of infection 507, enables a determination of whether the infection prediction system 508 has achieved a threshold level of prediction accuracy. If the infection prediction system 508 is determined to have achieved a threshold level of prediction accuracy based on this comparison, the infection prediction system 508 can be considered validated, and is ready for use. In some implementations, validation of the infection prediction system 508 results in an end to training of the infection prediction system 508. However, in alternative, preferred implementations, validation of the infection prediction system 508 does not preclude the infection prediction system 508 from training, and the infection prediction system 508 continues to undergo training throughout its use.

In implementations in which the infection prediction system 508 is determined to have not achieved a threshold level of prediction accuracy based on the comparison, the infection prediction system 508 can be further trained prior to use.

X.C. Use

Figure 5D:
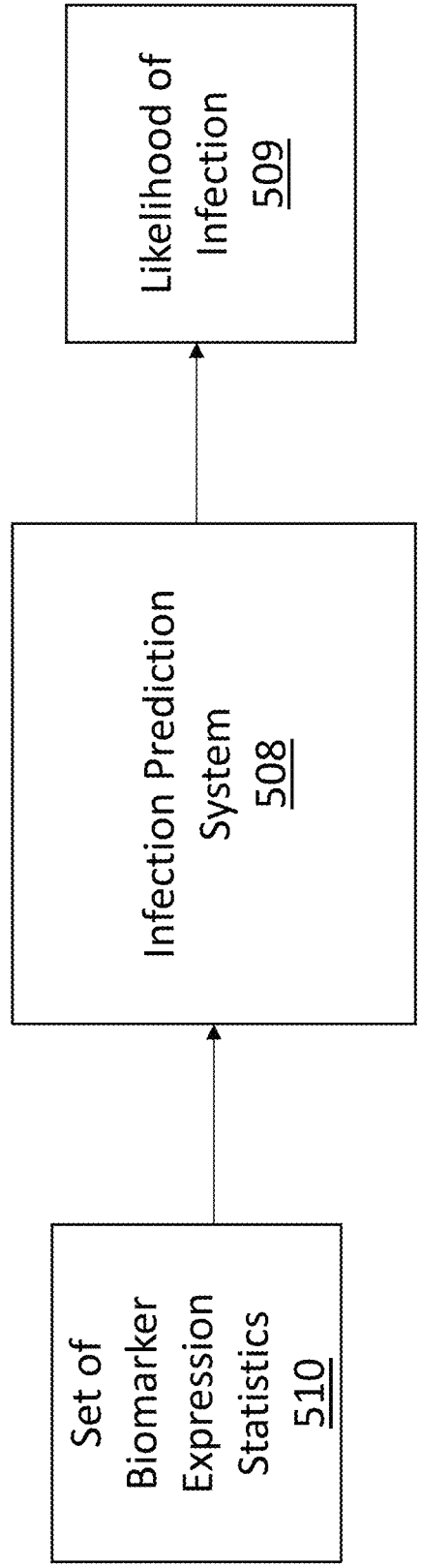
FIG. 5D is a block diagram of a system environment in which the infection prediction system is used.

Once the infection prediction system 508 has been validated as having achieved the threshold level of prediction accuracy, the system is ready to be used. FIG. 5D is a block diagram of a system environment 500D in which the infection prediction system 508 is used. As shown in FIG. 5D and as discussed in detail above, to use the infection prediction system 508, a set of biomarker expression statistics 510 for a subset of a set of similarly sourced plant products are input into the infection prediction system 508. Unlike in training and validation, the set of biomarker expression statistics 510 is not retrospective data for a retrospective set of similarly sourced plant products. Rather, the set of biomarker expression statistics 510 is for a subset of a set of similarly sourced plant products for which an actual, retrospective rate of infection is not yet known.

Following input of the set of biomarker expression statistics 510 into the infection prediction system 508, the infection prediction system 508 determines and outputs a likelihood of infection 509 in the set of similarly sourced plant products based on the set of biomarker expression statistics 510. During use, this likelihood of infection 509 is not compared to an actual, retrospective rate of infection in the set of similarly sourced plant products because an actual, retrospective rate of infection is not yet known. Instead, the likelihood of infection 509 output by the infection prediction system 508 is assumed to be sufficiently accurate based on prior training and validation of the infection prediction system 508.

However, in some implementations as discussed above with regard to FIG. 5A, once an actual, retrospective rate of infection in the set of similarly sourced plant products is known, the actual, retrospective rate of infection in the set of similarly sourced plant products and the likelihood of infection 509 output by the infection prediction system 508 can be used to train and or validate the system. In this way, the infection prediction system 508 can be continuously trained and validated throughout use.

XI. Plant Product Processing Based on Infection Prediction

Following prediction of a likelihood of infection in a set of similarly sourced plant products, the predicted likelihood of infection can be provided in any form. In some implementations, the likelihood of infection is automatically presented to a viewing user (e.g., digitally displayed). In further implementations, the likelihood of infection can be automatically electronically stored, automatically wirelessly transmitted to a remote system, and/or returned by any other method.

In some implementations, the set of similarly sourced plant products for which the likelihood of infection is predicted can undergo processing based on the predicted likelihood of infection. For example, in one implementation, a set of similarly sourced plant products that is at high risk for infection can be identified based on the predicted likelihood of infection.

In another implementation, an anti-microbial treatment can be provided or a dose of antimicrobial treatment can be prescribed to the set of similarly sourced plant products based on the predicted likelihood of infection. Specifically, a set of plant products with a relatively high predicted likelihood of infection can be provided with or prescribed an anti-microbial treatment to avoid progression of infection. Alternatively, a set of plant products with a relatively low predicted likelihood of infection can be prescribed a low or zero dose of antimicrobial treatment, thus enabling resource optimization and potentially lowering total antimicrobial use.

In some implementations, the subject matter of the present disclosure can be used to evaluate plants in transit using a vehicle from a first location such as a plant storage warehouse to a second location such as another plant storage warehouse, other distribution center, or a market. In such implementations, if more than a threshold level of infection is detected, then an alert can be generated that causes the vehicle to redirect to a third location that is geographically closer to the current location of the vehicle than the second location. In some implementations, this can include notifying a driver, pilot, or admiral, of the vehicle (e.g., a truck, a plane, or a boat) to navigate to the third location. Such a redirect may be done, for example, so that the one or more infected plants can be put into refrigeration more quickly in an effort to slow the advance of the detected infection. In some implementations, this can salvage the one or more infected plants before the latent infection causes the one or more infected plants to acquire rot such as stem rot. However, the present disclosure is not so limited. Instead, in other implementations, the third location may be an anti-microbial treatment facility that enables the one or more infected plants to be treated with an antimicrobial treatment, as described above, before the vehicle is allowed to continue toward the second location. Alternatively, if it is determined that less than a threshold level of infection one or more plants is detected, then no alert to redirect the vehicle is generated and the vehicle is permitted to continue along its current navigational path.

In an implementation in which the set of similarly sourced plant products have not yet been harvested, the set of plant products can be selectively harvested based on the predicted likelihood of infection. For example, in one implementation, a time of harvest of a set of plant products may be determined based on a predicted likelihood of infection of the set of plant products. In another exemplary implementation, a method of harvest of a set of plant products may be determined based on the predicted likelihood of infection of the set of plant products.

In another implementation, a quality assurance for the set of similarly sourced plant products can be determined based on the predicted likelihood of infection. For example, a quality assurance can be determined for a set of similarly sourced plant products with a predicted likelihood of infection below a certain threshold. For instance, a quality assurance can be determined for any set of similarly sourced plant products with a predicted likelihood of infection below 5%, 10%, 15%, 20% or 25%.

In another implementation, at least one of a consumer and a geographic destination for the set of similarly sourced plant products can be identified based on the predicted likelihood of infection. For example, a set of plant products with a relatively high predicted likelihood of infection can be sent to a consumer at a nearby geographic destination to avoid progression of the infection over long distances of transport. Similarly, a set of plant products with a relatively high predicted likelihood of infection can be sent to a consumer with relatively lower product standards.

In another implementation, ethylene treatment can be withheld from or a dose of ethylene treatment provided to or prescribed for the set of similarly sourced plant products based on the predicted likelihood of infection. Specifically, ethylene treatment is used to alter the ripening rate of plant products. However, the application of exogenous ethylene or the application of ethylene blockers/pathway inhibitors, for example, can also alter the progression of some infections in some plant products. Thus, in a set of plant products with a relatively high predicted likelihood of infection, ethylene treatment can be avoided or alternatively provided or properly prescribed to prevent acceleration of infection progression in the plant products.

In another implementation, one of more storage conditions for the set of similarly sourced plant products can be identified based on the predicted likelihood of infection in the plant products. The storage conditions can include storage temperature and/or storage humidity. For example, in a set of plant products with a relatively high predicted likelihood of infection, the set of plant products can be stored at a low temperature and/or a low humidity to slow infection progression in the plant products.

In yet another implementation, a post-harvest treatment can be provided to the set of similarly sourced plant products based on the predicted likelihood of infection in the set of plant products. For example, a post-harvest treatment can be provided to a set of similarly sourced plant products with a high predicted likelihood of infection. Post-harvest treatments can include the Apeel treatment and any other post-harvest plant product treatment.

In addition to the post-infection-prediction processing steps described above, a set of similarly sourced plant products can undergo any type of processing based on a predicted likelihood of infection determined for the set of plant products. Furthermore, in addition to providing the predicted likelihood of infection, the method disclosed herein may also include provision of plant product processing instructions to a user based on the predicted likelihood of infection. These instructions can instruct a user to perform any plant product processing steps, including any of the plant processing steps mentioned above. In a further implementation, plant processing steps based on the predicted likelihood of infection in a set of similarly sourced plant products can be automatically performed.

XII. Example 1—Prediction of *C. gloeosporioides* Infection in Avocados

The following example validates the methods of infection prediction introduced above. More specifically, the following example describes prediction of a likelihood of *C. gloeosporioides* infection in a set of similarly sourced avocados.

XII.A. Identification of Infection Biomarkers in Exogenously Infected Avocados

As discussed above, infection biomarkers in a plant product comprise biomarkers that are differentially expressed in infected plant products compared to uninfected plant products. Furthermore, infection biomarkers can include biomarkers that have been determined to be differentially expressed in infected plant products compared to uninfected plant products by a threshold, e.g., of at least 0.1 fold change. To identify C. gloeosporioides infection biomarkers in avocados (e.g., avocado biomarkers that are differentially expressed in avocados infected with C. gloeosporioides compared to avocados that are not infected with C. gloeosporioides), PAL, GST, COMT, WRKY75, F3H, PR6, PR5, ChiB, ChiA, LOX, Prbl-2, and Cat genes were selected for screening. These genes selected for screening as infection biomarkers will be referred to herein as "candidate infection biomarkers."

Each of a plurality of 30 avocados was exogenously inoculated with 100 spores of C. gloeosporioides, and each of a plurality of 30 avocados was exogenously inoculated with water. The avocados inoculated with water served as experimental controls. After 48 hours, each avocado was cored and RNA was extracted. Then, using RT-qPCR, levels of expression of each candidate infection biomarker were determined for each avocado of the plurality of infected avocados and for each avocado of the plurality of control avocados. Levels of expression of a housekeeping biomarker, the Actin gene, were also determined using RT-qPCR for each avocado of the plurality of infected avocados and for each avocado of the plurality of control avocados. The PAL and Actin gene probe sequences and associated fluorophores used to perform qPCR to determine the levels of expression of the PAL and Actin genes respectively are depicted below in Table 3. Probe sequences and associated qPCR fluorophores are also depicted below in Table 3 for infection biomarkers, ACS1 and ACO1 genes.

TABLE 3

Gene Probe Sequences and Fluorophores

| Seq. ID. No. | Gene | Probe (5'-3') | Fluorophore |
|---|---|---|---|
| 1 | PAL | ACTTCCCAGAGGAGAACCAAGCAA | FAM |
| 2 | Actin | TGAAGACTGGCAGTGGATGAG | HEX |
| 3 | ACS1 | TTGTGGAGAATTTCCTGGCCGAGA | ABY |
| 4 | ACO1 | TTGTGGAGAATTTCCTGGCCGAGA | JUN |

Figure 6:
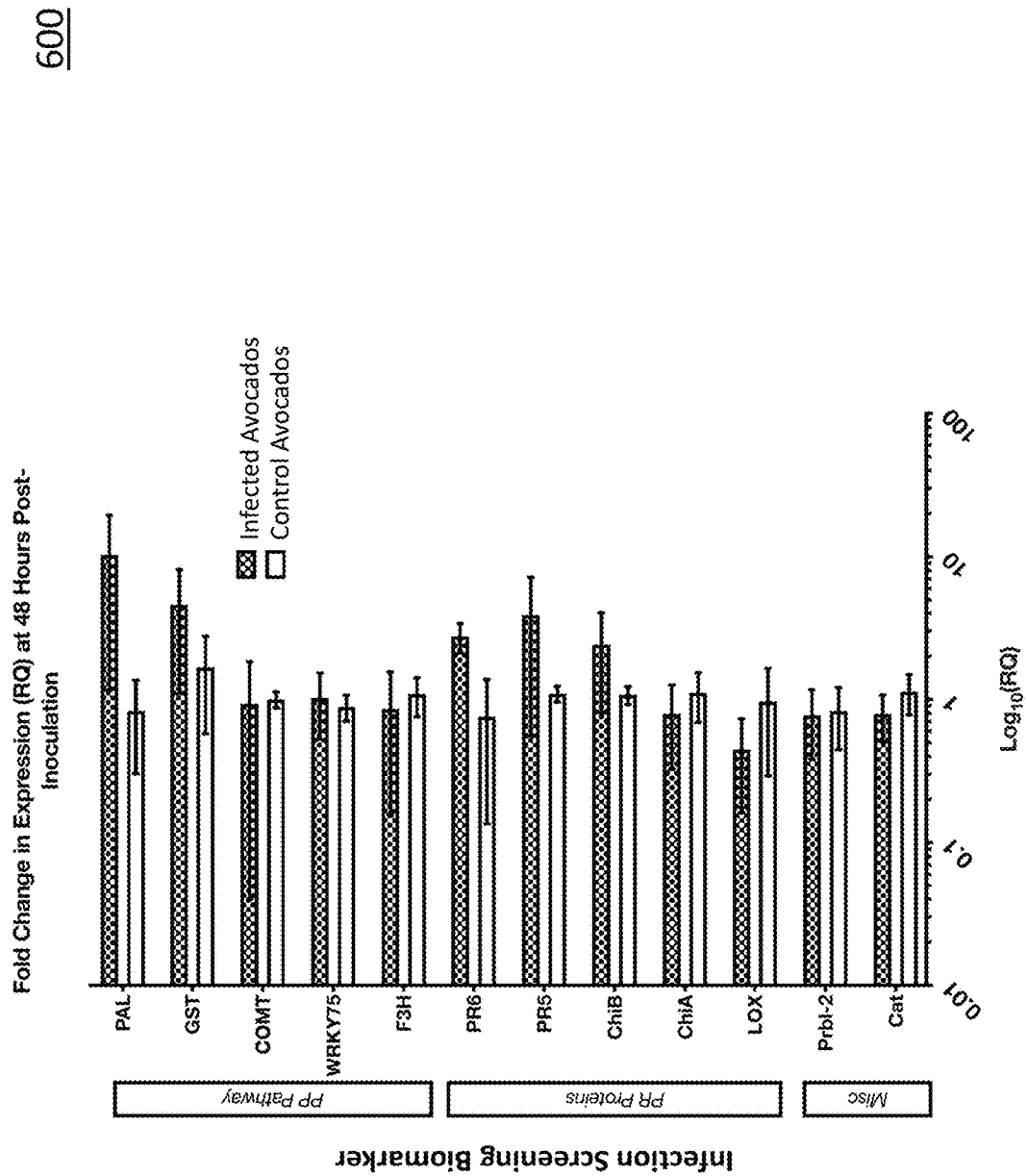
FIG. 6 is a graph that depicts an average normalized level of expression of each candidate infection biomarker for a plurality of infected avocados and for a plurality of control avocados.

A normalized level of expression of each candidate infection biomarker in each avocado of the plurality of infected avocados and in each avocado of the plurality of control avocados was determined based on the levels of expression of the candidate infection biomarker and the Actin gene, as described above with regard to FIG. 2C. Specifically, for each avocado, a normalized level of expression of each candidate infection biomarker was determined by determining a ratio of a $\log_{10}$ level of expression of the candidate infection biomarker in the avocado to a $\log_{10}$ level of expression of the Actin gene in the avocado. Finally, an average normalized level of expression of each candidate infection biomarker was determined for the plurality of infected avocados and for the plurality of control avocados. FIG. 6 is a graph 600 that depicts the average normalized level of expression of each candidate infection biomarker for the plurality of infected avocados and for the plurality of control avocados.

By comparing the average normalized level of expression of a candidate infection biomarker in the plurality of infected avocados to the average normalized level of expression of the candidate infection biomarker in the plurality of control avocados, biomarkers that were differentially expressed in infected avocados compared to control avocados were identified. Specifically, each candidate infection biomarker was determined to exhibit differential expression in infected avocados compared to control avocados of at least 0.1 fold (i.e., the expression of each candidate infection biomarker in infected avocados was at least 1.1 times that in control (uninfected) avocados). Thus, the candidate infection biomarkers, including PAL, GST, COMT, WRKY75, F3H, PR6, PR5, ChiB, ChiA, LOX, Prbl-2, and Cat genes, were identified as true infection biomarkers in avocados.

Furthermore, two genes in the phenylpropanoid pathway (PAL and GST) and three pathogen response genes (PR6, PR5, and ChiB) were identified as being differentially expressed by at least 1 fold in infected avocados compared to control avocados (i.e., the expression of each of these genes in infected avocados was at least 2 times that in control (uninfected) avocados). In other words, of the identified infection genes, the PAL, GST, PR6, PR5, and ChiB genes were determined to exhibit a preferred threshold differential expression of at least 1 fold in avocados at early time points (24 hours or 48 hours post-inoculation). That is, the at least 1 fold (i.e., 100%) increase in expression of these genes in infected avocados could in many cases be detected less than 50 hours, less than 40 hours, less than 30 hours, or less than 25 hours post-inoculation.

Like the infection biomarkers identified in this example, additional infection biomarkers can be identified and listed in Table 1 using similar methods to those described in this example. Similarly, additional infection biomarkers exhibiting differential expression of at least 0.1 fold change between infected and uninfected plant products in examples other than avocado can be identified and listed in Table 1 using similar methods to those described in this example.

XII.B. Identification of Infection Biomarkers in Endogenously Infected Avocados

In addition to identification of infection biomarkers in exogenously infected avocados, infection biomarkers identified above were also confirmed to be correlated with infection in endogenously infected avocados. Specifically, expression of the PAL gene identified as an infection biomarker above was compared in avocados with a high rate of endogenous infection to avocados with a low rate of endogenous infection, to verify that increased expression of the PAL gene is correlated with a high rate of endogenous infection in avocados.

Figure 7A:
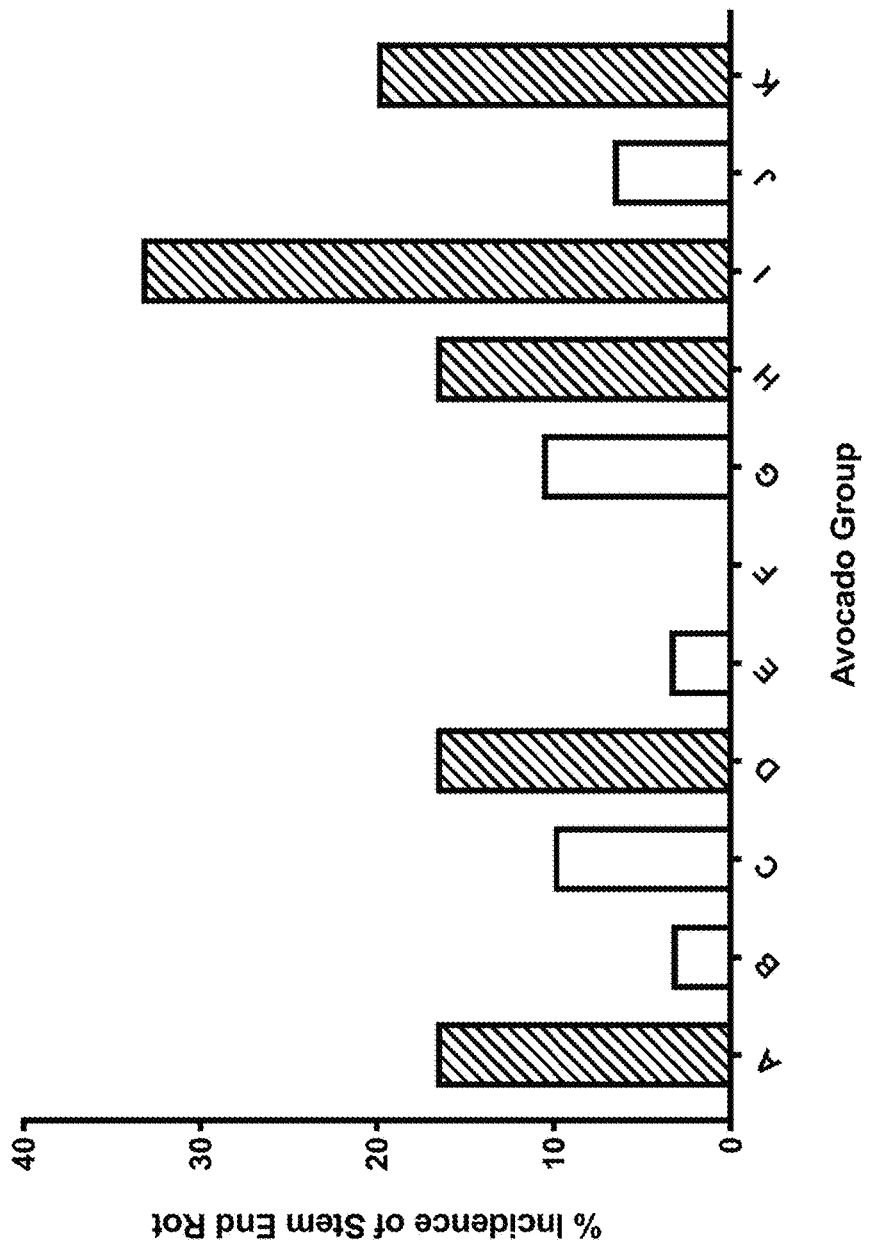
FIG. 7A is a graph that depicts a rate of incidence of stem-end rot in each lot of avocados A-K.

To verify that increased expression of the PAL gene is correlated with a high rate of endogenous infection in avocados, eleven lots of avocados A-K (e.g., sets of similarly sourced avocados with the same packing HUE number) were studied over eleven weeks. Specifically, one lot of avocados was studied each week. From each lot, thirty avocados were set aside for maturation. Once ripe, these thirty avocados were inspected for infection manifested as stem-end rot. Based on this inspection, a rate of incidence of stem-end rot was determined for each set of thirty avocados, and extrapolated to the lot of avocados from which the thirty avocados originated. FIG. 7A is a graph 700A that depicts the rate of incidence of stem-end rot in each lot of avocados A-K. Each lot of avocados A-K was further classified as having either a high (e.g., greater than 5%, 10% or 15%) or low (e.g., less than 5%, 10%, or 15%) rate of incidence of stem-end rot. Lots of avocados having a high rate of incidence of stem-end rot (in this case, 15%) are depicted by bars having a striped fill in FIG. 7A. Conversely, lots of avocados having a low rate of incidence of stem-end rot are depicted by bars having no patterned fill in FIG. 7A.

In addition to inspecting the thirty avocados from each lot A-K for stem-end rot after maturation, prior to maturation, six unripe avocados from each lot were cored and RNA was extracted. Then, using RT-qPCR, levels of expression of the PAL gene were determined for each avocado. Specifically, a copy number of a RNA transcript associated with the PAL gene was determined for each of the six avocados from each lot A-K. Levels of expression of a housekeeping biomarker, the Actin gene, were also determined using RT-qPCR for each avocado. Specifically, a copy number of a RNA transcript associated with the Actin gene was determined for each of the six avocados from each lot A-K. The PAL and Actin gene probe sequences and associated fluorophores used to perform qPCR to determine the levels of expression of the PAL and Actin genes are depicted above in Table 3.

A normalized level of expression of the PAL gene for each avocado was determined based on the level of expression of the PAL gene and the Actin gene. Specifically, for each avocado, a normalized level of expression of the PAL gene was determined by determining a ratio of the level of expression of the PAL gene in the avocado to the level of expression of the Actin gene in the avocado.

Figure 7B:
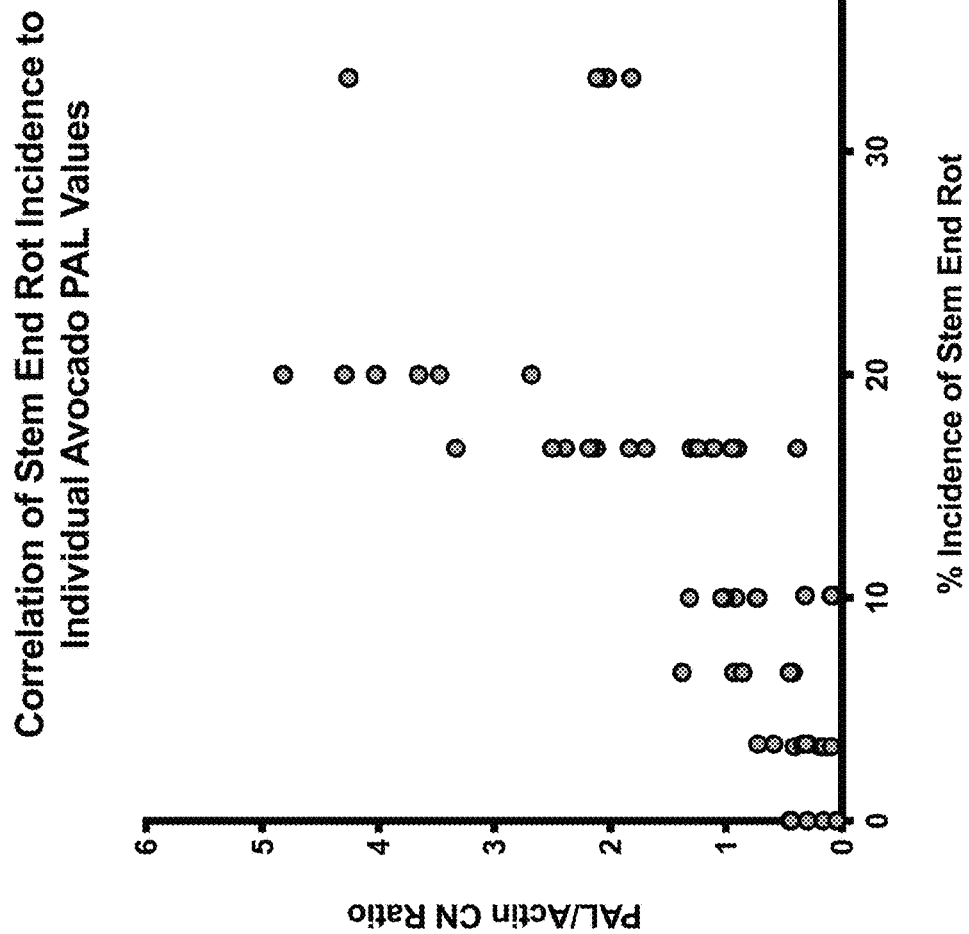
FIG. 7B is a graph that compares a normalized level of expression of the PAL gene in each avocado of six avocados tested from each lot of avocados, to a rate of incidence of stem-end rot in the lot of avocados from which the avocado originated.

FIG. 7B is a graph 700B that compares a normalized level of expression of the PAL gene in each avocado of the six avocados tested from each lot of avocados, to a rate of incidence of stem-end rot in the lot of avocados from which the avocado originated. Each avocado in which a normalized level of expression of the PAL gene was determined is represented as a point in FIG. 7B.

As shown in FIG. 7B, generally, normalized levels of expression of the PAL gene in avocados that originated from a lot of avocados classified as having a high rate of incidence of stem-end rot were greater than in avocados that originated from lots of avocados classified as having a low rate of incidence of stem-end rot. Specifically, 61 of the 66 avocados represented in FIG. 7B (e.g. 92.4%) either demonstrated a high rate of incidence of stem-end rot and a normalized level of PAL expression of greater than 1, or demonstrated a low rate of incidence of stem-end rot and a normalized level of PAL expression of less than 1. Thus, FIG. 7B confirms that increased levels of PAL gene expression are correlated with higher rates of endogenous infection in avocados.

XII.C. Age-Dependent Infection Biomarkers in Avocados

Figure 8:
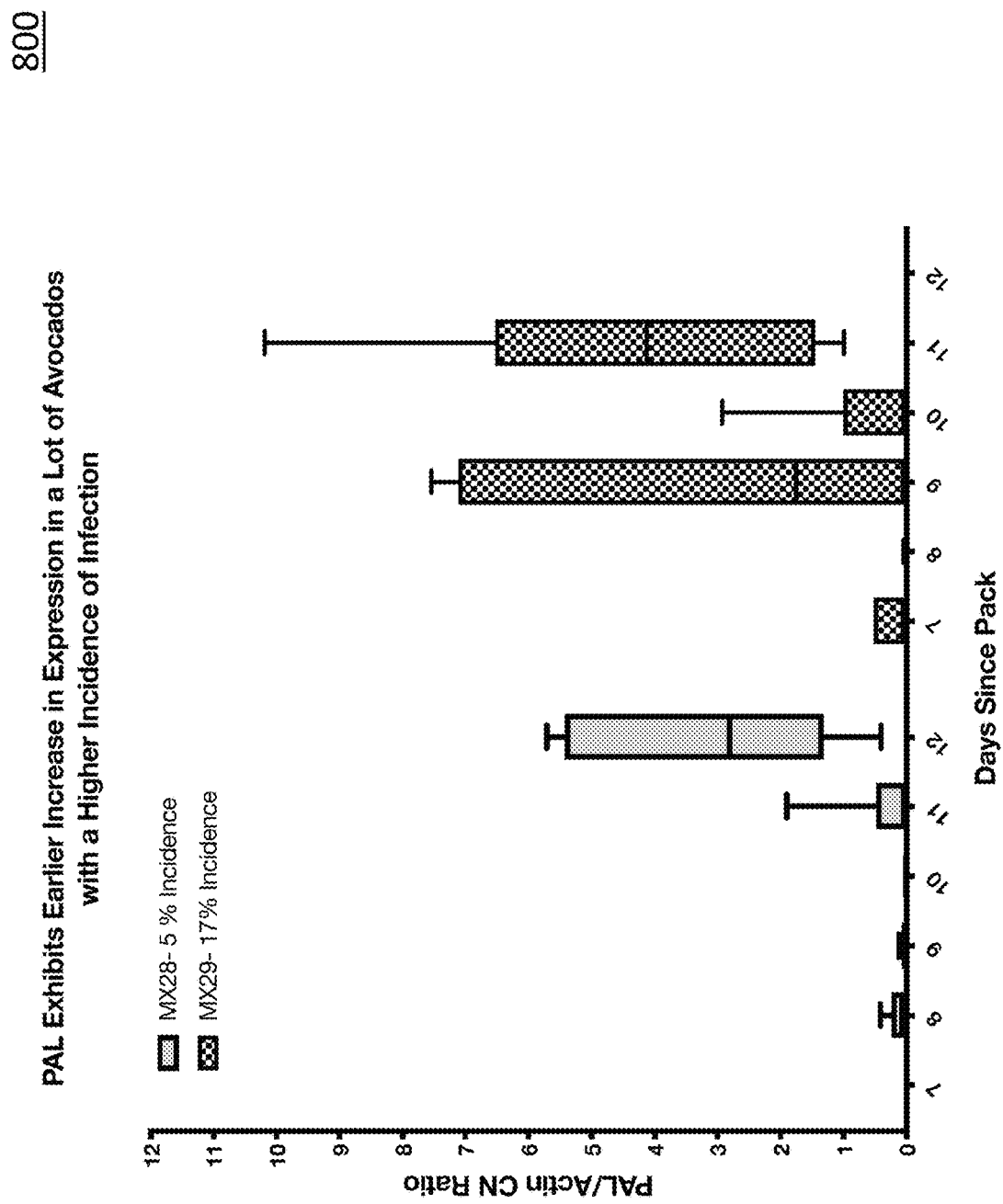
FIG. 8 is a graph that depicts a normalized level of expression of the PAL gene in each of six avocados tested at each of days 7-12 after pack, for both MX28 and MX29 lots of avocados.

In a subsequent experiment, for which results are depicted in FIG. 8, it was determined that the PAL gene is increasingly expressed in avocados as the avocados age. In the experiment, two separate lots of avocados were evaluated. The first lot of avocados, labeled as "MX28" and denoted with a solid grey color in FIG. 8, had a low rate (5%) of incidence of infection. The second lot of avocados, labeled as "MX29" and denoted with a checkered pattern in FIG. 8, had a high rate (17%) of incidence of infection. These rates of incidence of infection were determined by inspecting the lots of avocados for stem-end rot after maturation of the lots as described above with regard to FIG. 7A.

In addition to inspecting the avocados from the two lots for stem-end rot after maturation, six avocados from each lot were tested for PAL gene expression on each of days 7-12 following pack (e.g., harvest) of the avocados. In other words, on each day of days 7-12, inclusive, following pack, six avocados from each of the two lots of avocados MX28 and MX29 were cored and RNA was extracted. Then, using RT-qPCR, levels of expression of the PAL gene were determined for each avocado. Specifically, a copy number of a RNA transcript associated with the PAL gene was determined for each avocado. Levels of expression of a housekeeping biomarker, the Actin gene, were also determined using RT-qPCR for each avocado. Specifically, a copy number of a RNA transcript associated with the Actin gene was determined for each avocados. The PAL and Actin gene probe sequences and associated fluorophores used to perform qPCR to determine the levels of expression of the PAL and Actin genes are depicted above in Table 3.

A normalized level of expression of the PAL gene for each avocado was determined based on the level of expression of the PAL gene and the Actin gene. Specifically, for each avocado, a normalized level of expression of the PAL gene was determined by determining a ratio of the level of expression of the PAL gene in the avocado to the level of expression of the Actin gene in the avocado.

FIG. 8 is a graph 800 that depicts the normalized level of expression of the PAL gene in each of the six avocados tested at each of days 7-12 after pack, for both the MX28 and MX29 lots of avocados. As shown in FIG. 8, for both the MX28 and MX29 lots of avocados, levels of expression of the PAL gene increased over time between the 7-12 days after pack. In other words, levels of expression of the PAL gene in avocados increased over time as the avocados aged. However, as also shown in FIG. 8, on average, levels of expression of the PAL gene increased more over time in avocados from the MX29 lot of avocados (e.g., the lot of avocados with the high rate of incidence of infection) than in the avocados from the MX28 lot of avocados (e.g., the lot of avocados with the low rate of incidence of infection). Furthermore, on average, levels of expression of the PAL gene increased sooner in avocados from the MX29 lot of avocadoes (e.g., the lot of avocados with the high rate of incidence of infection) than in the avocados from the MX28 lot of avocados (e.g., the lot of avocados with the low rate of incidence of infection).

Based on this observation that expression of some infection biomarkers, such as the PAL gene, increase earlier and more over time in ripening avocados with a high rate of incidence of infection compared to avocados with a low rate of incidence of infection, to account for variation in infection biomarker expression between plant products, in some implementations, a normalized level of expression of an infection biomarker can be determined based on the level of expression of the infection biomarker and on a level of expression of another infection biomarker. Specifically, in some implementations, for a given plant product, a normalized level of expression of an infection biomarker can be determined by calculating a ratio of the level of expression of the infection biomarker to the level of expression of another infection biomarker and/or a product of the level of expression of the infection biomarker and the level of expression of another infection biomarker. By normalizing infection biomarker expression to other infection biomarker expression, variations in baseline infection biomarker expression between plant products can be controlled for.

XII.D. Optimization of Training Data Set Generation for Infection Prediction System To sufficiently train the infection prediction system described above to accurately predict likelihoods of infection, a robust training data set is necessary. To generate such a robust training data set to sufficiently train the infection prediction system, methods for generating training samples of the training data set were optimized. In particular, methods of preparing plant products for biomarker analysis were optimized as previously described.

Optimizations of the methods for preparing plant products for biomarker analysis enable the efficient generation of a large training data set for use in training the infection prediction system. Specifically, by employing the optimized plant product preparation methods described above, levels of expression of biomarkers in a plant product can be determined in 6 hours, as opposed to in 1-2 days when the optimized plant product preparation methods described herein are not used. By shortening the length of time required to determine levels of biomarker expression in a plant product from 1-2 days to 6 hours, re-testing of plant product samples can be performed multiple times during a day time point, and this multiplicative data can used to quickly generate large training data sets for the infection prediction system.

For example, due to the shortened length of time required to determine levels of biomarker expression in plant products, 384 avocados from 62 lots at a time point day 0 were re-tested for levels of infection biomarker expression, to correlate infection biomarker expression in each avocado with a rate of incidence of infection in a lot from which the avocado originated, for use in a training data set for an infection prediction system configured to predict a likelihood of infection in an avocado. Specifically, the 384 avocados at the time point day 0 were tested for PAL, Actin, ACS1, and ACO1 gene expression using RT-qPCR. Copy numbers of RNA transcripts associated with the PAL, Actin, ACS1, and ACO1 genes were determined for each avocado. The PAL, Actin, ACS1, and ACO1 gene probe sequences and associated fluorophores used to perform qPCR are depicted above in Tables 3 and 4.

For each avocado, normalized levels of expression of the PAL, ACS1, and ACO1 genes were determined based on the level of expression of the PAL, ACS1, and ACO1 genes and the Actin gene. Specifically, for each avocado, normalized levels of expression of the PAL, ACS1, and ACO1 genes were determined by determining ratios of the levels of expression of the PAL, ACS1, and ACO1 genes in the avocado to the level of expression of the Actin gene in the avocado. Then, for each avocado, feature-scaled levels of expression of the PAL, ACS1, and ACO1 genes were determined by performing min-max normalizations[6] and log transformations of the normalized levels of expression of the PAL, ACS1, and ACO1 genes. Next, a set of biomarker expression statistics for the 384 tested avocados was determined by determining ratios of the feature-scaled levels of expression of the PAL, ACS1, and ACO1 genes for each avocado and products of the feature-scaled levels of expression of the PAL, ACS1, and ACO1 genes for each avocado. Furthermore, following maturation of the 384 avocados, an actual rate of incidence of infection, manifested as stem-end rot, was determined for each training lot of avocados.

The ratios and products of the feature-scaled levels of expression of the PAL, ACS1, and ACO1 genes in each of the 384 avocados, as well as the actual rate of incidence of infection of each lot from which the 384 avocados originated, were used to create a training data set to train the infection prediction system comprising a binary logistic regression model, to predict a likelihood of infection in individual avocados.

During training of the infection prediction system, the infection prediction system predicted a likelihood of infection in each of the 384 avocados associated with the training data set, based on the ratios and products of the feature-scaled levels of expression of the PAL, ACS1, and ACO1 genes in each avocado. Then, for each avocado from the training data set, the predicted likelihood of infection determined by the infection prediction system was compared with the actual rate of incidence of infection of the lot from which the avocado originated. This comparison of predicted likelihood of infection and actual rate of incidence of infection for each avocado in the training data set is depicted in FIG. 9, and is discussed in further detail below.

Following training of the infection prediction system with the training data set based on the 384 avocados, the infection prediction system tested each avocado in 12 lots of test avocados according to a method similar to that described above. More specifically, following training of the infection prediction system, the infection prediction system predicted a likelihood of infection in each of the test avocados. Following maturation of the tested avocados, an actual rate of incidence of infection, manifested as stem-end rot, was determined for each test lot of avocados.

Like the avocados in the training data set, for each avocado from the test data set, the predicted likelihood of infection determined by the infection prediction system was compared with the actual rate of incidence of infection of the lot from which the avocado originated. This comparison of predicted likelihood of infection and actual rate of incidence of infection for each avocado in the test data set is depicted in FIG. 9.

Figure 9:
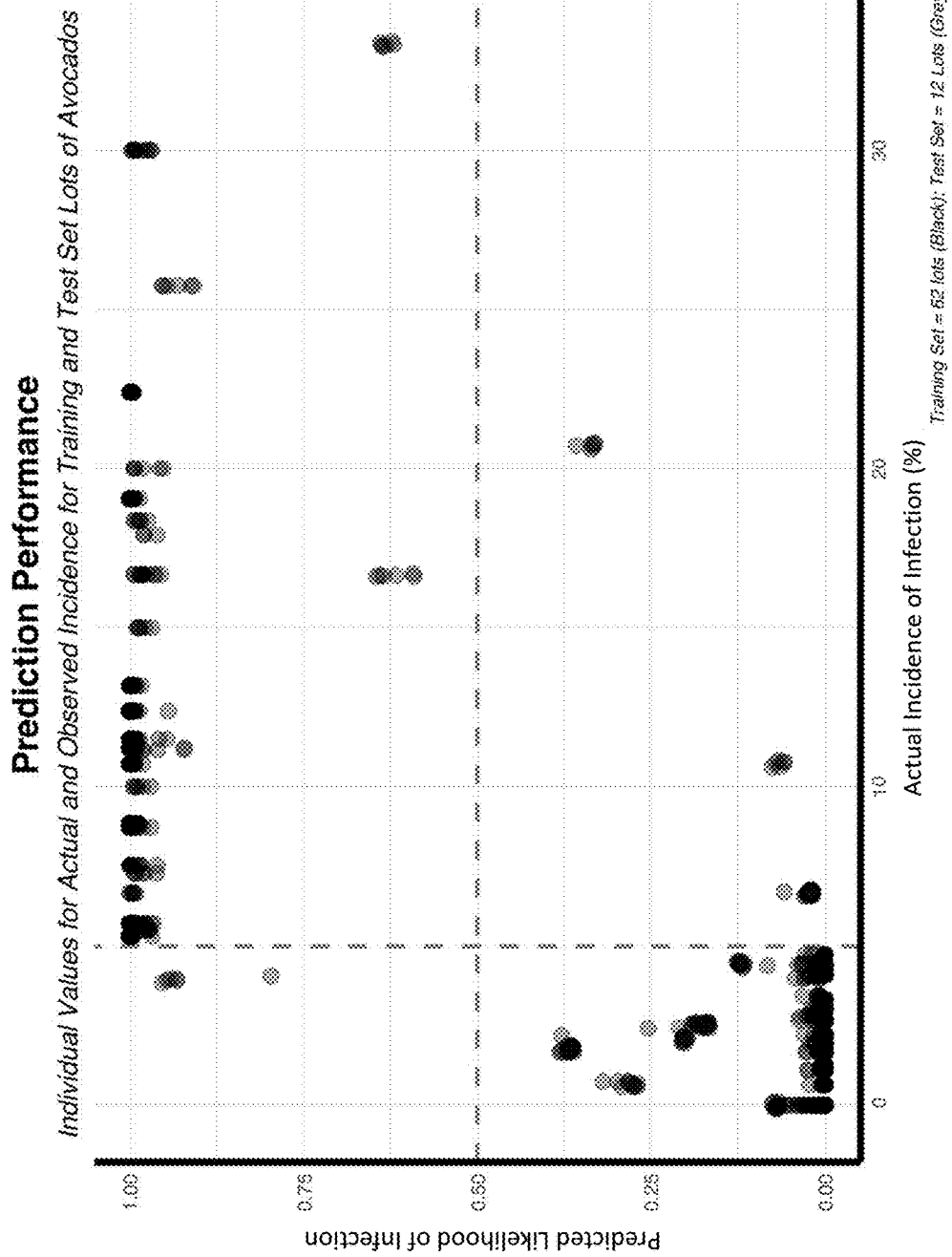
FIG. 9 is a graph that depicts the predictive performance of an infection prediction system.

FIG. 9 is a graph 900 that depicts the predictive performance of the infection prediction system. In FIG. 9, black points represent avocados from the training data set and grey points represent avocados from the test data set. FIG. 9 compares a likelihood of infection each avocado as predicted by the infection prediction system, with an actual rate of incidence of infection in the lot of avocados from which the avocado originated. The dashed horizontal line drawn through FIG. 9 designates a predicted likelihood of infection of 50%, and the dashed vertical line drawn through FIG. 9 designates a rate of incidence of infection threshold of 5%.

The infection prediction system was able to predict with at least 85% accuracy whether an unripe avocado from the training data set belonged to a lot of (similarly sourced) avocados with a greater than 5% rate of incidence of stem-end rot upon ripening. Furthermore, the infection prediction system was able to predict with at least 85% accuracy whether an unripe avocado from the test data set belonged to a lot of (similarly sourced) avocados with a greater than 5% rate of incidence of stem-end rot upon ripening.

XII.E. Infection Prediction System Optimization

In addition to optimizing methods for generating a training data set for the infection prediction system as described above, the infection prediction system itself was also optimized by comparing a variety of different infection prediction systems to one another using an efficient data pipeline to train, validate, and test each infection prediction system. The data pipeline used to train, validate, and test an infection prediction system is described throughout this disclosure, and in particular with regard to FIGS. 1-5D above. Additionally, FIGS. 10A-C depict different granularities of an exemplar data pipeline for training, validating, and testing an infection prediction system.

Figure 10A:
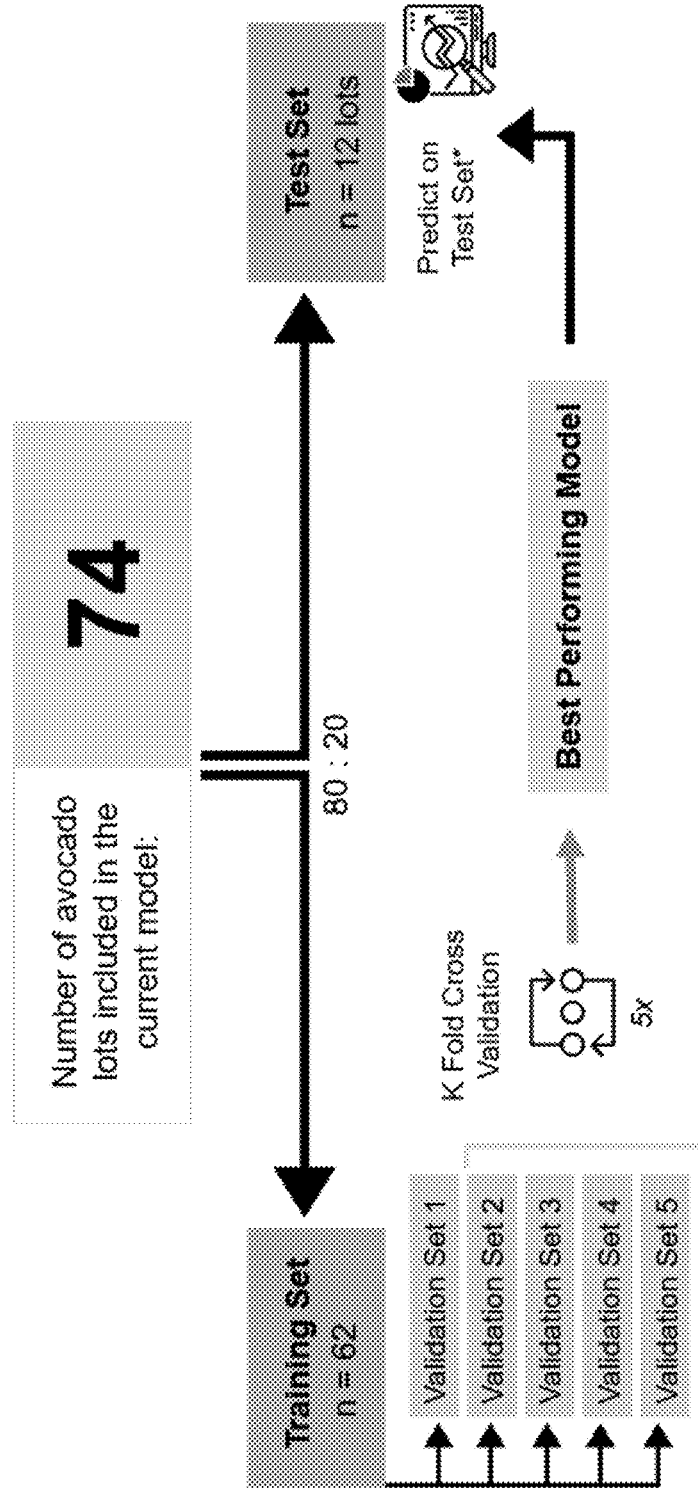
FIG. 10A is a block diagram of an overview of an exemplar data pipeline for training, validating, and testing an infection prediction system.
Figure 10C:
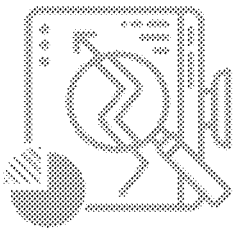
FIG. 10C is a block diagram of an exemplar scheme for testing and assessing performance of an infection prediction system.

FIG. 10A is a block diagram of an overview 1000A of an exemplar data pipeline for training, validating, and testing an infection prediction system. In the implementation depicted in FIG. 10A, 74 sets of similarly sourced plant products (e.g., lots of avocados) are used to train, validate, and test an infection prediction system. As discussed in further detail below with regard to FIG. 10B, in the implementation depicted in FIG. 10A, 80% of the sets of similarly sourced plant products are selected to train and validate the infection prediction system, while 20% of the sets of similarly sourced plant products are selected to test the infection prediction system. Thus, 62 of the 74 sets of similarly sourced plant products are selected to train and validate the infection prediction system, and 12 of the 74 sets of similarly sourced plant products are selected to test the infection prediction system.

Of the 62 sets of similarly sourced plant products used to trained and validate the infection prediction system, 51 of the 62 sets of similarly sourced plant products are used to train the infection prediction system, and 5 of the 62 sets of similarly sourced plant products are used to validate the infection prediction system. As shown in FIG. 10A, validation of the infection prediction system is performed as 5-fold cross validation, meaning that the infection prediction system is validated over 25 total folds of data.

Following training and validation of the infection prediction system, the infection prediction system is tested using the 12 test data sets selected as described above. As described in detail below with regard to FIG. 10C, performance of the infection prediction system on these test data sets can be determined and used to identify the best performing infection prediction systems for future use.

Turning next to FIG. 10B, FIG. 10B is a block diagram of an exemplar data pipeline 1000B for training, validating, and testing an infection prediction system configured to predict whether a set of similarly sourced plant products has a likelihood of infection of greater than or less than 5%. In the implementation depicted in FIG. 10B, the data pipeline of the infection prediction system comprises a starting input and five distinct steps. Also in the implementation depicted in FIG. 10B, the plant product comprises an avocado, and a set of similarly sourced plant products comprises a lot of avocados. However, in alternative implementations, the steps of FIG. 10B can be applied to any alternative plant product.

As shown in FIG. 10B, the starting input comprises an avocado obtained from a lot of similarly sourced avocados. The starting input also comprises levels of expression of one or more infection biomarkers and one of more housekeeping biomarkers in the avocado. In the implementation of the data pipeline in FIG. 10B, the PAL, ACO, and ACS genes are the one or more infection biomarkers, and the Actin gene is the one or more housekeeping biomarkers. In some implementations, a level of expression of a gene can comprise a copy number of an RNA transcript associated with the gene. Particularly, in FIG. 10B, the levels of expression of the Actin, PAL, ACO, and ACS genes in the avocado comprise copy numbers of RNA transcripts associated with the genes in the avocado.

Step 1 of the data pipeline of the infection prediction system comprises determining a normalized level of expression of each infection biomarker in the avocado based on the level of expression of the infection biomarker and the housekeeping biomarker. More specifically, in step 1, a normalized level of expression of each infection biomarker in the avocado is determined by determining a ratio of the copy number of RNA transcripts associated with the infection biomarker in the avocado to the copy number of RNA transcripts associated with the housekeeping biomarker in the avocado. Thus, as shown in FIG. 10B, a ratio of the copy number of RNA transcripts associated with the PAL gene to the copy number of RNA transcripts associated with the Actin gene (e.g., PAL/Actin) is determined, a ratio of the copy number of RNA transcripts associated with the ACO gene to the copy number of RNA transcripts associated with the Actin gene (e.g., ACO/Actin) is determined, and a ratio of the copy number of RNA transcripts associated with the ACS gene to the copy number of RNA transcripts associated with the Actin gene (e.g., ACS/Actin) is determined.

Next, in step 2 of the data pipeline depicted in FIG. 10B, a feature-scaled level of expression of the normalized level of expression of each infection biomarker determined in step 1 is determined. To determine a feature-scaled level of expression of a normalized level of expression of an infection biomarker, a mathematical normalization function is applied to the normalized level of expression of the infection biomarker. For example, in certain implementations, a feature-scaled level of expression of a normalized level of expression of an infection biomarker is determined by performing at least one of a min-max normalization$^6$ and a log transformation of the normalized level of expression of the infection biomarker. In step 2, feature-scaled levels of expression are determined for the normalized levels of expression of the PAL, ACO, and ACS genes.

Then, in step 3, individual avocados that have undergone steps 1-2 as described above are grouped together according to the lot from which they originated. In other words, subsets of individual avocados originating from a common set of similarly sourced avocados are grouped together. Then, a set of biomarker expression statistics is determined for each subset of avocados based on the feature-scaled level of expression of each infection biomarker determined for each avocado of the subset. In some implementations, a set of biomarker expression statistics for a subset of avocados comprises at least one of a mean, median, minimum, maximum, standard deviation, $5^{th}$ percentile, $10^{th}$ percentile, $15^{th}$ percentile, $20^{th}$ percentile, $25^{th}$ percentile, $50^{th}$ percentile, $75^{th}$ percentile, $80^{th}$ percentile, $90^{th}$ percentile, $95^{th}$ percentile and $99^{th}$ percentile of the feature-scaled levels of expression of each infection biomarker determined for the avocados in the subset, ratios of the feature-scaled levels of expression of each infection biomarker to the feature-scaled level of expression of each other infection biomarker for each avocado of the subset of avocados, and products of the feature-scaled levels of expression of each infection biomarker and the feature-scaled level of expression of each other infection biomarker for each avocado of the subset of avocados.

Finally, in step 3, following maturation of the set of similarly sourced avocados from which the subset of avocados originated, the set of similarly sourced avocados are inspected for infection manifested as stem-end rot. Based on this inspection, an actual rate of incidence of stem-end rot is determined for each set of similarly sourced avocados, and each set of similarly sourced avocados is classified as having, for example, either a greater than 5% or less than 5% rate of incidence of stem-end rot.

Turning next to step 4, subsets of avocados for which sets of biomarker expression statistics and rates of incidence of stem-end rot have been determined are randomly selected to either train the infection prediction system or to test the infection prediction system. In the implementation shown in FIG. 10B, 80% of the subsets of avocados processed in step 3 are selected to train the infection prediction system, while 20% of the subsets of plants products processed in step 3 are selected to test the infection prediction system.

Finally, in step 5 of the data pipeline depicted in FIG. 10B, the infection prediction system is trained using the training data set selected in step 4. As discussed in detail above with regard to FIGS. 4 and 5B, training the infection prediction system involves optimizing the parameters of the system to minimize the loss function. In addition to training the infection prediction system in step 5, the infection prediction system also undergoes validation using held-out training data samples, as discussed above in detail with regard to FIGS. 5C and 10A. Following training and validation of the infection prediction system in step 5, the infection prediction system is ready to be tested using the test data set selected in step 4, as discussed below with regard to FIG. 10C.

Turning to FIG. 10C, FIG. 10C is a block diagram of an exemplar scheme 1000C for testing and assessing performance of the infection prediction system of FIG. 10B. As shown in FIG. 10C, the trained and validated infection prediction system from FIG. 10B is tested as discussed above in detail with regard to FIG. 5D, using the test data set selected in step 4 of the data pipeline of FIG. 10B. Specifically, for each subset of avocados included in the test data set, the biomarker expression statistics determined for the subset in step 3 of FIG. 10B are input into the infection prediction system. The infection prediction system then outputs a prediction of whether a set of similarly sourced avocados from which the subset of avocados originated has a likelihood of infection of greater than or less than, for example, 5%.

Finally, for each subset of avocados tested, the infection prediction system's prediction of the likelihood of infection in the set of similarly sourced avocados from which the subset of avocados originated, is compared to the known rate of incidence of infection in the set of similarly sourced avocados as determined in step 3 of FIG. 10B. Based on this comparison, an accuracy, precision, and recall of the infection prediction system can be determined.

The performance of different infection prediction systems can be compared to select the best system for use in future infection predictions. In other words, the data pipeline described above in FIGS. 10A-C enables efficient and repeatable infection prediction system development, comparison, and optimization. For example, the data pipeline described above facilitated the development and evaluation of a variety of different infection prediction systems, including a binary logistic regression model (BLM), logistic model tree (LMT), random forest classifier (RF), L2 regularization (L2), Naïve Bayes classifier (NB), multivariate adaptive regression spines (MARS), one or more neural networks, and k-nearest neighbor classification (KNN). Table 4 below depicts a mean validation accuracy on the training data set described with regard to FIG. 10B, and a mean accuracy, precision, and recall on the test data set described with regard to FIGS. 10A-B, for each of these different infection prediction systems.

TABLE 4

Comparison of Infection Prediction Systems

| Infection Prediction System | Mean Validation Accuracy on Training Data Set (Over 25 Folds of Data) | Mean Accuracy on Test Data Set | Mean Precision on Test Data Set | Mean Recall on Test Data Set |
|---|---|---|---|---|
| RF | 61% | 92% | 80% | 100% |
| MARS | 46% | 42% | 30% | 60% |
| L2 | 62% | 83% | 60% | 100% |
| GLM | 52% | 83% | 80% | 86% |

TABLE 4-continued

Comparison of Infection Prediction Systems

| Infection Prediction System | Mean Validation Accuracy on Training Data Set (Over 25 Folds of Data) | Mean Accuracy on Test Data Set | Mean Precision on Test Data Set | Mean Recall on Test Data Set |
|---|---|---|---|---|
| PLS | 66% | 75% | 100% | 40% |
| KNN | 63% | 92% | 80% | 100% |
| NB | 61% | 67% | 20% | 100% |

As shown in Table 4, the most accurate infection prediction systems include the RF and KNN-based systems. The infection prediction systems comprising the RF and KNN infection prediction systems both achieve 92% mean accuracy when tested using the test data set as described above with regard to FIG. 10C.

XIII. Example Computer

Figure 11:
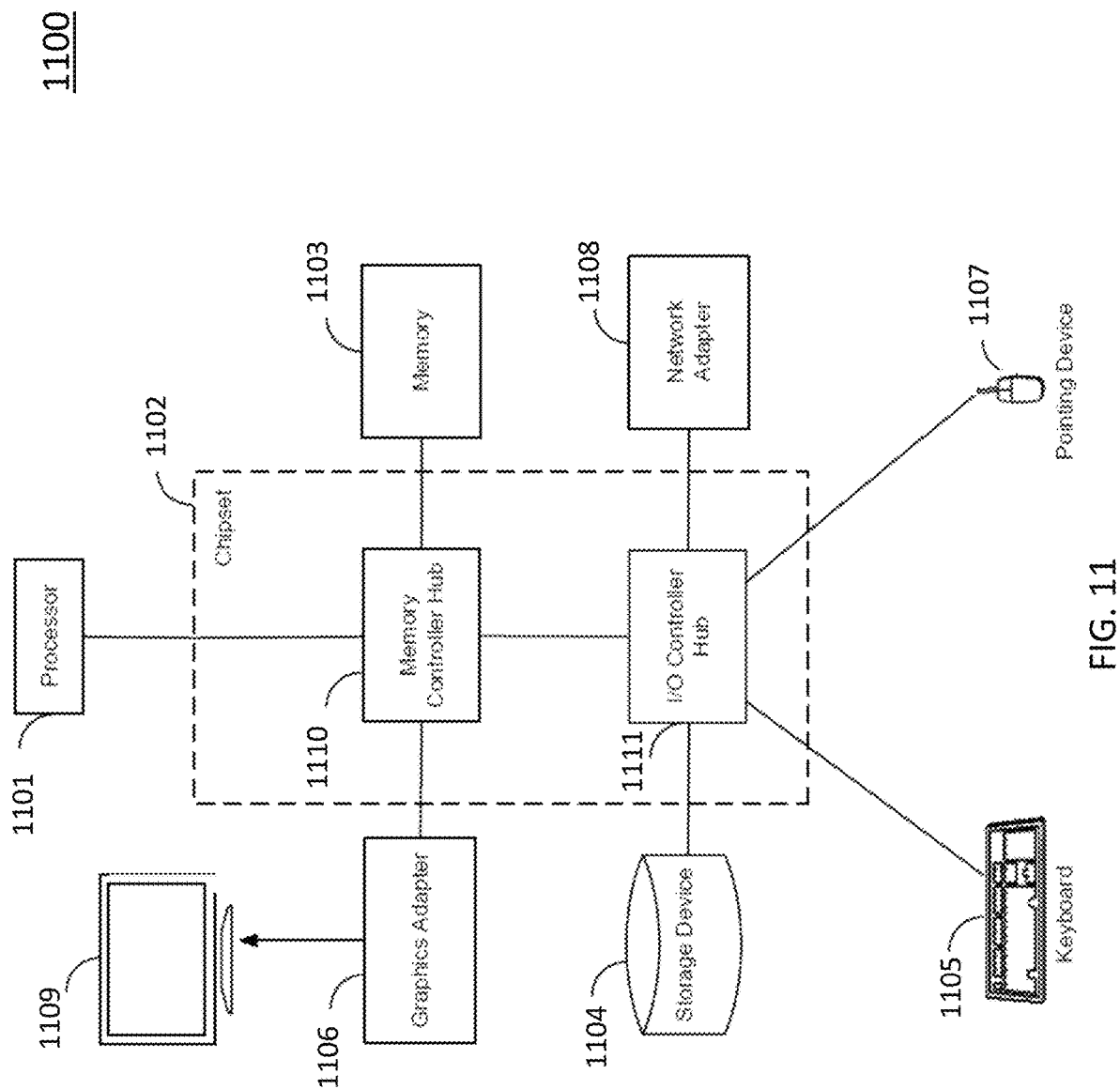
FIG. 11 illustrates an example computer for implementing the method described in FIG. 1.

FIG. 11 illustrates an example computer 1100 for implementing the method described in FIG. 1. The computer 1100 includes at least one processor 1102 coupled to a chipset 1104. The chipset 1104 includes a memory controller hub 1120 and an input/output (I/O) controller hub 1122. A memory 1106 and a graphics adapter 1112 are coupled to the memory controller hub 1120, and a display 1118 is coupled to the graphics adapter 1112. A storage device 1108, an input device 1114, and network adapter 1116 are coupled to the I/O controller hub 1122. Other implementations of the computer 1100 have different architectures.

The storage device 1108 is a non-transitory computer-readable storage medium such as a hard drive, compact disk read-only memory (CD-ROM), DVD, or a solid-state memory device. The memory 1106 holds instructions and data used by the processor 1102. The input interface 1114 is a touch-screen interface, a mouse, track ball, or other type of pointing device, a keyboard, or some combination thereof, and is used to input data into the computer 1100. In some implementations, the computer 1100 may be configured to receive input (e.g., commands) from the input interface 1114 via gestures from the user. The graphics adapter 1112 displays images and other information on the display 1118. The network adapter 1116 couples the computer 1100 to one or more computer networks.

The computer 1100 is adapted to execute computer program modules for providing functionality described herein. As used herein, the term "module" refers to computer program logic used to provide the specified functionality. Thus, a module can be implemented in hardware, firmware, and/or software. In one implementation, program modules are stored on the storage device 1108, loaded into the memory 1106, and executed by the processor 1102.

The types of computers 1100 used to implement the method of FIG. 1 can vary depending upon the implementation and the processing power required by the entity. For example, the presentation identification system 160 can run in a single computer 1100 or multiple computers 1100 communicating with each other through a network such as in a server farm. The computers 1100 can lack some of the components described above, such as graphics adapters 1112, and displays 1118.

XIV. Additional Considerations

It should be noted that, as used in the specification and the appended claims, the singular forms "a," "an," and "the" include plural referents unless the context clearly dictates otherwise.

All references, issued patents and patent applications cited within the body of the specification are hereby incorporated by reference in their entirety, for all purposes.

The foregoing description of the implementations of the present disclosure has been presented for the purpose of illustration; it is not intended to be exhaustive or to limit the present disclosure to the precise forms disclosed. Persons skilled in the relevant art can appreciate that many modifications and variations are possible in light of the above disclosure.

Some portions of this description describe the implementations of the present disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one implementation, a software module is implemented with a computer program product including a computer-readable non-transitory medium containing computer program code, which can be executed by a computer processor for performing any or all of the steps, operations, or processes described.

Implementations may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Implementations of the present disclosure may also relate to a product that is produced by a computing process described herein. Such a product may include information resulting from a computing process, where the information is stored on a non-transitory, tangible computer-readable storage medium and may include any implementation of a computer program product or other data combination described herein.

Finally, the language used in the specification has been principally selected for readability and instructional purposes, and it may not have been selected to delineate or circumscribe the inventive subject matter. It is therefore intended that the scope of the present disclosure be limited not by this detailed description, but rather by any claims that issue on an application based hereon. Accordingly, the disclosure of the implementations of the present disclosure is intended to be illustrative, but not limiting, of the scope of the present disclosure.

What is claimed is:

1. A method for identifying a latent infection in a plant product, the method comprising:
  obtaining, by a processor, data describing a level of expression of one or more infection biomarkers of a plant product, the infection biomarkers indicating a likelihood of infection in the plant product, wherein the data identifies one or more variants that describe differences between a read sequence of the plant product and a reference genome of a healthy plant product;
  encoding, by the processor, the obtained data into a data structure for input to a machine learning model;
  providing, by the processor, the encoded data structure as input to the machine learning model for executing the machine learning model, wherein the machine learning model was previously trained, wherein the machine learning model comprises a function that represents a relationship between independent and dependent variables in a training data set such that a loss function is minimized, wherein the machine learning model was trained using a process comprising:
    inputting, from the training data set, (i) a first set of training samples of infection biomarkers of one or more other plant products and (ii) known rates of infection for the first set of training samples into the machine learning model,
    determining predicted likelihoods of infection in the one or more other plant products based on inputting the first set of training samples of infection biomarkers of the one or more of the other plant products (i) and (ii) into the machine learning model,
    determining a difference between the predicted likelihoods of infection and the known rates of infection for the first set of training samples,
    minimizing the loss function for the machine learning model based on the determined difference,
    determining, by using gradient-based numerical optimization, a set of values for a set of parameters that minimize the loss function;
    modifying the function of the machine learning model using the determined set of values for the set of parameters and providing the machine learning model for validating, and
    validating, using the set of parameters, the machine learning model until the loss function for the machine learning model is within a predetermined threshold range, wherein validating the machine learning model comprises:
      inputting a second set of training samples from the training data set into the machine learning model, and
      outputting the validated machine learning model for runtime use based on determining that the loss function for the machine learning model is within the predetermined threshold range;
    obtaining, by the processor and based on executing the output machine learning model based on the encoded data, generated output data indicating a likelihood that the plant product has a latent infection;
  determining, by the processor and based on the generated output data, that the plant product has a latent infection; and
  performing, by the processor, one or more operations to mitigate the latent infection in the plant product.

2. The method of claim 1, wherein the machine learning model includes one or more of a binary logistic regression model, logistic model tree, random forest classifier, L2 regularization, partial least squares, Naive Bayes classifier, multivariate adaptive regression spines, convolutional neural networks (CNNs), and k-nearest neighbor classification.

3. The method of claim 1, wherein the plant product does not include any visible signs of an infection.

4. The method of claim 1, the method further comprising:
  selecting, by the processor, a subset of m plant products from the set of plant products, wherein m is an integer greater than 1 and less than n/2; and
  for each plant product of the subset, determining, by the processor, a level of expression of one or more infection biomarkers;
  wherein obtaining, by the processor, data describing a level of expression of one or more biomarkers in a plant product comprises:
    obtaining, for each plant product of the subset, data describing the determined level of expression of the one or more infection biomarkers; and
  wherein encoding, by the processor, the obtained data into a data structure for input to a machine learning model comprises:
    encoding the obtained data describing the determined level of expression of the one or more infection biomarkers into one or more data structures for input to the machine learning model.

5. The method of claim 1, further comprising providing, by the processor, the encoded data structure as input to multiple machine learning models, wherein the multiple machine learning models were previously trained, using data that correlates other encoded data structures and determined one or more infection biomarkers of one or more other plant products, to predict likelihoods of infection in the one or more other plant products.

6. The method of claim 5, wherein each of the multiple machine learning models was previously trained to predict likelihood of a particular type of infection in the one or more other plant products.

7. The method of claim 1, further comprising training, by the processor, the machine learning model with the output data indicating the likelihood that the plant product has a latent infection that was generated by the machine learning model during runtime.

8. The method of claim 1, wherein performing, by the processor, one or more operations to mitigate the latent infection in the plant product comprises identifying, based on the generated output data, a set of similarly sourced plant products that is at risk of developing the latent infection.

9. The method of claim 1, wherein performing, by the processor, one or more operations to mitigate the latent infection in the plant product comprises determining a quantity of anti-microbial treatment to apply to the plant product.

10. A system for identifying a latent infection in a plant product comprising:
- at least one processor; and
- a memory device storing instructions that when executed by the at least one processor cause the at least one processor to perform operations comprising:
- obtaining data describing a level of expression of one or more infection biomarkers of a plant product, the infection biomarkers indicating a likelihood of infection in the plant product, wherein the data identifies one or more variants that describe differences between a read sequence of the plant product and a reference genome of a healthy plant product;
- encoding the obtained data into a data structure for input to a machine learning model;
- providing, by the processor, the encoded data structure as input to the machine learning model for executing the machine learning model, wherein the machine learning model was previously trained, wherein the machine learning model comprises a function that represents a relationship between independent and dependent variables in a training data set such that a loss function is minimized, wherein the machine learning model was trained using a process comprising:
  - inputting, from the training data set, (i) a first set of training samples of infection biomarkers of one or more other plant products and (ii) known rates of infection for the first set of training samples into the machine learning model,
  - determining predicted likelihoods of infection in the one or more other plant products based on inputting the first set of training samples of infection biomarkers of the one or more of the other plant products into the machine learning model,
  - determining a difference between the predicted likelihoods of infection and the known rates of infection for the first set of training samples,
  - minimizing the loss function for the machine learning model based on the determined difference,
  - determining, by using gradient-based numerical optimization, a set of values for a set of parameters that minimize the loss function;
  - modifying the function of the machine learning model using the determined set of values for the set of parameters and providing the machine learning model for validating, and
  - validating, using the set of parameters, the machine learning model until the loss function for the machine learning model is within a predetermined threshold range, wherein validating the machine learning model comprises:
    - inputting a second set of training samples from the training data set into the machine learning model, and
    - outputting the validated machine learning model for runtime use based on determining that the loss function for the machine learning model is within the predetermined threshold range;
- obtaining, by the processor and based on executing the output machine learning model based on the encoded data, generated output data indicating a likelihood that the plant product has a latent infection;
- determining, by the processor and based on the generated output data, that the plant product has a latent infection; and
- performing, by the processor, one or more operations to mitigate the latent infection in the plant product.

11. The system of claim 10, wherein the machine learning model includes one or more of a binary logistic regression model, logistic model tree, random forest classifier, L2 regularization, partial least squares, Naive Bayes classifier, multivariate adaptive regression spines, convolutional neural networks (CNNs), and k-nearest neighbor classification.

12. The system of claim 10, wherein the plant product does not include any visible signs of an infection.

13. The system of claim 10, the operations further comprising providing the encoded data structure as input to multiple machine learning models, wherein the multiple machine learning models were previously trained, using data that correlates other encoded data structures and determined one or more infection biomarkers of one or more other plant products, to predict likelihoods of infection in the one or more other plant products.

14. The system of claim 13, wherein each of the multiple machine learning models was previously trained to predict likelihood of a particular type of infection in the one or more other plant products.

15. The system of claim 10, the operations further comprising training the machine learning model with the output data indicating the likelihood that the plant product has a latent infection that was generated by the machine learning model during runtime.

16. A non-transitory computer-readable medium storing instructions stored thereon that, when executed by at least one processor of a computing device, cause the at least one processor of the computing device to perform operations comprising:
- obtaining data describing a level of expression of one or more infection biomarkers of a plant product, the infection biomarkers indicating a likelihood of infection in the plant product, wherein the data identifies one or more variants that describe differences between a read sequence of the plant product and a reference genome of a healthy plant product;
- encoding the obtained data into a data structure for input to a machine learning model;
- providing, by the processor, the encoded data structure as input to the machine learning model for executing the machine learning model, wherein the machine learning model was previously trained, wherein the machine learning model comprises a function that represents a relationship between independent and dependent variables in a training data set such that a loss function is minimized, wherein the machine learning model was trained using a process comprising:
  - inputting, from the training data set, (i) a first set of training samples of infection biomarkers of one or more other plant products and (ii) known rates of infection for the first set of training samples into the machine learning model,
  - determining predicted likelihoods of infection in the one or more other plant products based on inputting the first set of training samples of infection biomarkers of the one or more of the other plant products into the machine learning model,
  - determining a difference between the predicted likelihoods of infection and the known rates of infection for the first set of training samples, minimizing the loss function for the machine learning model base on the determined difference, determining, by using gradient-based numerical optimization, a set of values for a set of parameters that minimize the loss function;

modifying the function of the machine learning model using the determined set of values for the set of parameters and providing the machine learning model for validating, and validating, using the set of parameters, the machine learning model until the loss function for the machine learning model is within a predetermined threshold range, wherein validating the machine learning model comprises:

inputting a second set of training samples from the training data set into the machine learning model, and outputting the validated machine learning model for runtime use based on determining that the loss function for the machine learning model is within the predetermined threshold range;

obtaining, by the processor and based on executing the output machine learning model based on the encoded data, generated output data indicating a likelihood that the plant product has a latent infection;

determining, by the processor and based on the generated output data, that the plant product has a latent infection; and performing, by the processor, one or more operations to mitigate the latent infection in the plant product.

17. The non-transitory computer-readable medium of claim 16, the operations further comprising providing the encoded data structure as input to multiple machine learning models, wherein the multiple machine learning models were previously trained, using data that correlates other encoded data structures and determined one or more infection biomarkers of one or more other plant products, to predict likelihoods of infection in the one or more other plant products.

18. The non-transitory computer-readable medium of claim 17, wherein each of the multiple machine learning models was previously trained to predict likelihood of a particular type of infection in the one or more other plant products.

19. The non-transitory computer-readable medium of claim 16, the operations further comprising training the machine learning model with the output data indicating the likelihood that the plant product has a latent infection that was generated by the machine learning model during runtime.

\* \* \* \* \*

SEQUENCE LISTING

```
<160> NUMBER OF SEQ ID NOS: 4

<210> SEQ ID NO 1
<211> LENGTH: 24
<212> TYPE: DNA
<213> ORGANISM: Persea americana

<400> SEQUENCE: 1
acttcccaga ggagaaccaa gcaa                                              24

<210> SEQ ID NO 2
<211> LENGTH: 21
<212> TYPE: DNA
<213> ORGANISM: Persea americana

<400> SEQUENCE: 2
tgaagactgg cagtggatga g                                                 21

<210> SEQ ID NO 3
<211> LENGTH: 24
<212> TYPE: DNA
<213> ORGANISM: Persea americana

<400> SEQUENCE: 3
ttgtggagaa tttcctggcc gaga                                              24

<210> SEQ ID NO 4
<211> LENGTH: 24
<212> TYPE: DNA
```

```
<213> ORGANISM: Persea americana

<400> SEQUENCE: 4
ttgtggagaa tttcctggcc gaga                                            24
```